(12) United States Patent
Traynor-Kaplan et al.

(10) Patent No.: US 7,453,006 B2
(45) Date of Patent: Nov. 18, 2008

(54) INOSITOL DERIVATIVES FOR INCREASING CHLORIDE SECRETION AND INHIBITING INFLAMMATION

(75) Inventors: Alexis Traynor-Kaplan, North Bend, WA (US); Carsten Schultz, Heidelberg (DE); Tanja Meyerdierks, Rotenburg (DE); Mark Moody, Seattle, WA (US); Andrew Schnaars, Osterholz-Scharmbeck (DE); Jane Smith, Bellevue, WA (US)

(73) Assignee: Inologic, Inc., Seattle, WA (US)

( * ) Notice: Subject to any disclaimer, the term of this patent is extended or adjusted under 35 U.S.C. 154(b) by 160 days.

(21) Appl. No.: 10/432,340

(22) PCT Filed: Nov. 21, 2001

(86) PCT No.: PCT/US01/43664

§ 371 (c)(1),
(2), (4) Date: Mar. 22, 2004

(87) PCT Pub. No.: WO02/41831

PCT Pub. Date: May 30, 2002

(65) Prior Publication Data

US 2004/0147487 A1     Jul. 29, 2004

Related U.S. Application Data

(60) Provisional application No. 60/252,603, filed on Nov. 21, 2000.

(51) Int. Cl.
*C07F 9/20*     (2006.01)
(52) U.S. Cl. ........................................... 558/70
(58) Field of Classification Search ............... 558/70
See application file for complete search history.

(56) References Cited

U.S. PATENT DOCUMENTS

| | | |
|---|---|---|
| 5,157,140 A | 10/1992 | Siren |
| 5,977,078 A | 11/1999 | Traynor-Kaplan |
| 6,221,856 B1 | 4/2001 | Traynor-Kaplan et al. |

FOREIGN PATENT DOCUMENTS

| | | |
|---|---|---|
| EP | 0 583 699 A1 | 2/1994 |
| WO | WO 95/14477 A1 | 6/1995 |
| WO | WO 98/11901 A1 | 3/1998 |

*Primary Examiner*—Taofiq A Solola
(74) *Attorney, Agent, or Firm*—Christensen O'Connor Johnson Kindness PLLC

(57) ABSTRACT

Inositol derivatives, compositions comprising inositol derivatives, and methods for using compositions comprising inositol derivatives as agents for activating the secretion of chloride ions and/or treatment of inflammation are described.

3 Claims, 15 Drawing Sheets

INOSITOL DERIVATIVES FOR INCREASING CHLORIDE SECRETION AND INHIBITING INFLAMMATION

CROSS-REFERENCE TO RELATED APPLICATION

This application claims the benefit of U.S. Provisional Application No. 60/252,603, filed Nov. 21, 2000.

FIELD OF THE INVENTION

The present invention relates to inositol derivatives that activate the secretion of chloride ions, promoting hydration of mucosal surfaces which is deficient in mucosal epithelia of patients suffering from cystic fibrosis, and/or that inhibit inflammation. The present invention also relates to compositions comprising the inositol derivatives and methods for their use, alone or in combination with other therapeutic agents, for treating pathological conditions related to cystic fibrosis and/or inflammation in humans.

BACKGROUND OF THE INVENTION

Cystic fibrosis(CF) is the most common genetic disorder and the largest genetic killer of children. One in twenty Caucasians carries a defective CF gene, which, when coupled with a spouse who is also a carrier can result in offspring afflicted with CF. An autosomal, recessive disorder, one in 3,000 children born in the United States and Europe inherit CF. Children live for varying periods of time, but the average has been extended from a couple of years early in this century to a current life expectancy of 30 years. Over 70,000 patients have been identified with Cystic Fibrosis worldwide. This translates into over 30,000 individuals with the disease in the United States with another 30,000 who have been identified with the disorder in Europe. As current treatment strategies prolong the average lifespan, the number of CF patients is expected to rise. Patients with CF typically incur medical costs ranging from $15,000 to $55,000 annually. In addition, carriers of CF (about 5% of Caucasians) have a higher likelihood of suffering from sinusitis, a disease of the sinus passages characterized by recurrent infections.

CF is due to a genetic defect in a chloride-channel in mucus membranes that regulates the passage of chloride, sodium and water into mucous linings. This leads to unusually thick mucus, particularly in the lungs, which encourages the growth of bacteria and consequently repeated infections and inflammation.

In a majority of CF victims, the cystic fibrosis transmembrane regulator (CFTR), an epithelial chloride channel, is defective. In 70% of the cases this is due to a single point mutation at ΔF508. Thus, CF mucosal epithelial cells are incapable of transferring sufficient amounts of chloride ions to the outer membrane surface to draw enough water to adequately hydrate the mucous membranes. The inherited disease process of CF affects tissues of mucous membranes such as those lining throat, nasal, sinus, bronchial passages, lungs, gall bladder, sweat glands, pancreas and intestines.

The disease causes abnormally viscous mucous secretions that lead to chronic pulmonary disease, pancreatic insufficiency and intestinal obstructions, together with a host of lesser but potentially lethal problems, such as an excessive loss of electrolytes in hot environments. In the past, afflicted children often died as infants. Although surviving into their twenties and thirties with current treatments, CF patients are plagued with recurrent infections and require daily arduous routines to clear air passageways.

It is believed that agents that promote chloride secretion such as purinergic agonists and other agents that elevate intracellular calcium could be useful in increasing hydration of the airways, thus reducing mucous viscosity. However, it is known that nucleotides already present in the fluid lining the lungs should be sufficient to stimulate a rise in levels of intracellular calcium. Thus, it may also be necessary to inactivate pathways that limit chloride secretion, such as those mediated by inositol polyphosphate and phosphoinositide pathways described below.

It has recently been shown that certain inositol phosphate derivatives including D-myo-inositol 3,4,5,6-tetrakisphosphate ("Ins(3,4,5,6)$P_4$") (M. Vajanaphanich et al., Nature 371:711 (1994); J. M. Uribe et al., J. Biol. Chem. 271(43): 26588 (1996); M. T. Rudolf et al., J. Med. Chem. 41 (19): 3635-3644 (1998)), and sn-di-O-palmitoylD,L-6-O-butyryl-phosphatidylinositol 3,4,5-trisphosphate heptakis (acetoxymethyl)ester (C. Schultz et al., Membrane-permeant, Bioactivatable Derivatives of Inositol Polyphosphates and Phosphoinositides, in Phosphoinositides. Chemistry, Biochemistry and Biomedical Applications, K. S. Bruzik, Ed. Am. Chem. Soc., Symp. Ser., 718, 232-243 (1999)) inhibit calcium-mediated chloride secretion. D-myo-Inositol 1,4,5,6-tetrakisphosphate has been shown to inhibit a phosphatidylinositol PI-3 kinase ("PI-3 kinase") signaling pathway in colonic epithelia (Eckmarn et al., Proc. Natl. Acad. Sci. USA 94:14456 (1997)). It has also recently been shown that 2,6-di-O-butyryl-myo-inositol 1,2,4,5-octakis (acetoxymethyl)ester increased the level of $Ca^{2+}$ in PC12 cells (C. Schultz et al. (1998), supra). U.S. Pat. No. 5,693,521 to Tsien et al. discloses the use of D-2,3-di-O-butyryl-myo-inositol 1,4,5,6-tetrakisphosphate octakis(acetoxy-methyl) ester as a second messenger having enhanced cell permeability. International Publication No. WO 98/11901 by Traynor-Kaplan et al. describes various inositol phosphates with enhanced cell permeability that function as either agonists or antagonists of inositol polyphosphates. In addition, the synthesis of other inositol phosphates has been reported (S. Roemer et al., J. Chem. Soc.; Perkin Trans. 1, 1683 (1996); International Publication No. WO 96/40695 to Tsien et al.; International Publication No. WO 98/11901 to A. Traynor-Kaplan et al.; Rudolf, M. T. et al., Bioorg. & Med. Chem. Lett., 8:1857 (1998); Jiang, T. et al., J. Biol. Chem. 273:11017 (1998); Li, W., et al., Tetrahedron 53:12017 (1997)).

Inflammation also plays a role in cystic fibrosis and other disorders. Inflammation is the body's response to injury and has been defined as a localized protective response to destroy, dilute or sequester the injurious agent and/or injured tissue. Classic macroscopic signs include pain, heat, redness, swelling and loss of function. On a microscopic level there is a dilatation of blood vessels with accompanying increased permeability and blood flow, exudation of fluids and infiltration of leucocytes. These responses are triggered by the release from the vascular system of inflammatory response mediators (e.g., histamine, prostaglandins, and leukotrienes) to destroy any bacteria or other toxins in the injured area and remove necrotic tissue. If this inflammatory response is somehow inappropriately triggered, toxic substances (i.e., reactive oxygen species-free radicals) that are associated with the inflammatory response mediators can destroy healthy tissues. A number of diseases such as asthma, osteoarthritis, rheumatoid arthritis, inflammatory bowel disease and adult respiratory distress syndrome (ARDS) result from such a faulty inflammatory response. In addition, consequences of acute inflammation result in irreparable tissue damage following heart attacks and strokes. In these cases much of the tissue destruction is caused by caustic oxygen radicals and their byproducts. It is now recognized that excessive release of oxygen radicals can lead to an overproduction of "wound healing" reactions such as release of growth factors that induce overproliferation of connective tissue and extracellular matrix components that can result in fibrosis, sclerosis, adhesions and scarring. Current therapies for these conditions such as steroids are ameliorative and do not resolve the core problems and are generally immunosuppressive. In addition, the available medications lead to side effects that restrict their long-term use. Therefore, a need persists for safe and effective anti-inflammatory agents.

To the best of Applicants' knowledge, the novel inositol polyphosphate derivatives of the present invention and the use of inositol polyphosphate derivatives for treating cystic fibrosis have not been previously known.

SUMMARY OF THE INVENTION

It is known that certain inositol polyphosphates elevate intracellular calcium levels, thus leading to increased chloride secretion. In one aspect, the present invention provides novel compounds, useful for regulating chloride secretion and/or inhibiting inflammation, having the general formula (I):

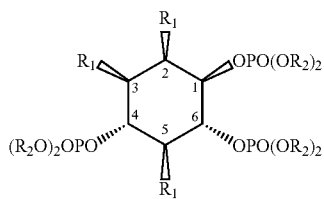

wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups;

and the racemates, diastereomers and pharmaceutically acceptable salts thereof.

The present invention further provides compositions, useful for regulating chloride secretion and/or inhibiting inflammation, comprising a therapeutically effective amount of compounds of formula (I) or a racemate thereof, and pharmaceutically acceptable salts thereof, together with a pharmaceutically acceptable carrier or vehicle.

The invention further provides methods for regulating chloride secretion and/or inhibiting inflammation in a cell or tissue with an effective amount of a compound of formula (I), or regulating chloride secretion and/or inhibiting inflammation in a human or animal patient comprising administering to a patient in need of such increased chloride secretion a therapeutically effective amount of a compound of formula (I), or a racemate thereof, or a pharmaceutically acceptable salt thereof, wherein:

each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —O$C_1$-$C_6$ allyl, and OC(O)$C_1$-$C_6$ all groups, including racemates and diastereomers thereof.

In a preferred embodiment, the present methods comprise contacting a cell or tissue with a compound of formula (I) selected from the group consisting of D-2,3,5-tri-O-butyryl-myo-inositol 1,4,6-trisphosphate hexakis(acetoxymethyl)ester, D-2,3,5-tri-O-butyryl-myo-inositol 1,4,6-trisphosphate hexakis(propionoxymethyl) ester, and a racemate or pharmaceutically acceptable salt thereof.

In one embodiment of the invention, the compound of formula (I) is administered in a composition comprising a pharmaceutically acceptable carrier or vehicle. Such carrier or vehicle can include a liposomal formulation or a formulation in an aerosol.

The present invention still further provides novel compounds, useful for regulating chloride secretion and/or inhibiting inflammation, having the general formula (II):

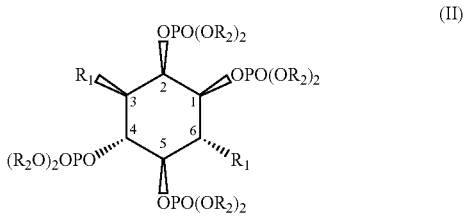

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof, with the proviso that the compound of formula (II) is not D-3,6-Di-O-butyryl-myo-inositol 1,2,4,5-tetrakisphosphate octakis(acetoxymethyl) ester; D-1,4-Di-O-butyryl-myo-inositol 2,3,5,6-tetrakisphosphate octakis(acetoxymethyl)ester or a racemate thereof.

The present invention further provides compositions, useful for regulating chloride secretion and/or inhibiting inflammation, comprising a therapeutically effective amount of compounds of formula (II) or a racemate thereof and pharmaceutically acceptable salts thereof, with the proviso that the compound of formula (II) is not D-3,6-Di-O-butyryl-myo-inositol 1,2,4,5-tetrakisphosphate octakis(acetoxymethyl)ester, D-1,4-Di-O-butyryl-myo-inositol 2,3,5,6-tetrakisphosphate octakis(acetoxymethyl)ester, or a racemate thereof. Such compositions can also comprise a pharmaceutically acceptable carrier or vehicle.

The invention further provides methods for regulating chloride secretion and/or inhibiting inflammation in a cell or tissue with an effective amount of a compound of formula (II), or regulating chloride secretion and/or inhibiting inflammation in a human or animal patient comprising administering to a patient in need of such increased chloride secretion a therapeutically effective amount of a compound of formula (II), or a racemate thereof, or a pharmaceutically acceptable salt thereof, wherein:

each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain allyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, —$NO_2$, —O$C_1$-$C_6$ alkyl, and OC(O)$C_1$-$C_6$ alkyl groups, including racemates and diastereomers thereof. In one embodiment of the invention, the compound of formula (II) is administered in a composition comprising a pharmaceutically acceptable carrier or vehicle. Such carrier or vehicle can include a liposomal formulation or a formulation in an aerosol.

In a preferred embodiment, the present methods comprise contacting a cell or tissue with a compound of formula (II) selected from the group consisting of D-3,6-di-O-butyryl-myo-inositol 1,2,4,5-tetrakisphosphate octakis(propionoxymethyl)ester; D-1,4-di-O-butyryl-myo-inositol 2,3,5,6-tetrakisphosphate octakis(propionoxymethyl)ester and a racemate or a pharmaceutically acceptable salt thereof.

In one embodiment of the invention, the compound of formula (II) is administered in a composition comprising a pharmaceutically acceptable carrier or vehicle. Such carrier or vehicle can include a liposomal formulation or a formulation in an aerosol.

In other embodiments, it has now been discovered that certain inositol polyphosphate derivatives act as antagonists of Ins(3,4,5,6)$P_4$ and Ins(1,4,6)$P_3$, and that the Ins(3,4,5,6)$P_4$ antagonists can be used to activate chloride secretion, when desired, such as in the treatment of cystic fibrosis. The present invention still further provides novel compounds, useful for regulating chloride secretion and/or inhibiting inflammation, having the general formula (III):

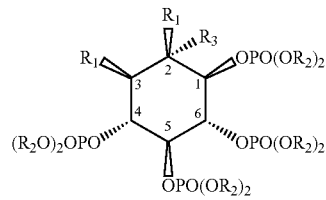

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight- or branched chain alkenyl or alkynyl, —OC(O)$C_1$-$C_{20}$ straight or branched chain alkyl and —O$C_1$-$C_{20}$ straight or branched chain alkyl, —O$C_2$-$C_{20}$ straight or branched chain alkenyl or alkynyl, and —OPO(O$R_2$)$_2$; or each $R_1$ may be taken together to form a cyclic structure;

each $R_2$ is independently selected from a group consisting of hydrogen and —C($R_4$)($R_4$)OC(O)$C_1$-$C_4$ straight or branched chain alkyl; and each $R_3$ is independently selected from a group consisting of —$C_1$-$C_{20}$ straight or branched chain alkyl, —$C_2$-$C_{20}$ straight or branched chain alkenyl or alkynyl, —$C_1$-$C_{11}$—X—Y, where each X is independently selected from a group consisting of —O—, —S—, —Se—, —CO(O)—, —CS(O)—, —CO(S)—, —OC(O)—, —SC(O)—, OC(S)—, or —NH—, and where Y is independently selected from a group consisting of —$C_1$-$C_{11}$ straight or branched chain allyl, —$C_2$-$C_{12}$ straight or branched chain alkenyl or alkynyl, or unsubstituted and substituted benzyl, and phenyl, including racemates and diastereomers thereof each $R_4$ is independently selected from a group consisting of hydrogen and —$C_1$-$C_{12}$ alkyl, both $R_4$ taken as a 5- or 6-membered ring, phenyl, and benzyl, said $R_4$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof.

The present invention further provides compositions, useful for regulating chloride secretion and/or inhibiting inflammation, comprising a therapeutically effective amount of compounds of formula (II) or a racemate thereof, and pharmaceutically acceptable salts thereof. Such compositions can also comprise a pharmaceutically acceptable carrier or vehicle.

The invention further provides methods for regulating chloride secretion and/or inhibiting inflammation in a cell or tissue with an effective amount of a compound of formula (III), or regulating chloride secretion and/or inhibiting inflammation in a human or animal patient comprising administering to a patient in need of such increased chloride secretion a therapeutically effective amount of a compound of formula (III), or a racemate thereof, or a pharmaceutically acceptable salt thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, —O$C_2$-$C_{20}$ straight or branched chain alkenyl or alkynyl, and —OPO(O$R_2$)$_2$; or each $R_1$ may be taken together to form a cyclic structure;

each $R_2$ is independently selected from a group consisting of hydrogen and —C($R_4$)($R_4$)OC(O)$C_1$-$C_4$ straight or branched chain alkyl; and each $R_3$ is independently selected from a group consisting of —$C_1$-$C_{20}$ straight or branched chain alkyl, —$C_2$-$C_{20}$ straight or branched chain alkenyl or alkynyl, —$C_1$-$C_{11}$—X—Y, where each X is independently selected from a group consisting of —O—, —S—, —Se—, —CO(O)—, —CS(O)—, —CO(S)—, —OC(O)—, —SC(O)—, OC(S)—, or —NH—, and where Y is independently selected from a group consisting of —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof.

each $R_4$ is independently selected from a group consisting of hydrogen and —$C_1$-$C_{12}$ alkyl, both $R_4$ taken as a 5- or 6-membered ring, phenyl, and benzyl, said $R_4$, except hydrogen, being unsubstituted or substituted with one or more halogen, OH, $C_1$-$C_6$ alkyl, $NO_2$, —$OC_1$-$C_6$ alkyl, and OC(O)$C_1$-$C_6$ alkyl groups, including racemates and diastereomers thereof. In one embodiment of the invention, the compound of formula (III) is administered in a composition comprising a pharmaceutically acceptable carrier or vehicle. Such carrier or vehicle can include a liposomal formulation or a formulation in an aerosol.

In a preferred embodiment, the present methods comprise contacting a cell or tissue with a compound of formula (III) selected from the group consisting of rac-(3aS, 4R, 5S, 6R, 7S, 7aS)4,5,6,7-tetrakis[[bis(acetoxymethoxy)phosphoryl]oxy]-2,2-dimethyl-3a-propyl-hexahydrobenzo-(1,3)-dioxol; rac-(1S, 2R, 3S, 4R, 5S, 6S)-4,5,6,7-tetrakis[[bis(acetoxymethoxy)phosphoryl]oxy]-1-butyroxy-6-propoxy-1-propyl-cyclohexane; rac-(1S, 2R, 3S, 4R, 5S, 6S)-2,3,4,5,6-pentakis-[[Dis(acetoxy-methoxy)phosphoryl]oxy]-6-butyroxy-2-propyl-cyclohexane; or a racemate or a pharmaceutically acceptable salt thereof.

The present invention still further provides novel compounds, useful for regulating chloride secretion and/or inhibiting inflammation, having the general formula (IV):

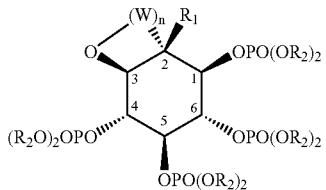

(IV)

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —$OC_1$-$C_{20}$ straight or branched chain alkyl, —$OC_2$-$C_{20}$ straight or branched chain alkenyl or alkynyl, and —OPO(O$R_2$)$_2$;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —$OC_1$-$C_6$ alkyl, and OC(O)$C_1$-$C_6$ alkyl groups, including racemates and diastereomers thereof; and each W is independently selected from a group consisting of —C(X)(Y)—, —C(X)(Y)—C(X)(Y)—, or —C(X)(Y)—C(X)(Y)—C(X)(Y)— and where X and Y are independently selected from a group consisting of hydrogen, —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof and hydrogen, —OH, —Oalkyl, —SH, —Salkyl, —CO(O)alkyl, —CS(O)alkyl, —CO(S)alkyl, —OC(O)alkyl, —SC(O)alkyl, —OC(S)alkyl, or —CONH$_2$, or —CONHalkyl, or —CON(alkyl)(alkyl), —NH$_2$, and where n is an integer from 2 to 13, preferably 2 to 5.

The present invention further provides compositions, useful for regulating chloride secretion and/or inhibiting inflammation, comprising a therapeutically effective amount of compounds of formula (IV) or a racemate thereof, and pharmaceutically acceptable salts thereof. Such compositions can also comprise a pharmaceutically acceptable carrier or vehicle.

The invention further provides, methods for regulating chloride secretion and/or inhibiting inflammation in a cell or tissue with an effective amount of a compound of formula (IV), or regulating chloride secretion and/or inhibiting inflammation in a human or animal patient in need of such increased chloride secretion a therapeutically effective amount of a compound of formula (IV), and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —$OC_1$-$C_{20}$ straight or branched chain alkyl, —$OC_2$-$C_{20}$ straight or branched chain alkenyl or alkynyl, and —OPO(O$R_2$)$_2$;

each $R_2$ is independently selected from a group consisting of hydrogen and —C($R_3$)($R_3$)OC(O)$C_1$-$C_4$ straight or branched allyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, —OH, —$C_1$-$C_6$ alkyl, —$NO_2$, —$OC_1$-$C_6$ alkyl, and —OC(O)$C_1$-$C_6$ alkyl groups, including racemates and diastereomers thereof; and each W is independently selected from a group consisting of —C(X)(Y)—, —C(X)(Y)—C(X)(Y)—, or —C(X)(Y)—C(X)(Y)—C(X)(Y)— and where X and Y are independently selected from a group consisting of hydrogen, —$C_1$-$C_{11}$ straight or branched chain alkyl, —$C_2$-$C_{12}$ straight or branched chain alkenyl or alkynyl, or unsubstituted and substituted benzyl, and phenyl, including racemnates and diastereomers thereof and hydrogen, —OH, —Oalkyl, —SH, —Salkyl, —CO(O)alkyl, —CS(O)alkyl, —CO(S)alkyl, —OC(O)alkyl, —SC(O)alkyl, —OC(S)alkyl, or —CONH$_2$, or —CONHalkyl, or —CON(alkyl)(alkyl), —NH$_2$, and where n is an integer from 2 to 13, preferably 2 to 5.

In one embodiment of the invention, the compound of formula (IV) is administered in a composition comprising a pharmaceutically acceptable carrier or vehicle. Such carrier or vehicle can include a liposomal formulation or a formulation in an aerosol.

In a preferred embodiment, the present methods comprise contacting a cell or tissue with a compound of formula (IV) selected from the group consisting of D-2-O-butyryl-1,2,4,5, 6-pentahydrobenzoxirane 1,4,5,6-tetrakisphosphate octakis-(acetoxymethyl) ester, D-2-O-butyryl-2,3,4,5,6-pentahydrobenzoxirane 3,4,5,6-tetra-kisphosphate octakis (acetoxymethyl)ester; D-2-O-butyryl-1,2,4,5,6-pentahydrochroman 1,4,5,6-tetrakisphosphate octakis (acetoxymethyl)ester; D-2-O-butyryl-2,3,4,5,6-pentahydrochroman 3,4,5,6-tetrakisphosphate octakis (acetoxymethyl)ester; or a racemate or a pharmaceutically acceptable salt thereof.

The present invention still further provides novel compounds, useful for regulating chloride secretion and/or inhibiting inflammation, having the general formula (V):

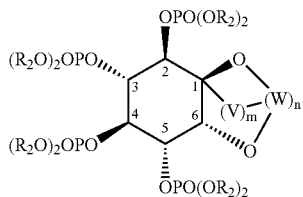

(V)

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain allyl and —O$C_1$-$C_{20}$ straight or branched chain alkyl, —O$C_2$-$C_{20}$ straight or branched chain alkenyl or alkynyl, and —OPO(O$R_2$)$_2$;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, —OH, $C_1$-$C_6$ alkyl, —NO$_2$, —O$C_1$-$C_6$ alkyl, and —OC(O)$C_1$-$C_6$ alkyl groups, including racemates and diastereomers thereof; and each V is independently selected from a group consisting of —C(X —C(X)(Y)—C(X)(Y)—, or —C(X)(Y)—C (X)(Y)—C(X)(Y)—; and m is an integer from 2 to 15, preferably from 2 to 5; and each W is independently selected from a group consisting of —C(X)—, —C(X)—C(X)(Y)—, or —C(X)—C(X) (Y)—C(X)(Y)—; and n is an integer from 1 to 15, preferably from 1 to 3; and X and Y are independently selected from a group consisting of hydrogen, —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof and hydrogen, —OH, —Oalkyl, —SH, —Salkyl, —CO(O)alkyl, —CS(O)alkyl, —CO(S)alkyl, —OC(O)alkyl, —SC(O)alkyl, —OC(S)alkyl, or —CONH$_2$, or —CONHalkyl, or —CON(alkyl)(alkyl), —NH$_2$.

The present invention further provides compositions, useful for regulating chloride secretion and/or inhibiting inflammation, comprising a therapeutically effective amount of compounds of formula (V) or a racemate thereof, and pharmaceutically acceptable salts thereof. Such compositions can also comprise a pharmaceutically acceptable carrier or vehicle.

The invention further provides methods for regulating chloride secretion and/or inhibiting inflammation in a cell or tissue with an effective amount of a compound of formula (V), or regulating chloride secretion and/or inhibiting inflammation in a human or animal patient in need of such increased chloride secretion using a therapeutically effective amount of a compound of formula (V), and racemates, stereoisomers and pharmaceutically acceptable salts thereof.

In one embodiment of the invention, the compound of formula (V) is administered in a composition comprising a pharmaceutically acceptable carrier or vehicle. Such carrier or vehicle can include a liposomal formulation or a formulation in an aerosol.

In a preferred embodiment, the present methods comprise contacting a cell or tissue with a compound of formula (V) selected from the group consisting of (1S, 2R, 3S, 4R, 5S, 6S, 8R)-2,3;4,5-tetrakis[[is(acetoxymethoxy)phosphoryl]oxy]-7,12-dioxa-tricyclo-[6.3.1.0$^{1,6}$]-dodecane; or a racemate or a pharmaceutically acceptable salt thereof.

The compounds of formulas (I), (II), (III), (IV) and (V) may be administered by a variety of methods including orally, sublingually, intranasally, intramuscularly, intravenously, subcutaneously, intravaginally, transdermally, rectally, by inhalation, or as a mouthwash.

The present invention may be understood more fully by reference to the following figures, detailed description and illustrative examples which are intended to exemplify non-limiting embodiments of the invention.

DETAILED DESCRIPTION OF THE PREFERRED EMBODIMENT

Figure 1:
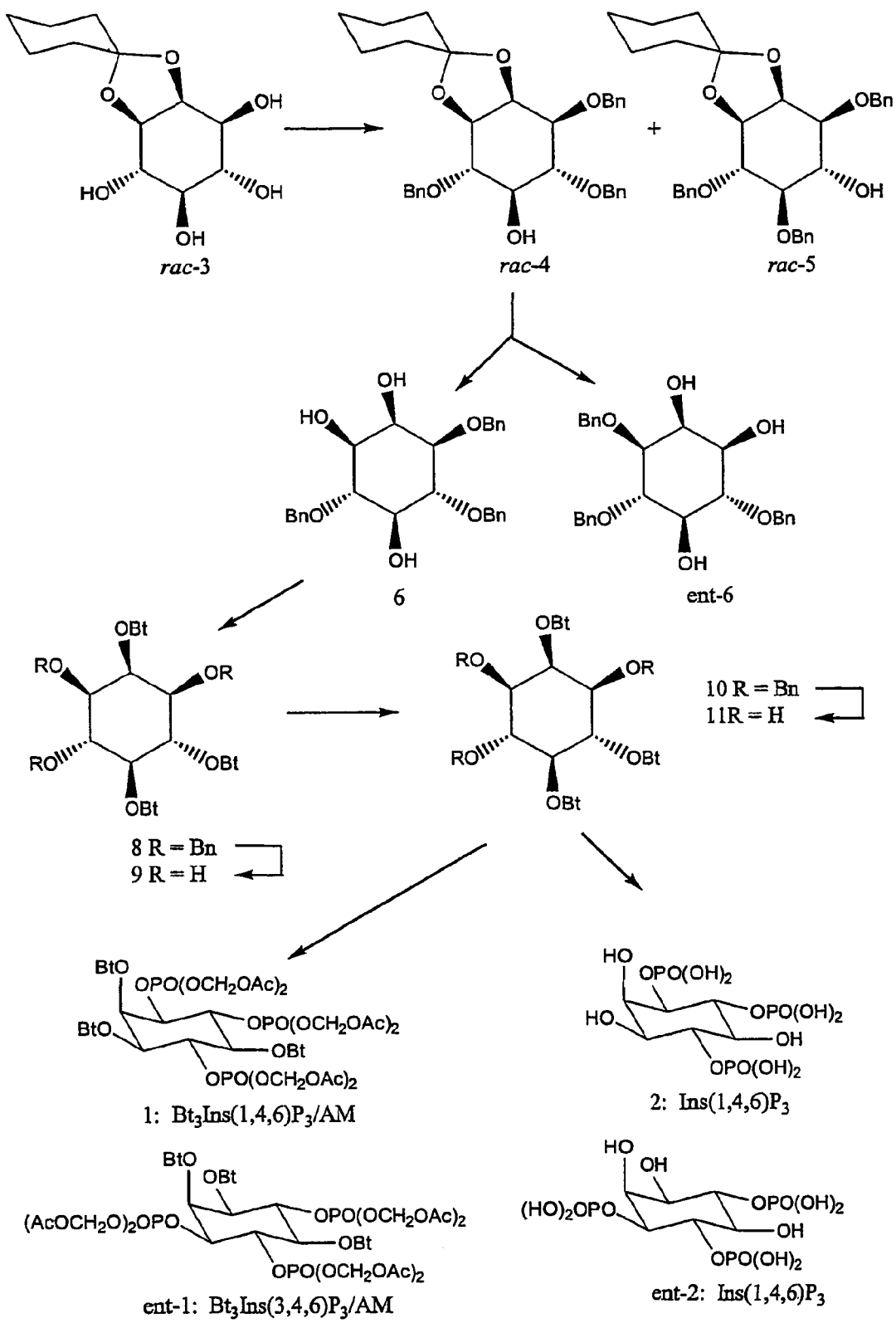
FIG. 1 is a reaction scheme showing a representative route for the synthesis of 2,3,5-tri-O-butyryl-myo-inositol 1,4,6-trisphosphate hexakis(proprioxymethyl)ester (also referred to herein as "TMX"), as described in Example 1.

In accordance with the present invention, novel compounds and methods useful for regulating chloride secretion and/or inhibiting inflammation of epithelial cells are provided. In one aspect of the invention, the novel compounds have the general formula (I):

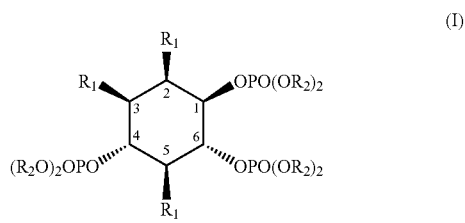

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof.

The present invention further provides compositions, useful for modulating chloride secretion, comprising a therapeutically effective amount of compounds of formula (I) or a racemate thereof, and pharmaceutically acceptable salts thereof. As used herein, the terms "modulating chloride secretion" and "regulating chloride secretion" are used in relationship to compounds of the invention that enhance or activate chloride secretion from treated cells or tissues, as well as compounds that inhibit chloride secretion from treated cells or tissues. The actual in vivo activity of a compound of the invention in the modulation of chloride secretion may be reliably predicted by the chloride secretion assays disclosed herein, such as the assays of Examples 8 and 9, as well as other chloride secretion assays well known to those skilled in the art. In one aspect of the present invention, presently preferred compounds of the invention represented by formulas (I)-(V) are effective for activating or enhancing chloride secretion in cells or tissues treated with the compounds.

Such compositions can also comprise a pharmaceutically acceptable carrier or vehicle.

The invention further provides methods for regulating chloride secretion, comprising administering to a patient in need of such increased or decreased chloride secretion a therapeutically effective amount of a compound of formula (I), or a racemate thereof, or a pharmaceutically acceptable salt thereof, wherein:

each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof.

In one embodiment of the invention, the compound of formula (I) is administered in a composition comprising a pharmaceutically acceptable carrier or vehicle. Such carrier or vehicle can include a liposomal formulation or a formulation in an aerosol.

The invention further provides methods for regulating chloride secretion in a cell or tissue with an effective amount of a compound of formula (I) or a racemate thereof, or a pharmaceutically acceptable salt thereof, wherein:

each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof.

In a preferred embodiment, the present methods comprise contacting a cell or tissue with a compound of formula (I) selected from the group consisting of D-2,3,5-tri-O-butyryl-myo-inositol 1,4,6-trisphosphate hexakis(acetoxymethyl)ester; D-2,3,5-tri-O-butyryl-myo-inositol 1,4,6-trisphosphate hexakis(propionoxymethyl) ester, or a racemate thereof, or a pharmaceutically acceptable salt thereof.

In one embodiment of the invention, the compound of formula (I) is administered in a composition comprising a pharmaceutically acceptable carrier or vehicle. Such carrier or vehicle can include a liposomal formulation or a formulation in an aerosol.

The present invention still further provides novel compounds, useful for stimulating chloride secretion of epithelial cells are provided, having the general formula (II):

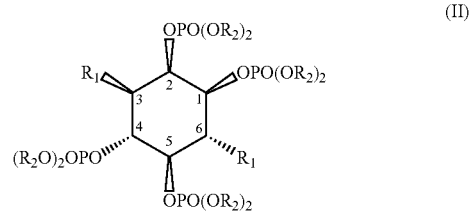

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof with the proviso that the compound of formula (II) is not D-3,6-di-O-butyryl-myo-inositol 1,2,4,5-tetrakisphosphate octakis(acetoxymethyl) ester, D-1,4-di-O-butyryl-myo-inositol 2,3,5,6-tetrakisphosphate octakis(acetoxymethyl)ester or a racemate thereof.

The present invention further provides compositions, useful for regulating chloride secretion, comprising a therapeutically effective amount of compounds of formula (II) or a racemate thereof, and pharmaceutically acceptable salts thereof, with the proviso that the compound of formula (II) is not D-3,6-di-O-butyryl-myo-inositol 1,2,4,5-tetrakisphosphate octakis(acetoxymethyl) ester; D-1,4-di-O-butyryl-myo-inositol 2,3,5,6-tetrakisphosphate octakis(acetoxymethyl)ester or a racemate thereof.

Such compositions can also comprise a pharmaceutically acceptable carrier or vehicle.

The invention further provides methods for regulating chloride secretion, comprising administering to, a patient in need of such modified chloride secretion a therapeutically effective amount of a compound of formula (II), or a racemate thereof, or a pharmaceutically acceptable salt thereof, wherein:

each $R_1$ is independently selected from the groups consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, and —O$C_2$-$C_{20}$ straight or branched chain alkenyl or alkynyl;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —$OC_1$-$C_6$ alkyl, and $OC(O)C_1$-$C_6$ alkyl groups, including racemates and diastereomers thereof.

In one embodiment of the invention, the compound of formula (II) is administered in a composition comprising a pharmaceutically acceptable carrier or vehicle. Such carrier or vehicle can include a liposomal formulation or a formulation in an aerosol.

The invention further provides methods for regulating chloride secretion in a cell or tissue with an effective amount of a compound of formula (II) or a racemate thereof, or a pharmaceutically acceptable salt thereof, wherein:

each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —$OC(O)C_1$-$C_{20}$ straight or branched chain alkyl and —$OC_1$-$C_{20}$ straight or branched chain alkyl, and —$OC_2$-$C_{20}$ straight or branched chain alkenyl or alkynyl;

each $R_2$ is independently selected from a group consisting of hydrogen and —$C(R_3)(R_3)OC(O)C_1$-$C_4$ straight or branched chain alkyl; and each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, OH, $C_1$-$C_6$ alkyl, $NO_2$, —$OC_1$-$C_6$ alkyl, and $OC(O)C_1$-$C_6$ alkyl groups, including racemates and diastereomers thereof In a preferred embodiment, the present methods comprise contacting a cell or tissue with a compound of formula (II) selected from the group consisting of D-3,6-di-O-butyryl-myo-inositol 1,2,4,5-tetrakisphosphate octakis(propionoxymethyl) ester; D-1,4-di-O-butyryl-myo-inositol 2,3,5,6-tetrakisphosphate octakis-(propionoxymethyl) ester or a racemate or a pharmaceutically acceptable salt thereof.

In one embodiment of the invention, the compound of formula (II) is administered in a composition comprising a pharmaceutically acceptable carrier or vehicle. Such carrier or vehicle can include a liposomal formulation or a formulation in an aerosol.

The present invention still further provides novel compounds, useful for stimulating chloride secretion of epithelial cells are provided, having the general formula (III):

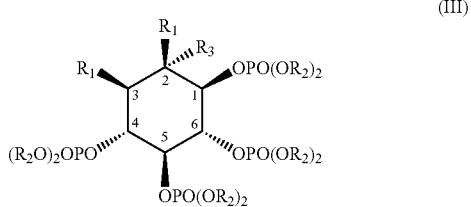

(III)

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —$OC(O)C_1$-$C_{20}$ straight or branched chain alkyl and —$OC_1$-$C_{20}$ straight or branched chain alkyl, —$OC_2$-$C_{20}$ straight or branched chain alkenyl or alkynyl, and —$OPO(OR_2)_2$; or each $R_1$ may be taken together to form a cyclic structure;

each $R_2$ is independently selected from a group consisting of hydrogen and —$C(R_4)R_4)OC(O)C_1$-$C_4$ straight or branched chain alkyl; and each $R_3$ is independently selected from a group consisting of —$C_1$-$C_{20}$ straight or branched chain alkyl, —$C_2$-$C_{20}$ straight or branched chain alkenyl or alkynyl, —$C_1$-$C_{11}$—X—Y, where each X is independently selected from a group consisting of —O—, —S—, —Se—, —CO(O)—, —CS(O)—, —CO(S)—, —OC(O)—, —SC(O)—, OC(S)—, or —NH—, and where Y is independently selected from a group consisting of —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof each $R_4$ is independently selected from a group consisting of hydrogen and —$C_1$-$C_{12}$ alkyl, both $R_4$ taken as a 5- or 6-membered ring, phenyl, and benzyl, said $R_4$, except hydrogen, being unsubstituted or substituted with one or more halogen, OH, $C_1$-$C_6$ alkyl, $NO_2$, —$OC_1$-$C_6$ alkyl, and $OC(O)C_1$-$C_6$ alkyl groups, including racemates and diastereomers thereof.

The present invention further provides compositions, useful for regulating chloride secretion, comprising a therapeutically effective amount of compounds of formula (III) or a racemate thereof, and pharmaceutically acceptable salts thereof.

Such compositions can also comprise a pharmaceutically acceptable carrier or vehicle.

The invention further provides methods for regulating chloride secretion, comprising administering to a patient in need of such modified chloride secretion a therapeutically effective amount of a compound of formula (III), or a racemate thereof, or a pharmaceutically acceptable salt thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —$OC(O)C_1$-$C_{20}$ straight or branched chain alkyl and —$OC_1$-$C_{20}$ straight or branched chain alkyl, —$OC_2$-$C_{20}$ straight or branched chain alkenyl or alkynyl, and —$OPO(OR_2)_2$; or each $R_1$ may be taken together to form a cyclic structure;

each $R_2$ is independently selected from a group consisting of hydrogen and —$C(R_4)(_4)OC(O)C_1$-$C_4$ straight or branched chain alkyl; and each $R_3$ is independently selected from a group consisting of —$C_1$-$C_{20}$ straight or branched chain alkyl, —$C_2$-$C_{20}$ straight or branched chain alkenyl or alkynyl, —$C_1$-$C_{11}$—X—Y, where each X is independently selected from a group consisting of —O—, —S—, —Se—, —CO(O)—, —CS(O)—, —CO(S)—, —OC(O)—, —SC(O)—, OC(S)—, or —NH—, and where Y is independently selected from a group consisting of —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof.

each $R_4$ is independently selected from a group consisting of hydrogen and —$C_1$-$C_{12}$ alkyl, both $R_4$ taken as a 5- or 6-membered ring, phenyl, and benzyl, said $R_4$, except hydrogen, being unsubstituted or substituted with one or more halogen, OH, $C_1$-$C_6$ alkyl, $NO_2$, —$OC_1$-$C_6$ alkyl, and $OC(O)C_1$-$C_6$ alkyl groups, including racemates and diastereomers thereof.

Such compositions can also comprise a pharmaceutically acceptable carrier or vehicle.

The invention further provides methods for regulating chloride secretion, comprising administering to a patient in need of such modulated chloride secretion a therapeutically effective amount of a compound of formula (III), or a racemate thereof, or a pharmaceutically acceptable salt thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, —O$C_2$-$C_{20}$ straight or branched chain alkenyl or alkynyl, and —OPO(O$R_2$)$_2$; or each $R_1$ may be taken together to form a cyclic structure;

each $R_2$ is independently selected from a group consisting of hydrogen and —C($R_4$)($R_4$)OC(O)$C_1$-$C_4$ straight or branched chain alkyl; and each $R_3$ is independently selected from a group consisting of —$C_1$-$C_{20}$ straight or branched chain alkyl, —$C_2$-$C_{20}$ straight or branched chain alkenyl or alkynyl, —$C_1$-$C_{11}$—X—Y, where each X is independently selected from a group consisting of —O—, —S—, —Se—, —CO(O)—, —CS(O)—, —CO(S)—, —OC(O)—, —SC(O)—, OC(S)—, or —NH—, and where Y is independently selected from a group consisting of —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof.

each $R_4$ is independently selected from a group consisting of hydrogen and —$C_1$-$C_{12}$ alkyl, both $R_4$ taken as a 5- or 6-membered ring, phenyl, and benzyl, said $R_4$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof.

In one embodiment of the invention, the compound of formula (III) is administered in a composition comprising a pharmaceutically acceptable carrier or vehicle. Such carrier or vehicle can include a liposomal formulation or a formulation in an aerosol.

The invention further provides methods for regulating chloride secretion in a cell or tissue with an effective amount of a compound of formula (III) or a racemate thereof, or a pharmaceutically acceptable salt thereof wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain alkyl, —O$C_2$-$C_{20}$ straight- or branched chain alkenyl or alkynyl, and —OPO(O$R_2$)$_2$; or each $R_1$ may be taken together to form a cyclic structure;

each $R_2$ is independently selected from a group consisting of hydrogen and —C($R_4$)($R_4$)OC(O)$C_1$-$C_4$ straight or branched chain allyl; and each $R_3$ is independently selected from a group consisting of —$C_1$-$C_{20}$ straight or branched chain alkyl, —$C_2$-$C_{20}$ straight or branched chain alkenyl or alkynyl, —$C_1$-$C_{11}$—X—Y, where each X is independently selected from a group consisting of —O—, —S—, —Se—, —CO(O)—, —CS(O)—, —CO(S)—, —OC(O)—, —SC(O)—, OC(S)—, or —NH—, and where Y is independently selected from a group consisting of —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof.

each $R_4$ is independently selected from a group consisting of hydrogen and —$C_1$-$C_{12}$ alkyl, both $R^4$ taken as a 5- or 6-membered ring, phenyl, and benzyl, said $R^4$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$ alkyl groups, including racemates and diastereomers thereof.

In a preferred embodiment, the present methods comprise contacting a cell or tissue with a compound of formula (III) selected from the group consisting of D-2-O-butyryl-2-C-propyl-3-O-propyl-myo-inositol 1,4,5,6-tetrakisphosphate octakis(acetoxymethyl)ester; D-2-O-butyryl-2-C-propyl-1-O-propyl-myo-inositol 3,4,5,6-tetrakisphosphate octakis(acetoxymethyl)ester, D-2,3-O-isoproylidene-2-C-propyl-myo-inositol. 1,4,5,6-tetrakisphosphate octakis(acetoxymethyl) ester; D-1,2-O-isoproylidene-2-C-propyl-myo-inositol 3,4,5,6-tetrakisphosphate octakis-(acetoxymethyl) ester; or a racemate or a pharmaceutically acceptable salt thereof.

The present invention still further provides novel compounds, useful for stimulating chloride secretion of epithelial cells are provided, having the general formula (IV):

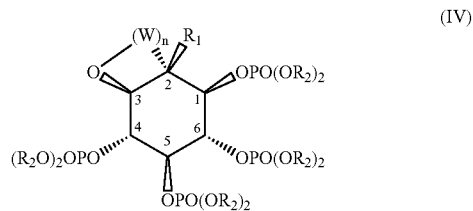

(IV)

and racemates pharmaceutically acceptable salts thereof, wherein each. $R_1$ is independently selected from the group consisting of hydrogen, —OH, —$C_1$-$C_{20}$ straight or branched chain alkyl, —$C_2$-$C_{20}$ straight or branched, chain alkenyl or alkynyl, —OC(O)$C_1$-$C_{20}$ straight or branched chain alkyl and —O$C_1$-$C_{20}$ straight or branched chain alkyl, —O$C_2$-$C_2$-$C_{20}$ straight or branched chain alkenyl or alkynyl, and —OPO(O$R_2$)$_2$;

each $R_2$ is independently selected from a group consisting of hydrogen and —C($R_3$)($R_3$)OC(O)$C_1$-$C_4$ straight or branched chain alkyl; and each $R_3$ is independently selected from a group consisting of hydrogen and —$C_1$-$C_{12}$ alkyl, both $R_4$ taken as a 5- or 6-membered ring, phenyl, and benzyl, said $R_4$, except hydrogen, being unsubstituted or substituted with one or more halogen, OH, $C_1$-$C_6$ alkyl, $NO_2$, —O$C_1$-$C_6$ alkyl, and OC(O)$C_1$-$C_6$' alkyl groups, including racemates and diastereomers thereof; and each W is independently selected from a group consisting of —C(X)(Y)—, —C(X)(Y)—C(X)(Y)—, or —C(X)(Y)—C(X)(Y)—C(X)(Y)— and where X and Y are independently selected from a group consisting of hydrogen, —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof and hydrogen, —OH, —Oalkyl, —SH, —Salkyl —CO(O)alkyl, —CS(O)alkyl, —CO(S)alkyl, —OC(O)alkyl, —SC(O)alkyl, —OC(S)alkyl, or —CONH$_2$, or —CONHalkyl, or —CON(alkyl)(alkyl), —NH$_2$, and where n is an integer from 2 to 13, preferably 2 to 5.

The present invention further provides compositions, useful for regulating chloride secretion, comprising a therapeutically effective amount of compounds of formula (I) or a racemate thereof, and pharmaceutically acceptable salts thereof. Such compositions can also comprise a pharmaceutically acceptable carrier or vehicle. The invention further provides methods for regulating chloride secretion, comprising administering to a patient in need of such modulated chloride secretion a therapeutically effective amount of a compound of formula (IV), and racemates, stereoisomers and pharmaceutically acceptable salts thereof, wherein each $R_1$ is independently selected from the group consisting of hydrogen, —OH, —C$_1$-C$_{20}$ straight or branched chain alkyl, —C$_2$-C$_{20}$ straight or branched chain alkenyl or alkynyl, —OC(O)C$_1$-C$_{20}$ straighter branched chain alkyl and —OC$_1$-C$_{20}$ straight or branched chain alkyl, —OC$_2$-C$_{20}$ straight or branched chain alkenyl or alkynyl, and —OPO(OR$_2$)$_2$;

each $R_2$ is independently selected from a group consisting of hydrogen and —C(R$_3$)(R$_3$)OC(O)C$_1$-C$_4$ straight or branched chain alkyl; and each $R_3$ is independently selected from a group consisting of hydrogen and. —C$_1$-C$_{12}$ alkyl, both R$_3$ taken as a 5- or 6-membered ring, phenyl, and benzyl, said R$_3$, except hydrogen, being unsubstituted or substituted with one or more halogen, OH, C$_1$-C$_6$ alkyl, NO$_2$, —OC$_1$-C$_6$ alkyl, and OC(O)C$_1$-C$_6$ alkyl groups, including racemates and diastereomers thereof; and each W is independently selected from a group consisting of —C(X)(Y)—, —C(X)(Y)—C(X)(Y)—, or —C(X)(Y)—C(X)(Y)—C(X)(Y)— and where X and Y are independently selected from a group consisting of hydrogen, —C$_1$-C$_{11}$ straight or branched chain alkyl, —C$_2$-C$_{12}$ straight or branched chain alkenyl or alkynyl, or unsubstituted and substituted benzyl, and phenyl, including racemates and diastereomers thereof and hydrogen, —OH, —Oalkyl, —SH, —Salkyl, —CO(O)alkyl, —CS(O)alkyl, —CO(S)alkyl, —OC(O)alkyl, —SC(O)alkyl, —OC(S)alkyl, or —CONH$_2$, or —CONHalkyl, or —CON(alkyl)(alkyl), —NH$_2$, and where n is an integer from 2 to 13, preferably 2 to 5.

Such compositions can also comprise a pharmaceutically acceptable carrier or vehicle.

The invention further provides methods for regulating chloride secretion, comprising administering to a patient in need of such modified chloride secretion a therapeutically effective amount of a compound of formula (IV), and racemates, stereoisomers and pharmaceutically acceptable salts thereof, wherein each $R_1$ is independently selected from the group consisting of hydrogen, —OH, —C$_1$-C$_{20}$ straight or branched chain alkyl, —C$_2$-C$_{20}$ straight or branched chain alkenyl or alkynyl, —OC(O)C$_1$-C$_{10}$ straight or branched chain alkyl and —OC$_1$-C$_{20}$ straight or branched chain alkyl, —OC$_2$-C$_{20}$ straight or branched chain alkenyl or alkynyl, and —OPO(OR$_2$)$_2$;

each $R_2$ is independently selected from a group consisting of hydrogen and —C(R$_3$)(R$_3$)OC(O)C$_1$-C$_4$ straight or branched chain alkyl; and each $R_3$ is independently selected from a group consisting of hydrogen and —C$_1$-C$_{12}$ alkyl, both R$_3$ taken as a 5- or 6-membered ring, phenyl, and benzyl, said R$_3$, except hydrogen, being unsubstituted or substituted with one or more halogen, OH, C$_1$-C$_6$ alkyl, NO$_2$, —OC$_1$-C$_6$ alkyl, and OC(O)C$_1$-C$_6$ alkyl groups, including racemates and diastereomers thereof; and each W is independently selected from a group consisting of —C(X)(Y)—, —C(X)(Y)—C(X)(Y)—, or —C(X)(Y)—C(X)(Y)—C(X)(Y)— and where X and Y are independently selected from a group consisting of hydrogen, —C$_1$-C$_{11}$ straight or branched chain alkyl, —C$_2$-C$_{12}$ straight or branched chain alkenyl or alkynyl, or unsubstituted and substituted benzyl, and phenyl, including racemates and diastereomers thereof and hydrogen, —OH, —Oalkyl, —SH, —Salkyl, —CO(O)alkyl, —CS(O)alkyl, —CO(S)alkyl, —OC(O)alkyl, —SC(O)alkyl, —OC(S)alkyl, or —CONH$_2$, or —CONHalkyl, or —CON(alkyl)(alkyl), —NH$_2$, and where n is an integer from 2 to 13, preferably 2 to 5.

In one embodiment of the invention, the compound of formula (IV) is administered in a composition comprising a pharmaceutically acceptable carrier or vehicle. Such carrier or vehicle can include a liposomal formulation or a formulation in an aerosol.

The invention further provides methods for regulating chloride secretion in a cell or tissue with an effective amount of a compound of formula (IV) or a racemate thereof, or a pharmaceutically acceptable salt thereof, wherein and racemates, stereoisomers and pharmaceutically acceptable salts thereof, wherein each $R_1$ is independently selected from the group consisting of hydrogen, —OH, —C$_1$-C$_{20}$ straight or branched chain alkyl, —C$_2$-C$_{20}$ straight or branched chain alkenyl or alkynyl, —OC(O)C$_1$-C$_{20}$ straight or branched chain alkyl and —OC$_1$-C$_{20}$ straight or branched chain alkyl, —OC$_2$-C$_{20}$ straight or branched chain alkenyl or alkynyl, and —OPO(OR$_2$)$_2$;

each $R_2$ is independently selected from a group consisting of hydrogen and —C(R$_3$)(R$_3$)OC(O)C$_1$-C$_4$ straight or branched chain alkyl; and each $R_3$ is independently selected from a group consisting of hydrogen and —C$_1$-C$_{12}$ alkyl, both R$_3$ taken as a 5- or 6-membered ring, phenyl, and benzyl, said R$_3$, except hydrogen, being unsubstituted or substituted with one or more halogen, OH, C$_1$-C$_6$ alkyl, NO$_2$, —OC$_1$-C$_6$ alkyl, and OC(O)C$_1$-C$_6$ alkyl groups, including racemates and diastereomers thereof; and each W is independently selected from a group consisting of —C(X)(Y)—, —C(X)(Y)—C(X)Y)—, or —C(X)(Y)—C(X)(Y)—CM)(Y)— and where X and Y are independently selected from a group consisting of hydrogen, —C$_1$-C$_{11}$ straight or branched chain alkyl, —C$_2$-C$_{12}$ straight or branched chain alkenyl or alkynyl, or unsubstituted and substituted benzyl, and phenyl, including racemates and diastereomers thereof and hydrogen, —OH, —Oalkyl, —SH, —Salkyl, —CO(O)alkyl, —CS(O)alkyl, —CO(S)allyl, —OC(O)alkyl, —SC(O)alkyl, —OC(S)alkyl, or —CONH$_2$, or —CONHalkyl, or —CON(alkyl)(alkyl), —NH$_2$, and where n is an integer from 2 to 13, preferably 2 to 5.

In a preferred embodiment, the present methods comprise contacting a cell or tissue with a compound of formula (IV) selected from the group consisting of D-2-O-butyryl-1,2,4,5,6-pentahydrobenzoxirane 1,4,5,6-tetrakisphosphate octakis(acetoxymethyl) ester, D-2-O-butyryl-2,3,4,5,6-pentahydrobenzoxirane 3,4,5,6-tetrakisphosphate octakis (acetoxymethyl)ester; D-2-O-butyryl-1,2,4,5,6-pentahydrochroman 1,4,5,6-tetrakisphosphate octakis (acetoxymethyl)ester; D-2-O-butyryl2,3,4,5,6-pentahydrochroman 3,4,5,6-tetrakisphosphate octakis-(acetoxymethyl) ester; or a racemate thereof, or a pharmaceutically acceptable salt thereof.

The present invention still further provides novel compounds, useful for stimulating chloride secretion of epithelial cells are provided, having the general formula (V):

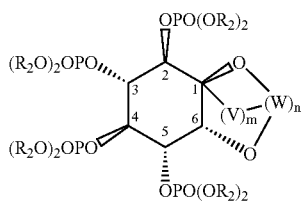

(V)

and racemates, stereoisomers and pharmaceutically acceptable salts thereof, wherein each $R_1$ is independently selected from the group consisting of hydrogen, —OH, —$C_1$-$C_{20}$ straight or branched chain alkyl, —$C_2$-$C_{20}$ straight or branched chain alkenyl or alkynyl, —OC(O)$C_1$-$C_{20}$ straight or branched chain alkyl and —O$C_1$-$C_{20}$ straight or branched chain allyl, —O$C_2$-$C_{20}$ straight or branched chain alkenyl or alkynyl, and —OPO(O$R_2$)$_2$;
 each $R_2$ is independently selected from a group consisting of hydrogen and —C($R_3$)($R_3$)OC(O)$C_1$-$C_4$ straight or branched chain alkyl; and
 each $R_3$ is independently selected from a group consisting of hydrogen and —$C_1$-$C_{12}$ alkyl, both $R_3$ taken as a 5- or 6-membered ring, phenyl, and benzyl, said $R_3$, except hydrogen, being unsubstituted or substituted with one or more halogen, —OH, $C_1$-$C_6$ allyl, —NO$_2$, —O$C_1$-$C_6$ alkyl, and —OC(O)$C_1$-$C_6$ allyl groups, including racemates and diastereomers thereof; and
 each V is independently selected from a group consisting of —C(X)(Y)—, —C(X(Y)—C(X)(Y)—, or —C(X)(Y)—C(X)(Y)—C(X)(Y)—; and
 m is an integer from 2 to 15, preferably from 2 to 5; and
 each W is independently selected from a group consisting of —C(X)—, —C(X)—C(X)(Y)—, or —C(X)—C(X)(Y)—C(X)(Y)—; and
 n is an integer from 1 to 15, preferably from 1 to 3; and
 X and Y are independently selected from a group consisting of hydrogen, —$C_1$-$C_{11}$ straight or branched chain alkyl, —$C_2$-$C_{12}$ straight or branched chain alkenyl or alkynyl, or unsubstituted and substituted benzyl, and phenyl, including racemates and diastereomers thereof and hydrogen, —OH, —Oalkyl, —SH, —Salkyl, —CO(O)alkyl, —CS(O)alkyl, —CO(S)alkyl, —OC(O)alkyl, —SC(O)alkyl, —OC(S)alkyl, or —CONH$_2$, or —CONHalkyl, or —CON(alkyl)(alkyl), —NH$_2$.

The present invention further provides compositions, useful for regulating chloride secretion and/or inhibiting inflammation, comprising a therapeutically effective amount of compounds of formula (V) or a racemate thereof, and pharmaceutically acceptable salts thereof.

Such compositions can also comprise a pharmaceutically acceptable carrier or vehicle.

The invention further provides methods for regulating chloride secretion, comprising administering to, a patient in need of such modified chloride secretion a therapeutically effective amount of a compound of formula (V), and racemates, stereoisomers and pharmaceutically acceptable salts thereof.

Such compositions can also comprise a pharmaceutically acceptable carrier or vehicle.

The invention further provides methods for regulating chloride secretion, comprising administering to a patient in need of such modified chloride secretion a therapeutically effective amount of a compound of formula (V), and racemates, stereoisomers and pharmaceutically acceptable salts thereof.

In one embodiment of the invention, the compound of formula (IV) is administered in a composition comprising a pharmaceutically acceptable carrier or vehicle. Such carrier or vehicle can include a liposomal formulation or a formulation in an aerosol.

The invention further provides methods for regulating chloride secretion in a cell or tissue with an effective amount of a compound of formula (V) or a racemate thereof, or a pharmaceutically acceptable salt thereof.

As used herein, the term "alkyl" as used herein refers to branched or straight chain alkyl groups comprising one to twenty carbon atoms ($C_1$-$C_{20}$) that are unsubstituted or substituted, e.g., with one or more halogen groups, including, e.g., methyl, ethyl, propyl, isopropyl, n-butyl, t-butyl, neopentyl, trifluoromethyl, pentafluoroethyl and the like.

The term "alkoxy" as used herein refers to RO— wherein R is alkyl as defined above. Representative examples of alkoxy groups include methoxy, ethoxy, t-butoxy, trifluoromethoxy and the like.

The term "alkenyl" as used herein refers to a branched or straight chain groups comprising two to twenty carbon atoms which also comprise one or more carbon-carbon double bonds. Representative alkenyl groups include 2-propenyl (i.e., allyl), 3-methyl-2-butenyl, 3,7-dimethyl-2,6-octadienyl, 4,8-dimethyl3,7-nonadienyl, 3,7,11-trimethyl-2,6,10-dodecatrienyl and the like.

The term "alkynyl" as used herein refers to a branched or straight chain comprising two to twenty carbon atoms that also comprises one or more carbon-carbon triple bonds. Representative alkynyl groups include ethynyl, 2-propynyl (propargyl), 1-propynyl and the like.

The term "halogen" or "halo" as used herein refers to iodo, bromo, chloro or fluoro.

The term "haloalkyl" as used herein refers to a lower alkyl radical, as defined above, bearing at least one halogen substituent, for example, chloromethyl, fluoro-ethyl or trifluoromethyl and the like.

In presently particularly preferred embodiments, the Ins(3,4,5,6)P$_4$ antagonists of the invention are designed to be delivered intracellularly, such as by concealing the negatively charged phosphate groups with bioactivatable esters, such as acetoxymethylesters (AM-esters), and the hydroxy groups with alkyl groups, such as butyrates, where necessary. These masking groups have previously been shown to permit passive diffusion of the inositol polyphosphate compounds across the plasma membrane to the interior of the cell where esterases cleave them and liberate the biologically active inositol polyphosphate inside the cell. (See M. Vajanaphanich et al., *Nature* 371:711 (1994); Rudolf, M. T. et al., "2-Deoxy derivative is a partial agonist of the intracellular messenger inositol 3,4,5,6-tetrakisphosphate in the epithelial cell line T84" *J Med Chem* 41:363544 (1998)).

Figure 5:
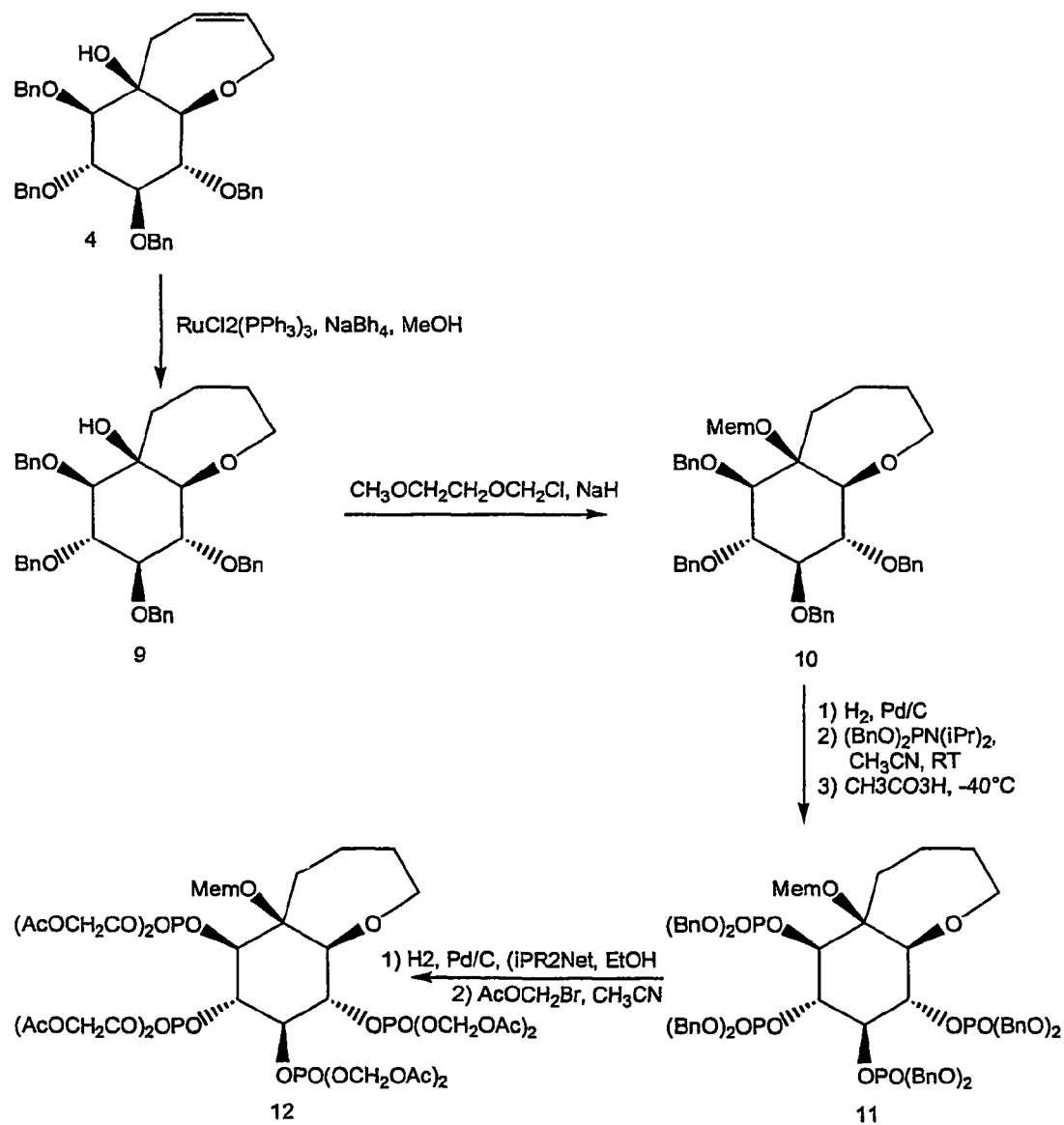
FIG. 5 is a reaction scheme showing a representative route for the synthesis of (5aα,6α,7β,8α,9β,9aα)-6,7,8,9-tetrakis [[bis(acetoxymethoxy)-phosphoryl]oxy]-5a-[(2'-methoxy) ethoxy]methoxy-decahydro-benzo[b]oxepin (also referred to herein as "Compound C"), as described in Example 5.
Figure 6:
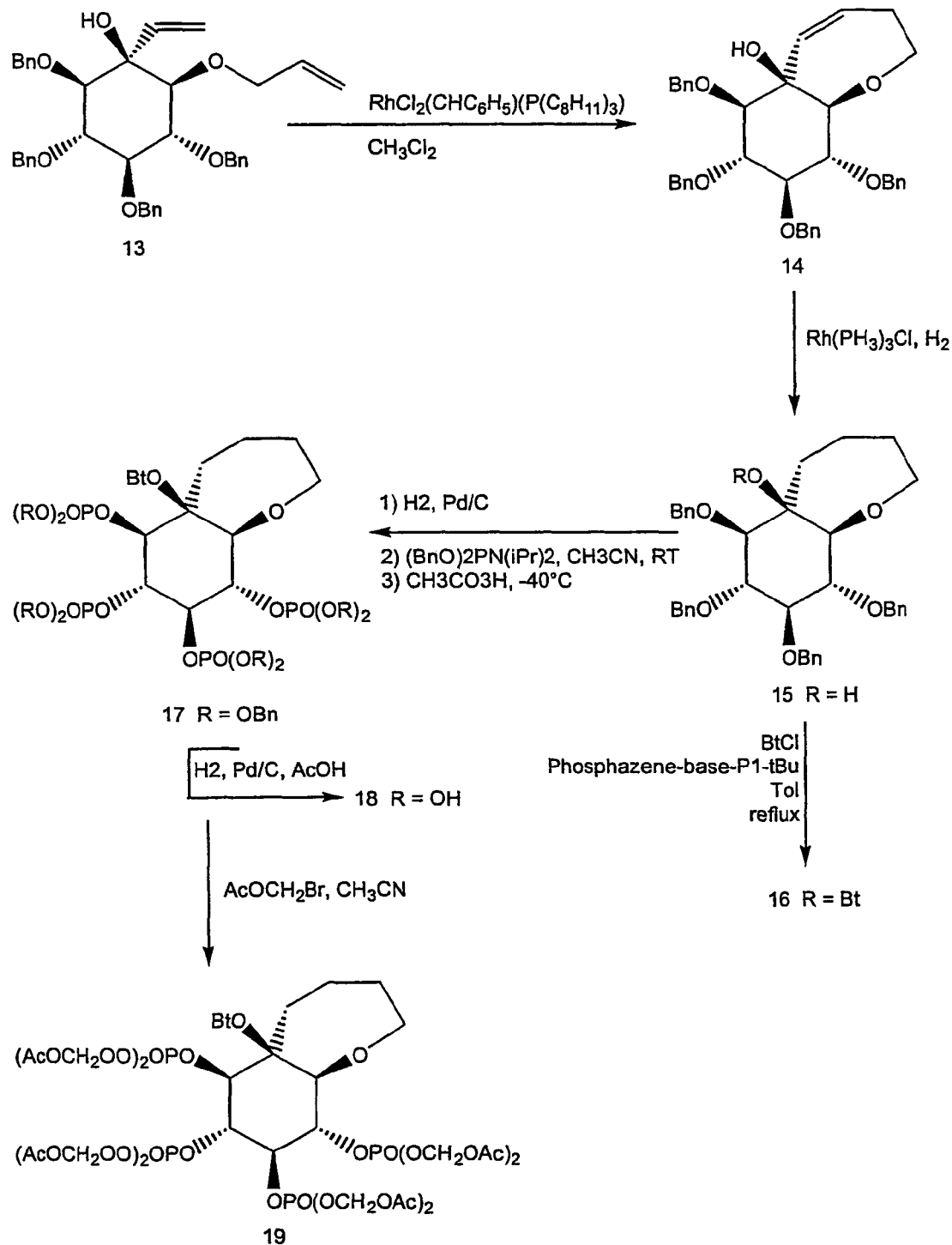
FIG. 6 is a reaction scheme showing a representative route for the synthesis of (4aα,6β,7α,8β,8aα)-5,6,7,8-tetrakis[[bis (acetoxymethoxy)-phosphoryl]oxy]4a-butyryloxy-octahydro-chromen (also referred to herein as "Compound G"), as described in Example 6.
Figure 7:
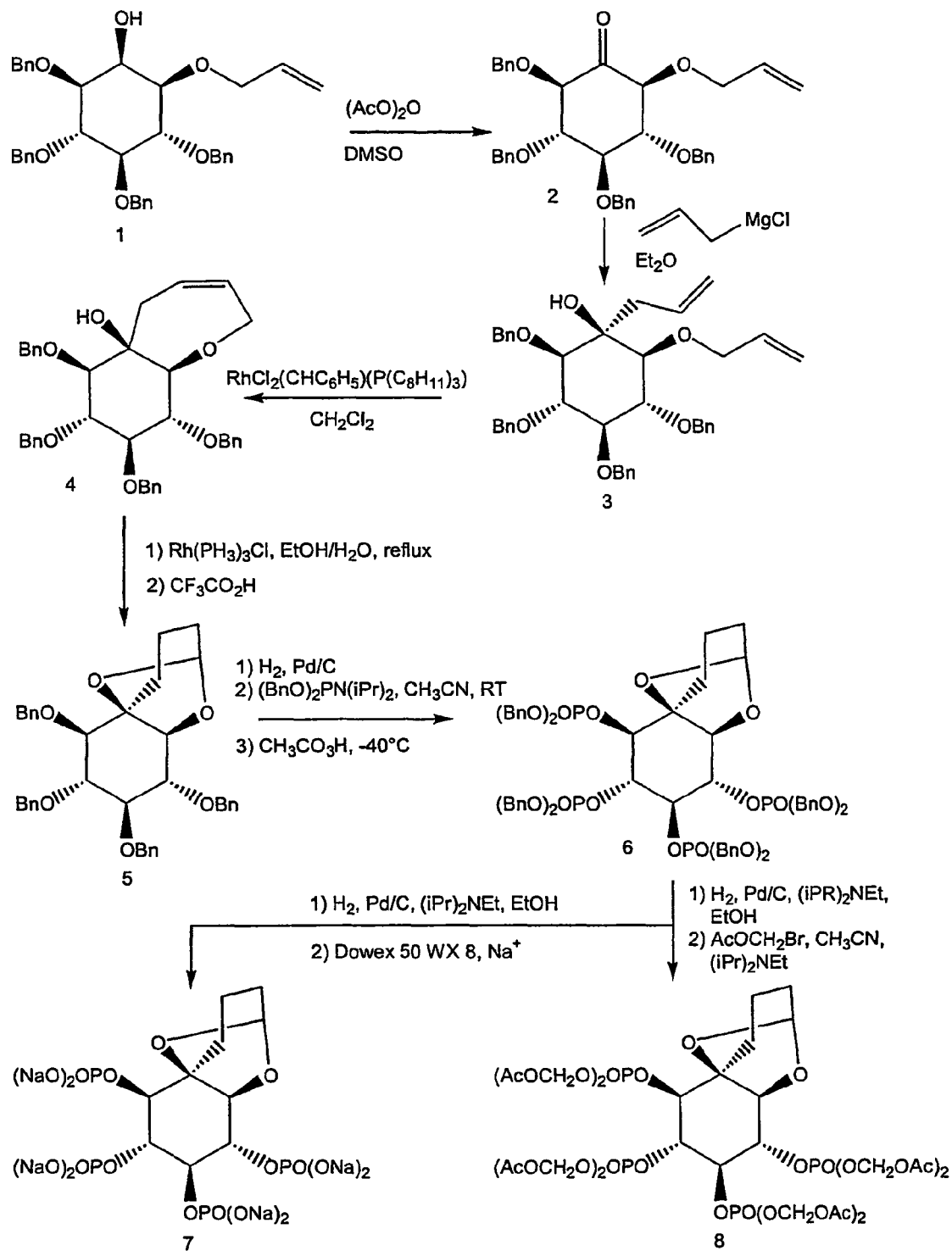
FIG. 7 is a reaction scheme showing a representative route for the synthesis of a tricyclo compound, (1S, 2R, 3S, 4R, 5S, 6S, 8R)-2,3,4,5-tetrakis-[[bis(acetoxymethoxy)phosphoryl]oxy]-7,12-dioxa-tricyclo-[6.3.1.0$^{(1,6)}$]-dodecane, as described in Example 7.
Figure 8:
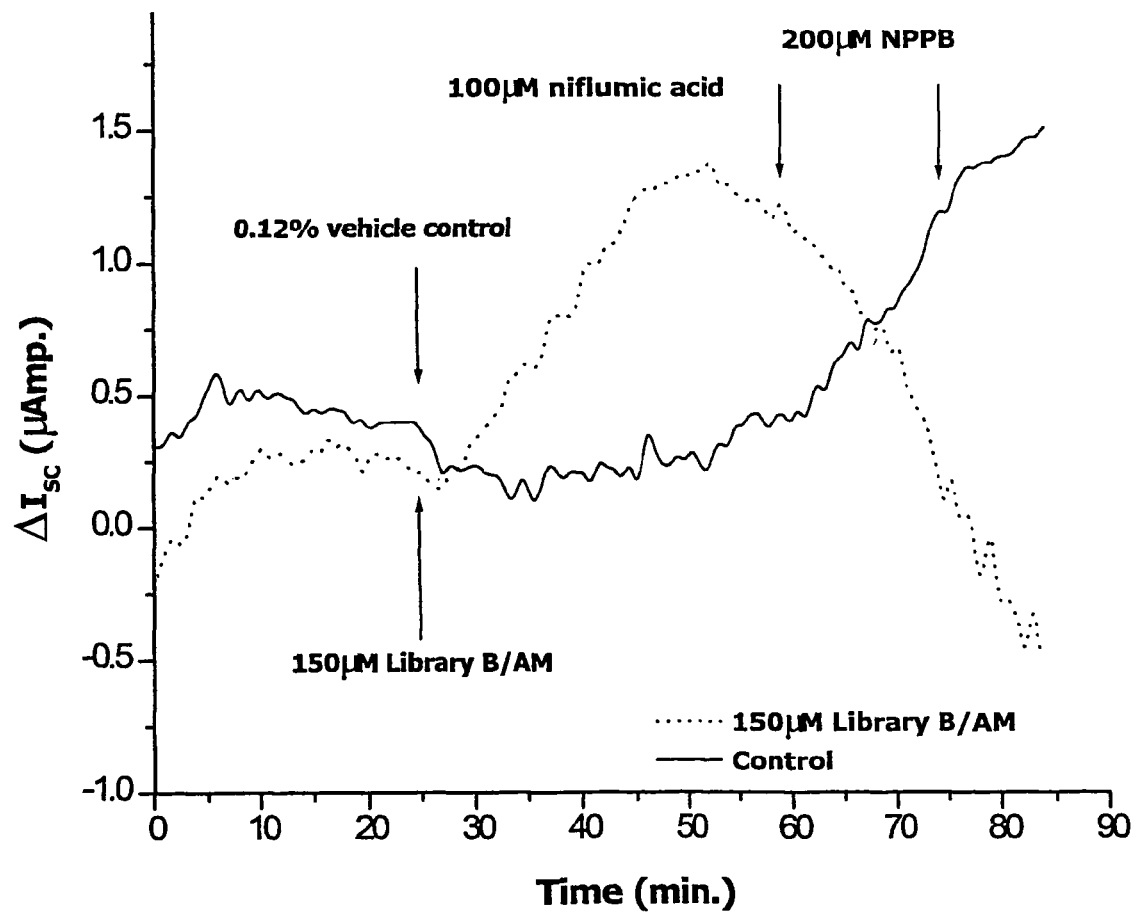
FIG. 8 is a graph showing transepithelial current stimulation by inositol derivative composition Library B, as described in Example 8. Monolayers were plated and mounted in modified Ussing chambers. Indomethacin (10 µM) and amiloride (100 µM) were added to the apical compartment and the baseline allowed to stabilize for 10-20 minutes prior to addition of the test composition. Final concentration of DMSO/DMSO-5% pluronic F-127=0.12%). Amiloride caused a decrease in $I_{sc}$ in 19 of 23 monolayers of 1.01 µAmps/cm$^2$.

In general, the compounds of the invention can be prepared by processes generally known in the art, and by the processes illustrated in Schemes I (FIG. 1), II (FIG. 2), III (FIG. 3), IV (FIG. 4), V (FIG. 5) and VI (FIG. 6). See, for example, T. Meyerdierks, H. H. Gillandt, and Carsten Schultz, *A Membrane-Permeant, Bioactivatable Derivative Of Ins*(1,4,6)P$_3$ *Elevates Intracellular Calcium Levels Of PC12 Cells*, (1999);

and C. Schultz et al., *Membrane-Permeant, Bioactivatable Derivatives of Inositol Polyphosphates and phosphoinositides*, in Phosphoinositides: Chemistry, Biochemistry and Biomedical Applications, K. S. Bruzik, Ed. *Am. Chem. Soc., Symp. Ser.,* 718, 232-243 (1998); for procedures for the production of compounds of structures I and II. In addition, representative compounds of structures II-IV are described in further detail in the figures and examples.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylproionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formulas (I)-(V), or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful in vitro for modulating chloride secretion in a cell or tissue, and in vivo in human and animal hosts for obtaining increases and decreases in chloride secretion. The compounds may be used alone or in compositions together with a pharmaceutically acceptable carrier.

Thus, in one aspect, the present invention provides methods of treatment of cystic fibrosis in a subject in need of such treatment by administering an inositol polyphosphate as given above to said subject in an amount effective to hydrate lung mucus secretions. In another aspect, the present invention provides methods of treating chronic bronchitis in a subject in need of such treatment by administering an inositol polyphosphate as given above to said subject in an amount effective to hydrate lung mucus secretions. In another aspect, the present invention provides methods of treating asthma in a subject in need of such treatment by administering an inositol polyphosphate analog as given above to said subject in an amount effective to hydrate lung mucus secretions. In another aspect, the present invention provides methods of combating chronic obstructive pulmonary disorder by inositol polyphosphate analog as given above to said subject in an amount effective to hydrate lung mucus secretions. In another aspect, the present invention provides methods of combating sinusitis by administering an inositol polyphosphate analog as given above to said subject in an amount effective to hydrate sinus mucus secretions. In another aspect, the present invention provides methods of combating diarrhea by administering an inositol polyphosphate analog as given above to said subject in an amount effective to reduce intestinal fluid secretion. In another aspect, the present invention provides methods of improving mucosal hydration in mucous membranes where insufficient hydration can lead to discomfort, such as in dryness of the eyes or dryness of the vaginal mucosa. In another aspect, the present invention provides methods of combating swelling by administering an inositol polyphosphate analog as given above to said subject in an amount effective to modulate fluid movement across membranes. In another aspect, the present invention provides methods of combating inflammation such as to reduce inflammation in such chronic conditions as asthma, adult respiratory distress syndrome, infant respiratory distress syndrome, osteoarthritis, rheumatoid arthritis, inflammatory bowel disease, psoriasis, dermatitis, other inflammatory conditions of the skin. In another aspect, the present invention provides methods of accelerating wound healing, by combating inflammation and swelling. In yet other aspects, the present invention provides methods of use of the active compounds for the treatment of chronic conditions shown to be alleviated by anti-inflammatory treatment such as arterioschlerosis and Alzheimers Disease. In yet other aspects the present invention provides methods of regulating fluid flux across membranes of the kidney. In yet other aspects, the present invention provides methods of use of an active compound as disclosed herein for the manufacture of a medicament for the prophylactic or therapeutic treatment of cystic fibrosis in a subject in need of such treatment. In yet other aspects, the present invention provides methods of use of an the active compounds as disclosed herein for the manufacture of a medicament for the prophylactic or therapeutic treatment of chronic bronchitis or the reduction of inflammation in a subject in need of such treatment. In yet other aspects, the present invention provides methods of use of an the active compounds as disclosed herein for the manufacture of a medicament for the prophylactic or therapeutic treatment of asthma in a subject in need of such treatment.

When administered to a patient, e.g., a mammal for veterinary use or to a human for clinical use, the inositol derivatives are preferably administered in isolated form. By "isolated" is meant that prior to formulation in a composition, the inositol derivatives are separated from other components of either (a) a natural source such as a plant or cell culture, or (b) a synthetic organic chemical reaction mixture. Preferably, via conventional techniques, the inositol derivatives are purified.

When administered to a patient, e.g., a mammal for veterinary use or to a human for clinical use, or when made to contact a cell or tissue, the inositol derivatives can be used alone or in combination with any physiologically acceptable carrier or vehicle suitable for enteral or parenteral delivery. Where used for enteral, parenteral, topical, otic, ophthalmologic, intranasal, oral, sublingual, intramuscular, intravenous, subcutaneous, intravaginal, transdermal, or rectal administration, the physiologically acceptable carrier or vehicle should be sterile and suitable for in vivo use in a human, or for use in a veterinary clinical situation.

In addition, the inositol derivatives can be administered to patients or contacted with a cell or tissue in liposome formulations, which facilitate their passage through cell membranes. Accordingly, the relative impermeability of cell membranes to relatively polar inositol derivatives can be overcome by their encapsulation in liposomal formulations. The characteristics of liposomes can be manipulated by methods known to those of ordinary skill in the art, such that size, membrane fluidity, tissue targeting, and compound release kinetics are adapted to the particular condition (Georgiadis, *NIPS* 4:146 (1989)). Liposomes of various sizes and compositions that encapsulate the inositol derivatives for delivery can be achieved by methods known to those skilled in the art (See, for example, Hope et al., *Biochem. Biophys. Acta* 812: 55 (1985); Hernandez, et al., *J. Microencapsul.* 4:315 (1987); Singh, et al., *Cancer Lett.* 84:15 (1994); and Dipali, et al., *J. Pharm. Pharmacol.* 48:1112 (1996)).

The inositol derivatives can be used in the form of a pharmaceutical preparation, for example, in solid, semisolid or liquid form, that contains at least one of the inositol derivatives of the present invention as a bioactive component, alone or in combination with an anti-inflammatory compound, in admixture with a carrier, vehicle or an excipient suitable for enteral or parental administration. Such anti-inflammatory compounds useful in this regard include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome; phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, colchicine, allopurinol, probenecid, sulfinpyrazone and benzbromarone.

In addition, the inositol derivatives of the present invention may be compounded, for example with a pharmaceutically acceptable carrier or vehicle for solid compositions such as tablets, pellets or capsules; capsules containing liquids; suppositories; solutions; emulsions; aerosols; sprays; suspensions or any other form suitable for use. Suitable carriers and vehicles include, for example, sterile water, sterile physiological saline, gum acacia, gelatin, starch paste, talc, keratin, colloidal silica, urea and the like. In addition, auxiliary, stabilizing, thickening, lubricating and coloring agents may be used. The inositol derivatives are present in the compositions in a therapeutically effective amount, i.e., an amount sufficient to restore normal mucosal secretions.

The compositions of this invention may be administered by a variety of methods including orally, sublingually, intranasally, intramuscularly, intravenously, subcutaneously, intravaginally, transdermally, rectally, by inhalation, or as a mouthwash in dosage unit formulations containing conventional nontoxic pharmaceutically acceptable carriers, adjuvants, and vehicles as desired. Topical administration may also involve the use of transdermal administration such as transdermal patches or ionophoresis devices. The preferred mode of administration is left to the discretion of the practitioner, and will depend in-part upon the desired site of action.

For example, when the cystic fibrosis, chronic bronchitis or asthma affects the function of the lungs, the inositol derivatives can be administered as an atomized aerosol, via a nebulizer, or via perfusion in a fluorocarbon or synthetic pulmonary surfactant; alternatively, the inositol derivatives can be administered intravenously directly. Thus, the active compounds disclosed herein may be administered to the lungs of a patient by any suitable means, but are preferably administered by generating an aerosol comprised of respirable particles, the respirable particles comprised of the active compound, which particles the subject inhales. The respirable particles may be liquid or solid. The particles may optionally contain other therapeutic ingredients such as a sodium channel blocker as noted above, with the sodium channel blocker included in an amount effective to inhibit the reabsorption of water from airway mucous secretions. The particles may optionally contain other therapeutic ingredients such as lantibiotics as described in U.S. Pat. Nos. 5,512,269 and 5,716, 931 or Uridine Triphosphate Analogs as described in U.S. Pat. No. 5,292,498, nitric oxide inhibitors as described in U.S. Pat. No. 5,859,058, dinucleotides as described in U.S. Pat. No. 5,935,555, or organic acids as described in U.S. Pat. No. 5,908,611. Particles comprised of active compound for practicing the present invention should include particles of respirable size: that is, particles of a size sufficiently small to pass through the mouth and larynx upon inhalation and into the bronchi and alveoli of the lungs. In general, particles ranging from about 0.5 to 10 microns in size (more particularly, less than about 5 microns in size) are respirable. Particles of non-respirable size which are included in the aerosol tend to deposit in the throat and be, swallowed, and the quantity of non-respirable particles in the aerosol is preferably minimized. For nasal administration, a particle size in the range of 10-500 μm is preferred to ensure retention in the nasal cavity.

Liquid pharmaceutical compositions of active compound for producing an aerosol can be prepared by combining the active compound with a suitable vehicle, such as sterile pyrogen free water. Other therapeutic compounds, such as a sodium channel blocker, may optionally be included. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant that serves to facilitate the formation of an aerosol. A suitable dispersant is lactose, which may be blended with the active compound in any suitable ratio (e.g., a 1 to 1 ratio by weight). Again, other therapeutic compounds, such as amiloride, may also be included.

The dosage of active compound for prophylaxis or treatment of lung disease will vary depending on the condition being treated and the state of the subject, but generally may be an amount sufficient to achieve dissolved concentrations of active compound on the airway surfaces of the subject of from about $10^{-9}$ to $10^{-3}$ Moles/liter, and more preferably from $10^{-7}$ to $10^{-5}$ Moles/liter. Depending on the solubility of the particular formulation of active compound administered, the daily dose may be divided among one or several unit dose administrations. Preferably, the daily dose is a single unit dose, which is preferably administered from 1 to 3 times a week. Treatments may continue week to week on a chronic basis as necessary (i.e., the active agent can be administered chronically). Administration of the active compounds may be carried out therapeutically (i.e., as a rescue treatment) or prophylactically, but preferably the compounds are administered prophylactically, either before substantial lung blockage due to retained mucus secretions has occurred, or at a time when such retained secretions have been at least in part removed, as discussed above.

Aerosols of liquid particles comprising the active compound may be produced by any suitable means, such as with a nebulizer. See, e.g., U.S. Pat. No. 4,501,729. Nebulizers are commercially available devices that transform solutions or suspensions of the active ingredient into a therapeutic aerosol mist either by means of acceleration of a compressed gas; typically air or oxygen, through a narrow venturi orifice or by means of ultrasonic agitation. Suitable formulations for use in nebulizers consist of the active ingredient in a liquid carrier, the active ingredient comprising up to 40% w/w of the formulation, but preferably less than 20% w/w. the carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, antioxidants, flavoring agents, volatile oils, buffering agents and surfactants. Aerosols of solid particles comprising the active compound may likewise be produced with any solid particulate medicament aerosol generator. Aerosol generators for administering solid particulate medicaments to a subject produce particles that are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders that may be delivered by means of an insufflator or taken into the nasal cavity in the manner of a snuff. In the insufflator, the powder (e.g., a metered dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents. The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

Where the condition of the subject to be treated affects the gastrointestinal tract, the inositol derivatives can be administered rectally via enema or suppository, or orally in the form of a tablet or capsule formulated to prevent dissolution prior to entry into the afflicted portion of the gastrointestinal tract; when the cystic fibrosis affects vaginal secretions, the inositol derivatives can be administered intravaginally, in the form of a douche.

Compositions for oral delivery may be in the form of tablets, pills, troches, lozenges, aqueous or oily suspensions, granules or powders, emulsions, capsules, syrups or elixirs. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, compositions in tablet form may be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in ⅓-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Aqueous suspensions containing the inositol derivatives may also contain one or more preservatives, such as, for example, ethyl or n-propyl-p-hydroxy-benzoate, one or more coloring agents, flavoring agents or sweetening agents.

Because the inositol derivatives are in the form of tetrakisphosphate, heptakis or octakis(acetoxymethyl or ethyl)esters, and because the inositol derivatives can contain —$C_1$-$C_{20}$ straight or branched chain alkyl, —OC(O)$C_1$-$C_{20}$ straight or branched chain alkyl or —O$C_1$-$C_{20}$ straight or branched chain alkyl groups, the inositol derivatives possess enhanced lipophilic properties which allow for passive diffusion across plasma membranes.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N. W. (1976), p.33 et seq.

Without being bound by any particular theory, it is believed that the inositol derivatives function as "prodrugs" of a metabolized form of the inositol derivatives that are the actual pharmacological agent responsible for the promotion of chloride secretion. Such prodrugs, by virtue of their being more lipophilic than the actual pharmacological agents themselves, can more easily penetrate plasma membranes. Once within a secretory cell, the prodrugs are converted, generally enzymatically, to the active pharmacological agent. In addition, because in vivo conversion of a prodrug to its active pharmacological form generally occurs over a period of time, rather than instantaneously, the use of prodrugs offers the patient or subject the benefit of a sustained release of the pharmacological agent, generally resulting in a longer duration of action.

In a further embodiment, the present invention contemplates the use of an inositol derivative when delivered at a dose of about 0.001 mg/kg to about 100 mg/kg body weight, preferably from about 0.01 to about 10 mg/kg body weight. The inositol derivatives can be delivered up to several times per day, as needed. Treatment can be continued, indefinitely to normalize mucosal hydration or chloride secretion or reduce excessive mucosal viscosity.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

While the compounds of the invention can be administered as the sole active pharmaceutical agent, they can also be used in combination with one or more other agents used in the treatment of the symptoms of cystic fibrosis, chronic bronchitis, asthma, inflammation and the like. For alleviating mucosal viscosity resulting from cystic fibrosis, a composition of the present invention may be administered that comprises an inositol derivative of the invention together with an agent useful for the treatment of inflammation-accompanying condition. For instance, for the treatment of cystic fibrosis, such an agent can be mucolytics (e.g., Pulmozyme® and Mucomyste®, purinergic receptor agonists such as uridine triphosphate (UTP), agents that suppress the cystic fibrosis transmembrane regulator (CFTR) premature stop mutation such as gentamycin, agents correcting the Delta F508 processing defect also known as "protein assist therapies" such as CPX™ (SciClone), Phenylbutyrate (Ucyclyd Pharma), INS365, and genestein, and/or agents for the treatment of the accompanying infection such as tobramycin or aerosolized tobramycin (Tobi™), meropenem, RSV vaccine, IB605, Pa1806, anti-inflammatory agents such as DHA, rHEI, DMP777, IL10 (Tenovil) and/or agents triggering alternate chloride channels such as lantibiotics such as Duramycin (Moli901—Molichem Medicines), or omeprazole, and/or purinergic agonists such as nucleotide or dinucleotide analogs, or agents affecting sodium transport such as amiloride, and/or agents affecting pH such as organic acids.

For the treatment of asthma, such agents can be corticosteroids—such as fluticasone proprionate (Flovent®, Flovent Rotadisk®), budesonide (Pulmocort Turbuhaler®), flunisolide (Aerobid®), triamcinolone acetonide (Azmacort®), beclomethasone MDI (Beclovent®), Antileukotrienes such as Zafirlukast (Accolate®, Zeneca®), Zileuton (Zyflo®), Montelukast or other therapies such as Methotrexate, Troleandomycin, Gold, Cyclosporine, 5' lipoxygenase inhibitors, bronchodilators, or immunotherapeutic agents.

CPX is a caffeine-like compound being investigated by SciClone. In laboratory studies it appears to increase chloride secretion in CF tissues that have the delta F508 mutation, but not in tissues with other mutations or normal epithelial cells. It is unknown whether it would be effective in actual patients. Even if so, it would not benefit the 30% of CF sufferers who have other mutations.

Phenylbutyrate is a compound developed by Ucyclyd Pharma that targets the protein generated by the delta F508 mutation. The Cystic Fibrosis Foundation is currently sponsoring a Phase I clinical trial of the drug at the Johns Hopkins University. However, because high concentrations are necessary to be effective and the compound has an unappealing odor, other active analogs are currently being sought.

Duramycin is being developed by Molichem Medicines and, like phenylbutyrate, is reported to facilitate insertion of the delta F508 CFTR into the plasma membrane. Unfortunately, duramycin is not effective in the 30% of CF patients who have a genetic mutation other than delta F508.

Purinergic (P2Y2) receptor agonists such as adenosine triphosphate (ATP) and uridine triphosphate (UTP) stimulate calcium-dependent chloride channels (not CFTR channels). They are currently being investigated by researchers at the University of North Carolina (under the auspices of Inspire Pharmaceuticals, Inc.) and independently at Johns Hopkins University. Early trials indicate that this strategy could be useful in the treatment of cystic fibrosis and other chronic obstructive pulmonary disorders. However, the effectiveness of this approach may be limited by inflammation-related inhibitory signals.

The compounds of the invention may also be administered in combination with one or more sodium channel blockers. Sodium channel blockers that may be used in the present invention are typically pyrazine diuretics such as amiloride, as described in U.S. Pat. No. 4,501,729. The term "amiloride" as used herein includes the pharmaceutically acceptable salts thereof, such as (but not limited to) amiloride hydrochloride, as well as the free base of amiloride. The quantity of amiloride included may be an amount sufficient to achieve dissolved concentrations of amiloride on the airway surfaces of the subject of from about $10^{-7}$ to about $10^{-3}$ Moles/liter, and more preferably from about $10^{-6}$ to about $10^{-4}$ Moles/liter.

The methods of the present invention may also further comprise the step of removing retained mucus secretions from the lungs of the subject prior to the step of administering the active agent. This facilitates application of the active agent to the respiratory epithelia during the administering step. Such removal of retained mucus secretions can be carried out by any suitable means, including postural drainage, antibiotic administration (e.g., intravenous or inhalation administration of cephalosporin or aminoglycoside antibiotics such as Tobramycin), and/or inhalation administration of DNase. In addition, the present invention may be carried out on patients such as children prior to decline of respiratory function (e.g., patients essentially free of lung blockage due to retained mucus secretions). Such patients can be genetically predisposed to becoming afflicted with lung disease (e.g., cystic fibrosis) as hereinbefore described.

Alternatively, the compositions comprising an inositol derivative can be administered in combination with, prior to, concurrent with or subsequent to the administration of another agent useful for the treatment of cystic fibrosis accompanying condition, as described above.

In addition, the inositol derivatives can be used for research purposes, for example, to investigate the mechanism and activity of other agents thought to be useful for regulating mucosal hydration.

The foregoing may be better understood by reference to the following examples, which are provided for, illustration and are not intended to limit the scope of the inventive concepts.

EXAMPLE 1

Synthesis of 2,3,5-Tri-O-butyryl-myo-inositol 1,4,6-Trisphosphate Hexakis(proprioxymethyl) Ester (1). [TMX]

Referring to the reaction scheme shown in FIG. 1, the compound 2,3,5-tri-O-butyryl-myo-inositol 1,4,6-trisphosphate hexakis(proprioxymethyl)ester was synthesized as follows:

rac-1,4,6-Tri-O-benzyl-2,3-O-cyclohexylidene-myo-inositol (rac-4), rac-1,4,5-Tri-O-benzyl-2,3-O-cyclohexylidene-myo-inositol (rac-5) and rac-1,5-Di-O-benzyl-2,3-O-cyclohexylidene-myo-inositol Under an argon atmosphere benzyl bromide (6 mL, 48 mmol) was added to a suspension of dry 1,2-O-cyclohexylidene-myo-inositol rac-3 (2.08 g, 8 mmol), dry dibutyltin oxide (9.96 g, 40 mmol) and dry tetrabutylammonium bromide (12.9 g, 40 mmol) in dry toluene (200 mL). The solution was stirred and heated under reflux in a Soxhlet apparatus filled with activated molecular sieves (3 Å) for 24 h. After the reaction mixture was cooled to room temperature and $Et_3N$ (14 mL, 96 mmol) was added, the reaction was stirred for a further 20 h to destroy the excess of benzyl bromide. The solvent was evaporated, the residue was dissolved in tert-butyl methyl ether (100 mL), and was washed twice with sodium hydrogen carbonate (50 mL), with sodium hydrogen sulfate (50 mL), with phosphate buffer (50 mL), and finally with brine (50 mL). The organic layer was dried over $Na_2SO_4$ and filtered. The solvent was removed under reduced pressure and the residual compounds were isolated and purified by preparative HPLC [87% MeOH, 40 mL/min, $t_{Ret}$=16.54 min (rac-6); $t_{Ret}$=30.49 min (race and rac-5)].

rac-4:

(1.877 g, 44.3%) (calculated from starting material)

$^1$H-NMR (CDCl$_3$, 360 MHz): δ 1.25-1.86 (10H, m, cyclohexylidene), 2.70 (1H, d, J=1.98 Hz, OH), 3.58 (1H, dd, J=7.83, 7.83, 1.98 Hz, H-5), 3.69-3.94 (3H, m, H-3, H-4, H-6), 4.17 (1H, dd, J=6.67, 6.56 Hz, H-2), 4.38 (1H, dd, J=5.62, 3.64 Hz, H-1), 4.71-5-08 (6H, m, CH$_2$Ph), 7.22-7.50 (1SH, m, CH$_2$h). MS: m/z (pos. mode, DCI) 548 [(M+NH$_4^{30}$)$^+$, 100]. MS: m/z (neg. mode, DCI) 529 [(M-H$^+$)$^-$, 30]. 439 [(M-C$_7$H$_7^+$)$^-$, 30].

rac-5:

(1.455 g, 34.3%/o) (calculated from starting material)

Mp: 94.6-95° C. $^1$H-NMR (CDCl$_3$, 360 MHz): δ 1.20-1.88 (10H, m, cyclohexylidene), 2.65 (1H, s, OH), 3.35 (1H, dd, J=9.15, 9.15 Hz, H-5), 3.61 (1H, dd, J=9.76, 3.80 Hz, H-3), 3.77 (1H, dd, J=9.21, 6.67 Hz, H-6), 4.12 (1H, dd, J=9.43, 9.43 Hz, H-4), 4.18 (1H, dd, J=6.56, 5.24 Hz, H-1), 4.39 (1H, dd, J=4.91, 4.24 Hz, H-2), 4.72-4.99 (6H, m, CH$_2$Ph), 7.20-7.51 (15H, m, CH$_2$Ph). MS: m/z (pos. mode, DCI) 548 [(M+NH$_4^+$)$^+$, 72]. MS: m/z (neg. mode, DCI 529 [(M-H$^+$)$^-$, 42]. 439 [(M-C$_7$H$_7^+$)$^-$, 38]. Anal.(C$_{33}$H$_{38}$O$_6$): C calcd, 74.69; found, 74.79. H: cald, 7.22; found, 7.31.

rac-1,5-Di-O-benzyl-2,3-O-cyclohexylidene-myo-inositol:

(468 mg, 13.3%) (calculated from starting material)

Mp: 148.1-148.9° C. $^1$H-NMR (CDCl$_3$, 360 MHz): δ 1.23-1.58 (10H, m, cyclohexylidene), 2.68 (2H, s, OH), 3.38 (1H, dd, J=Hz, H-4), 3.53 (1H, dd, J Hz, H-3), 3.55 (1H, dd, J=Hz, H-6), 3.96 (1H, dd, J=Hz, H-5), 4.09 (1H, dd, J Hz, H-1), 4.33 (1H, dd, J=Hz, H-2), 4.63-5.03 (4H, m, CH$_2$Ph), 7.28-7.47 (10H, m, CH$_2$Ph). MS: m/z (pos. mode, DCI) 458 [(M+NH$_4^+$)$^+$, 100]. MS: m/z (neg. mode, DCI) 439 [(M-H$^+$)$^-$, 35]. 349 [(M-C$_7$H$_7^+$)$^-$, 73]. HRMS: in/z 439.2120 (M-H$^+$)$^-$ (calcd for C$_2$H$_{31}$O$_6$, 439.2121).

rac-1,4,6-Tri-O-benzyl-myo-inositol (rac-6)

A solution of rac-4 (1.70 g, 3.208 mmol) in MeCN/H$_2$O (100:1, 3 mL) was stirred with trifluoroacetic acid (1 mL) at room temperature for 1 h. The solvent was evaporated under reduced pressure. The residue was washed with cold acetonitrile and the procedure was repeated twice to give the title compound rac-6 (1,095 g, 76%) as a solid.

Mp: 116,8-117,4° C. $^1$H-NMR (CDCl$_3$, 360 MHz): δ 2.19 (3H, s, OH), 3.40-3.52 (2H, m, H-1, H-3), 3.52 (1H, dd, J=9.16, 9.16 Hz, H-5), 3.73 (1H, dd, J=9.32, 9.32 Hz, H-6), 3.82 (1H, dd, J=9.37, 9.37 Hz, H-4), 4.22 (1H, dd, J=2.82, 2.82 Hz, H-2), 4.68-5.03 (6H, m, CH$_2$Ph), 7.27-7.43 (15H, m, CH$_2$Ph). MS: m/z (pos. mode, DCI) 468 [(M+NH$_4^+$)$^+$, 34], 198[(M-3C$_7$H$_7^+$+NH$_4^+$+3H$^+$)$^+$, 67]. MS: m/z (neg. mode, CI) 449 [(M-H$^+$)$^-$, 28]. 359 [(M-C$_7$H$_7^+$)$^-$, 52]. Anal. (C$_{27}$H$_{30}$O$_6$): C calcd, 71.98; found, 71.66; H: cald, 6.71; found, 6.62.

Preparation of Enantiomerically Pure 1,4,6-Tri-O-benzyl-myo-inositol (6) and 3,4,6-Tri-O-benzyl-myo-inositol (ent-6)

A solution of the racemic triol (rac-6) (1.069 g, 2.376 mmol) and S-(−)-camphanic acid chloride (1.030 g, 4.752 mmol) in dry pyridine was kept at room temperature for 2 days. All volatile compounds were removed under reduced pressure and residual pyridine was removed by evaporating three times with octane. The residue was dissolved in tert-butyl methyl ether (100 mL) and was washed twice with sodium hydrogen sulfate (50 mL), with phosphate buffer (50 mL), and finally with brine (50 mL). The organic layer was dried over Na$_2$SO$_4$ and filtered. Evaporation of the solvent and crystallization from methanol gave pure dia-7 (293 mg, 58%, ee>98%) as a solid. The other diastereomer 7 was isolated and purified by preparative HPLC (80% MeOH, 40 mL/min., $t_{Ret}$=30.49 min) as an oil (214.4 mg, 42%, ee 82%).

7: Mp: 187.5-189.8° C. [α]$^{20}_D$+6,24 (c=1.01 in CHCl$_3$). $^1$H-NMR (CDCl$_3$, 360 MHz): δ 0.72 (3H, s, CH$_3$-camph.), 0.91 (3H, s, CH$_3$-camph.), 0.95 (3H, s, CH$_3$-camph.), 0.99 (3H, s, CH$_3$-camph.), 1.03 (3H, s, CH$_3$-camph.), 1.10 (3H, s, CH$_3$-camph.), 1.49-1.95 (6H, m, CH$_2$-camph.), 2.13-2.44 (3H, m, CH$_2$-camph.), 3.66 (1H, dd, J=9.49, 2.58 Hz, H-1), 4.07 (1H, dd, J=9.68, 9.68 Hz, H-6), 4.28 (1H, dd, J=10.07, 10.07 Hz, H-4), 4.33 (1H, dd, J=2.38, 2.38 Hz, H-2), 4.61-4.97 (6H, m, CH$_2$Ph), 5.02 (1H, dd, J=10.22, 2.63 Hz, H-3), 5.36 (1H, dd, J=9.78, 9.78 Hz, H-5), 7.18-7.41 (15H, m, CH$_2$Ph. MS: m/z (pos. mode, DCI) 828 [(M+NH$_4^+$)$^+$, 70].

MS: m/z (neg. mode, DCI) 719 [(M–C$_7$H$_7$$^+$)$^-$, 8]. Anal. (C$_{49}$H$_{62}$O$_{10}$): C calcd. 72.57; found, 68.86. H: cald, 7.71; found, 7.60.

dia-7: Mp: 185.3-186.8° C. [α]$^{20}_D$+2,62 (c=1.03 in CHCl$_3$). $^1$H-NMR (CDCl$_3$, 360 MHz): δ 0.72 (3H, s, CH$_3$-camph.), 0.85 (3H, s, CH$_3$-camph.), 0.91 (3H, s, CH$_3$-camph.), 1.02 (3H, s, CH$_3$-camph.), 1.07 (3H, s, CH$_3$-camph.), 1.09 (3H, s, CH$_3$-camph.), 1.46-2.04 (6H, m, CH$_2$-camph.), 2.06-2.39 (3H, m, CH$_2$-camph.), 3.68 (1H, dd, J=9.39, 2.61 Hz, H-3), 4.04 (1H, dd, J=9.63, 9.63 Hz, H-4), 4.26 (1H, dd, J=10.02, 10.02 Hz, H-6), 4.39 (1H, dd, J=2.71, 2.71 Hz, H-2), 4.60-4.94 (6H, m, CH$_2$Ph), 4.98 (1H, dd, J=10.31, 2.66 Hz, H-1), 5.35 (1H, dd, J=9.83, 9.83 Hz, H-5), 7.15-7.37 (15H, m, CH$_2$Ph. MS: m/z (pos. mode, DCI) 828 [(M+NH$_4$$^+$)$^+$, 100].

MS: m/z (neg. mode, CI) 719 [(M–C$_7$H$_7$$^+$)$^-$, 40]. Anal. (C$_{49}$H$_{62}$O$_{10}$): C calcd. 72.57; found, 69.72. H: cald, 7.71; found, 6.89.

To generate the enantiomerically pure compounds 6 and ent-6 each ester was dissolved in MeOH, 2N KOH (to pH z 14) was added, and the solution was stirred overnight at room temperature. After the reaction mixture was neutralized with 1N HCl, the solvent was evaporated under reduced pressure and the residual product was extracted with tert-butyl methyl ether (100 mL). The organic layer was washed with sodium hydrogen carbonate (50 mL), phosphate buffer (50 mL) and finally twice with brine (50 mL), dried with Na$_2$SO$_4$ and filtered. Evaporation of the solvent gave the title compounds 6 (99.4 mg, 99%) and ent-6 (142.8 mg, 95%).

6: Mp: 117.5-118.2° C. [α]$^{20}_D$+0.5 (c=1.07 in CHCl$_3$). $^1$H-NMR (CDCl$_3$, 360 MHz): δ 2.47-2.62 (3H, s, OH), 3.42-3.59 (3H, m, H-1, H-3, H-5), 3.73 (1H, dd, J=9.28, 9.28. Hz, H-6), 3.82 (1H, dd, J=9.23, 9.23 Hz, H-4), 4.23 (1H, dd, J=2.64, 2.64 Hz, H-2), 4.67-5.05 (6H, m, CH$_2$Ph), 7.23-7.53 (15H, m, CH$_2$Ph). MS: m/z (pos. mode, DCI) 468 [(M+NH$_4$$^+$)$^+$, 100]. MS: m/z (neg. mode, DCI) 449 [(M–H$^+$)$^-$, 10]. 359 [(M–C$_7$H$_7$$^+$)$^-$, 56]. HRMS: m/z 449.1960 (M–H$^+$)$^-$ (calcd for C$_{27}$H$_{29}$O$_6$, 449.1964).

ent-6: Mp: 116.8-118.9° C. [α]$^{20}_D$–0.7 (c 1.11 in CHCl$_3$). $^1$H and MS data were in accordance with those obtained for 7.

1,4,6-Tri-O-benzyl-2,3,5-tri-O-butryl-myo-inositol (8).

A solution of 6 (97.9 mg, 218 µmol), butyric anhydride (213 µL, 1.305 mmol), and DMAP (3 mg, 22 µmol) in dry pyridine (4 mL) was stirred at room temperature for 12 h. The solvent was evaporated under high vacuum to give an oil. Residual pyridine was removed by evaporating three times with octane. The residue was dissolved in tert-butyl methyl ether (100 mL) and was washed twice with phosphate buffer (50 mL), with sodium hydrogen sulfate (50 mL), again with phosphate buffer (50 mL), and finally with brine (50 mL). The organic layer was dried over Na$_2$SO$_4$ and filtered. The solvent was removed under reduced pressure and the residual oil was purified by preparative HPLC (91% MeOH; 40 mL/min.; t$_{Ret}$=23.75 min) to give the fully protected compound 8 (105.9 mg, 74%).

[α]$^{20}_D$+0.50 (c=1.26 in CHCl$_3$). $^1$H-NMR (CDCl$_3$, 360 MHz): δ 0.88 (3H, t, J=7.44 Hz, CH$_3$-Bt), 0.91 (3H, t, J=7.35 Hz, CH$_3$-Bt), 1.01 (3H, t, J=7.40 Hz, CH$_3$-Bt), 1.46-1.78 (6H, m, β-CH$_2$-Bt), 2.05-2.25 (4H, m, α-CH$_2$-Bt), 2.41 (2H, t, J=7.25 Hz, α-CH$_2$-Bt), 3.69 (1H, dd, J=9.63, 2.63 Hz, H-1), 3.80 (1H, dd, J=9.39, 9.39 Hz, H-6), 3.90 (1H, dd, J=9.97, 9.97 Hz, H-4), 4.43-4.90 (6H, m, CH$_2$Ph), 4.96 (1H, dd, J=10.32, 2.82 Hz, H-3), 5.22 (1H, dd, J=9.54, 9.54 Hz, H-5), 5.80 (1H, dd, J=2.77, 2.77 Hz, H-2), 7.17-7.38 (15H, m, CH$_2$Ph). MS: m/z (pos. mode, DCI) 678 [(M+NH$_4$$^+$)$^+$, 100]. MS: m/z (neg. mode, DCI) 659 [(M–H$^+$)$^-$, 30]. 569 [(M–C$_7$H$_7$$^+$)$^-$, 100]. HRMS: m/z 659.3220 (M–H$^+$)$^-$ (calcd for C$_{39}$H$_{47}$O$_9$, 659.3220).

3,4,6-Tri-O-benzyl-1,2,5-tri-O-butyl-myo-inositol (ent-8).

Compound ent-6 (122.6 mg, 272 µmol) was butyrylated as described for 9 to give the fully protected inositol ent-8 (140.8 mg, 78%) as an oil. [α]$^{20}_D$–0.30 (c=1.35 in CHCl$_3$). $^1$H and MS data were in accordance with those obtained for 8.

2,3,5-Tri-O-butryl-myo-inositol (9).

Compound 8 (100.7 mg, 153 µmol) was suspended in acetic acid (4 mL) and hydrogenated with palladium (10%) on charcoal (92 mg, 915 µmol) under a hydrogen atmosphere in a self-built hydrogenation apparatus for 12 h. The catalyst was, removed by ultrafiltration and the filtrate was freeze-dried to give 9 (56 mg, 94%) as a hygroscopic solid.

[α]$^{20}_D$+15.1 (c 0.67 in CHCl$_3$). $^1$H-NMR (CDCl$_3$, 360 MHz): δ 0.88-1.04 (9H, m, CH$_3$-Bt), 1.52-1.80 (6H, m, β-CH$_2$-Bt), 2.22-2.48 (6H, m, α-CH$_2$-Bt), 2.49-2.74 (3H, s, OH), 3.79-3.86 (2H, m, H-1, H-6), 3.92 (1H, dd, J=9.98, 9.98 Hz, H-4), 4.89-5.01 (2H, m, H-3, H-5), 5.56 (1H, dd, J=1.92, 1.92 Hz, H-2). MS: m/z (pos. mode, DCI) 408 [(M+NH$_4$$^+$)$^+$, 100]. MS: m/z (neg. mode, DCI) 196 [(M–3Bt$^+$+H$_2$O+H$^+$)$^{2-}$, 100].

HRMS: m/z 389.1800 (M–H$^+$)$^-$ (calcd for C$_{18}$H$_{29}$O$_9$, 389.1812).

1,2,5-Tri-O-butyryl-myo-inositol (ent-9).

Compound ent-8 (134.5 mg, 204 µmol) was hydrogenated as described for 8 to give ent-9 (74.7 mg, 94%) as a hygroscopic solid.

[α]$^{20}_D$–14.5 (c=0.42 in CHCl$_3$). $^1$H and MS data were in accordance with those obtained for 9.

2,3,5-Tri-O-butyryl-myo-inositol 1,4,6-Tris(dibenzyl)phosphate (10).

A solution of tetrol 9 (40.6 mg, 104 µmol) and tetrazole (55 mg, 781 mmol) in acetonitrile (5 mL) was treated with dibenzyl N,N-diisopropylphosphoramidite (257 µL, 781 µmol) for 20 h and subsequently oxidized with peracetic acid (200 µL, 781 µmol) at –40° C. After the mixture warmed to room temperature, the solvent was removed under reduced pressure and the residual oil was purified by preparative HPLC (88% MeOH; 40 mL/min., t$_{Ret}$=34.75 min) to give the fully protected compound 10 (96 mg, 79%) as a clear oil.

[α]$^{20}_D$–5.5 (c=8 in CHCl$_3$). $^1$H-NMR (CDCl$_3$, 360 MHz): δ 0.69 (3H, t, J=7.48 Hz, CH$_3$-Bt), 0.81 (3H, t, J=7.38 Hz, CH$_3$-Bt), 0.96 (3H, t, J=7.38 Hz, CH$_3$-Bt), 1.24-1.75 (6H, m, β-CH$_2$-Bt), 1.98-2.40 (6H, m, α-CH$_2$-Bt), 4.47 (1H, ddd, J=9.78, 8.46, 2.69 Hz, H-1), 4.73-5.13 (15H, m, H-3, H-4, H-6, 6×CH$_2$Ph), 5.32 (1H, dd, J=9.59, 9.59 Hz, H-5), 5.87 (1H, dd, J=2.59, 2.59 Hz, H-2), 7.16-7.38 (30H, m, 6×CH$_2$PH). $^{31}$P-NMR (CDCl$_3$, $^1$H decoupled, 145.8 MHz): –0.69 (1 P, s), –0.55 (1 P, s), –0.42 (1 P, s). MS: m/z (neg. mode, DCI) 1079 [(M–C$_7$H$_7$$^+$)$^-$, 100]. HRMS: m/z 1079.3449 (M–C$_7$H$_7$$^+$)$^-$(calcd for C$_{53}$H$_{62}$O$_{18}$P$_3$, 1079.3149).

1,2,5-Tri-O-butyryl-myo-inositol 3,4,6-Tris(dibenzyl)phosphate (ent-10).

Tetrol ent-9 (63.6 mg, 163 µmol) was phosphorylated as described for compound 10 to give the fully protected phosphate ent-10 (157.2 mg, 82%) as a clear oil. [α]$^{20}_D$+5.43 (c=10 in CHCl$_3$).

$^1$H, $^{31}$P and MS data were in accordance with those obtained for 10.

2,3,5-Tri-O-butyryl-myo-inositol 1,4,6-Trisphosphate (11).

Compound 10 (94.1 mg, 80 μmol) was hydrogenated with palladium (10%) on charcoal as described for compound 9 to give the title compound 11 (58.8 mg, 100%) as a hygroscopic solid after freeze-drying.

$[\alpha]^{20}_D$ −1.71 (c=1.49 in $CHCl_3$). $^1$H-NMR ($D_2O$, 360 MHz): δ 0.74 (3H, t, J=7.61 Hz, $CH_3$-Bt), 0.78 (3H, t, J=7.42 Hz, $CH_3$-Bt), 0.83 (3H, t, J=7.53 Hz, $CH_3$-Bt), 1.32-1.65 (6H, m, β-$CH_2$-Bt), 2.15-2.44 (6H, m, α-$CH_2$-Bt), 4.32-4.59 (3H, m, H-1, H-4, H-6), 5.07 (1H, dd, J=9.92, 2.65 Hz, H-3), 5.14 (1H, dd, J=9.52, 9.52 Hz, H-5), 5.57 (1H, dd, J=2.46, 2.46 Hz, H-2). $^{31}$P-NMR ($D_2O$, $^1$H decoupled, 145.8 MHz): δ 0.09 (1P, s), 0.70 (1P, s), 0.78 (1P, s).

MS: m/z (neg. mode, DCI) 629 [$(M-H^+)^-$; 28], 559 [$(M-Bt^+)^-$, 52].

1,2,5-Tri-O-butyryl-myo-inositol 3,4,6-Trisphosphate (ent-11).

Compound ent-10 (155.3 mg, 133 μmol) was hydrogenated as described for 11 to give the free acid ent-11 (90.7 mg, 100%) as a hygroscopic solid. $[\alpha]^{20}_D$+1.85 (c 2.75 in $CHCl_3$). $^1$H, $^{31}$P and MS data were in accordance with those obtained for 2,3,5-Tri-O-butyryl-myo-inositol 1,4,6-Trisphosphate Hexakis(acetoxymethyl) Ester DIEA (118 μL, 690 μmol) and acetoxymethyl bromide (69 μL, 690 mmol) were added to a suspension of compound 11 (28.7 mg, 46 μmol) in dry acetonitrile (2 mL) under an argon atmosphere. After the reaction mixture stirred in the dark for 5 days, all volatile compounds were removed under reduced pressure and the crude residue was purified by preparative HPLC (70% MeOH; 40 mL/min.; $t_{Ret}$=18.20 min) to give compound 1 (34.3 mg, 71%) as a clear syrup. $[\alpha]^{20}_D$+0.44 (c 1.127 in toluene).

$^1$H-NMR (toluene-$d_8$, 360 MHz): δ 0.85 (3H, t, J=7.68 Hz, $CH_3$-Bt), 0.89 (3H, t, J=7.43 Hz, $CH_3$-Bt), 1.06 (3H, t, J=7.48 Hz, $CH_3$-Bt), 1.43-1.96 (20H, m, β-$CH_2$-Bt, 6×OAc), 2.00-2.49 (8H, m, α/β-$CH_2$-Bt), 2.64-2.76 (2H, m, α-$CH_2$-Bt), 4.56 (1H, ddd, J=9.54, 9.54, 2.84 Hz, H-1), 4.94 (1H, dd, J=9.63, 9.63 Hz, H-6), 5.02 (1H, dd, J=10.17, 2.84 Hz, H-3), 5.03 (1H, dd, J=9.73, 9.73 Hz, H-4), 5.29-5.80 (13H, m, H-5, 6×$CH_2$OAc), 5.96 (1H, dd, J=2.64, 2.64 Hz, H-2). $^{31}$P-NMR (toluene-$d_8$, $^1$H decoupled, 145.8 MHz): 6-3.72 (1P, s), −3.40 (1P, s), −3.34 (1P, s). MS: m/z (neg. mode, DCI) 989 [$(M-CH_2OCOCH_3^+)^-$, 100]. HRMS: m/z 989.1858 $(M-CH_2OCOCH_3^+)^-$ (calcd for $C_{33}H_{52}O_{28}P_3$, 989.1858).

1,2,5-Tri-O-butyryl-myo-inositol 3,4,6-Trisphosphate Hexakis(acetoxymethyl) Ester (ent-1).

The free acid ent-11 (49.4 mg, 78 μmol) was alkylated as described for compound 1 to give the acetoxymethyl ester ent-1 (36.8 mg, 44%) as a clear syrup. $[\alpha]^{20}_D$−0.41 (c=1.227 in toluene). $^1$H, $^{31}$p and MS data were in accordance with those obtained for 1.

myo-Inositol 1,4,6-Trisphosphate (2)

Compound 11 (22,4 mg, 36 μmol) was treated with 0.5 N KOH (2 mL) to adjust the pH value to. 14. The solution was stirred at room temperature for 4 days. The reaction mixture was directly poured onto an ion-exchange column (Dowex 50 WX 8, $H^+$) for purification. Lyophilization gave compound 2 (5,8 mg, 39%).

$[\alpha]20_D$−8.49 (c=0.48 in MeOH). $^1$H-NMR ($D_2O$+6 eq. DIEA, 360 MHz): δ 3.35 (1H, dd, J=9.05, 9.05 Hz, H-5), 3.41-3.64 (1H, m, H-3, DIEA), 3.73 (1H, ddd, J=9.87, 9.87, 2.52 Hz, H-1), 3.90-4.11 (2H, m, H-4, H-6), 4.14 (1H, dd, J=2.33, 2.33 Hz, H-2). $^{31}$P-NMR ($D_2O$+6 eq. DIEA, $^1$H decoupled, 145.8 MHz): δ 4.32 (1P, s), 5.41 (1P, s), 5.67 (1P, s). MS: m/z (neg. mode, DCI) 159 [$(M-3[PO(OH)_2]^- -H_2O)^{3-}$; 90].

myo-Inositol 3,4,6-Trisphosphate (ent-2)

The free acid ent-11 (41,2 mg, 65 μmol) was saponified as described for compound 2 (12,7 mg, 46%). $[\ ]^{20}_D$+4.49 (c=0.85 in MeOH). $^1$H, $^{31}$P, and MS data were in accordance with those obtained for 2.

EXAMPLE 2

Synthesis of rac-(3aS, 4R, 5S, 6R, 7S, 7aS)-4,5,6,7-tetrakis[[bis(acetoxymethoxy)phosphoryl]oxy]-2,2-dimethyl-3a-propyl-hexahydrobenzo-(1,3)-dioxol (24)

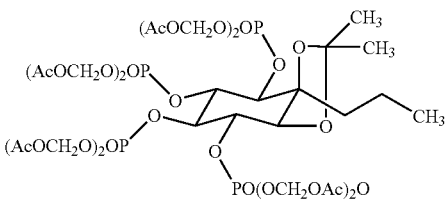

Figure 4:
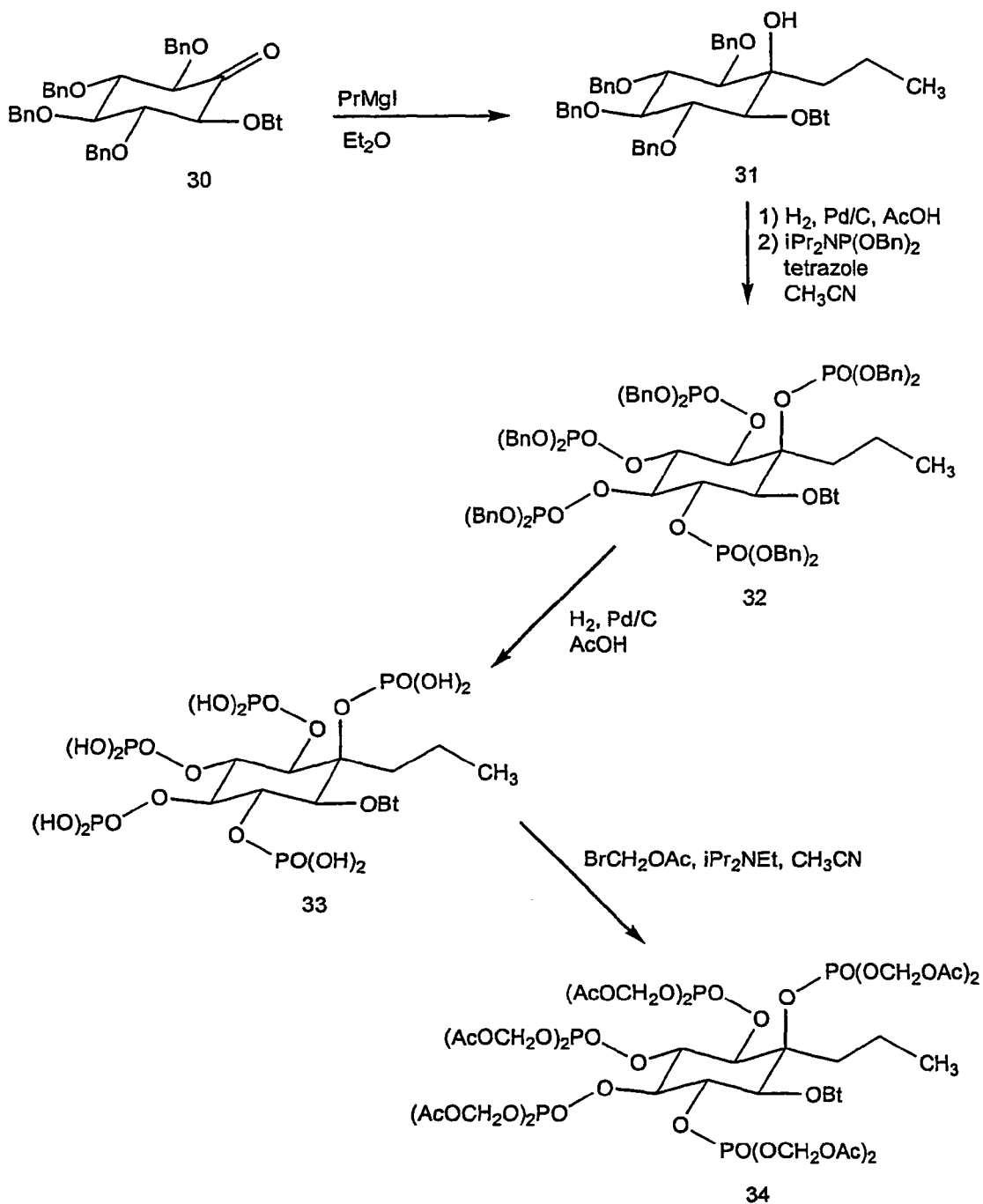
FIG. 4 is a reaction scheme showing a representative route for the synthesis of rac-(1S, 2R, 3S, 4R, 5S, 6S)-2,3,4,5,6-pentakis-[[bis(acetoxymethoxy)-phosphoryl]oxy]-6-butyroxy-2-propyl-cyclohexane (also referred to herein as "Compound D"), as described in Example 4.

Referring to the reaction scheme shown in FIG. 4, the compound rac-(3aS, 4R, 5S, 6R, 7S, 7aS)-4,5,6,7-tetrakis[[bis(acetoxymethoxy)phosphoryl]oxy]-2,2-dimethyl-3a-propyl-hexahydrobenzo-(1,3)-dioxol (24) was synthesized as follows:

Synthesis of rac-(1S, 2R, 3S, 4R, 5S, 6S)-6-allyloxy-2,3,4,5-tetrabenzyloxy-1-hydroxy-1-propyl-cyclohexane (20):

0.305 g Magnesium powder (12.6 mmol) was suspended in 15 mL dry diethyl ether under an argon atmosphere and 1.25 mL iodopropane (12.9 mmol) was added. After the initial boiling stopped the mixture was heated to reflux for another 15 min. In a second reaction vessel 0.83 g inosose 2 (1.43 mmol) was suspended in 10 mL dry diethyl ether and the Grignard mixture was added in portions under vigorous stirring and argon. After there was no starting material detectable by analytical HPLC (RP18, 1.5 mL/min, 90% MeOH, $t_{Ret}$=6.35 min) the reaction was quenched by adding water. The organic phase was diluted with t-butylmethyl ether and was washed with $Na_2SO_4$-solution (10%), 0.5 M phosphate buffer pH=7, and brine. The organic phase was dried over $Na_2SO_4$, filtered, and dried under reduced pressure. The residue was purified by preparative HPLC (RP18, 89% MeOH, 40 mL/min). 0.374 g ($t_{Ret}$=37.10 min, 0.60 mmol, 42% yield) of the equatorial alkylated product 20 was isolated as a colorless solid as well as 0.113 g ($t_{Ret}$=45.45 min, 0.20 mmol, 14.6% yield) of the axial alkylated epimner.

Equatorially alkylated epimer 20:

m.p.: 103.5° C.

$^1$H-NMR (200 MHz, $CDCl_3$): δ 7.51-7.28 (m, 20H, Ph), 6.18-5.96 (m, 1H, $OCH_2CHCH_2$), 5.43-5.20 (m, 2H, $OCH_2CHCH_2$), 5.194.67 (m, 8H, $CH_2Ph$), 4.63-4.51 and 4.30-4.17 (m, 2H. $OCH_2C_2H_3$), 4.17 (dd, 1H, $^3$J=9.7 Hz, H-5), 4.12 (dd, 1H, $^3$J=9.7 Hz, H-3), 3.61 (dd, 1H, $^3$J=9.6 Hz, H-4), 3.51 (d, 1H, $^3$J=9.3 Hz, H-6), 3.39 (d, 1H, $^3$J=9.3 Hz, H-2), 2.29 (br s, 1H, OH), 2.00-1.74 (m, 2H, $CH_2CH_2CH_3$), 1.50-1.08 (m, 2H, $CH_2CH_2CH_3$), 0.97 (t, 3H, $CH_2CH_2CH_3$, $^3$J=7.1 Hz, $CH_3$)

MS (neg. mode, FAB, NBA) m/z (%): 621 [$M-H^+$] (38), 531 [$M-Bn^+$] (100)

MS (pos. mode, FAB, NBA) m/z (%): 640 [M+NH$_4^+$] (100)

C$_{40}$H$_{46}$O$_6$ (622.80): calcd. C 77.14, H 7.44; found C 77.20, H 7.30

Axially alkylated epimer:

$^1$H-NMR (200 MHz, CDCl$_3$): δ 7.56-7.21 (m, 20H, Ph), 6.17-5.94 (m, 1H, OCH$_2$CHCH$_2$), 5.46-5.20 (m, 2H, OCH$_2$CHCH$_2$), 5.04-4.86 (m, 4H, CH$_2$Ph), 4.55-4.30 (OCH$_2$CHCH$_2$), 3.79-3.32 (m, 5H, H-2, H-3, H-4, H-5), 2.52 (br s, 1H, OH), 1.90-1.63 (m, 4H, CH$_2$CH$_2$), 1.13-0.97 (m, 3H, CH$_3$)

MS (neg. mode, FAB, NBA) m/z (%): 621 [M–H$^+$] (4), 531 [M–Bn$^+$+H$^{30}$] (2)

MS (pos. mode, FAB, NBA) m/z (%): 623 [M+H$^+$] (<1), 531 [Bn$^+$] (100)

Synthesis of rac-(1S, 2R, 3S, 4R, 5R, 6S)-2,3,4,5-tetrabenzyloxy-1,6-dihydroxy-1-propyl-cyclohexane (21)

20 (0.30 g, 0.48 mmol) was dissolved in 20 mL aqueous ethanol (90%). 93 mg (0.101 mmol) Wilkinson catalyst and 50 μL diisopropylethyl amine were added and the mixture was heated to reflux for 12 hours. After cooling to room temperature 30 μL triflouro acetic acid was added and the solution was allowed to stir for 12 days by when the starting material had disappeared. The solution was dried in high vacuum and the residue was dissolved in t-butylmethyl ether and washed with 0.5 M phosphate buffer pH=7 and brine. The organic phase was filtered after being dried over Na$_2$SO$_4$ and the filtrate was dried under reduced pressure. Further purification was accomplished by preparative HPLC (89% MeOH, 40 m/min, t$_{Ret}$=21.40 min) to give 220 mg of 21 (0.38 mmol, 78.4% yield) as a colorless oil.

$^1$H-NMR-(200 MHz, d$_6$-DMSO): δ 7.43-7.23 (m, 20H, Ph), 5.034.58 (m, 8H, CH$_2$-Bn), 4.02 (dd; 1H, $^3$J=9.4 Hz, H-5), 3.82 (dd, 1H, $^3$J=9.3 Hz, H-3), 3.52 (dd, 1H, $^3$J=9.6 Hz, H-4), 3.43 (d, 1H, $^3$J=9.4 Hz, H-2), 3.43 (dd, 1H, $^3$J=9.4 Hz, 5.1 Hz, H-6), 2.27 (d, 1H, $^3$J=5.1 Hz, OH), 2.18 (br s, 1H, OH), 1.87-1.59 (m, 2H, CH(Pr)), 1.47-0.94 (m, 2H, CH(Pr)), 0.87 (t, 3H, $^3$J=7.1 Hz, CH$_3$)

MS (neg. mode, FAB, NBA) m/z (%): 581 [M–H$^+$] (17), 491 [M–Bn$^+$] (4)

Synthesis of rac-(3aR, 4R, 5S, 6S, 7R, 7aS)-4,5,6,7-tetrabenzyloxy-2,2-dimethyl-3a-propyl-hexahydrobenzo-(1,3)-dioxol (22)

21 (0.22 g, 0.37 mmol) was dissolved in 20 mL dry acetone. 5 mL (40.8 mmol) 2,2-dimethoxypropane and 48 mg (0.25 mmol) p-toluene sulfonic acid were added an the solution was stirred for three days at room temperature. Then the reaction was stopped by adding 150 μL (1.08 mmole) triethylamine. All volatile components were removed under reduced pressure and the residue was dissolved in t-butylmethyl ether and washed with 0.5 M phosphate buffer pH=7 and brine. The organic phase was dried over Na$_2$SO$_4$, filtered and dried under reduced pressure. The residue was purified by preparative HPLC (RP18, 94% MeOH, 40 mL/min, t$_{Ret}$=35.10 min) to give 22 (160 mg, 0.25 mmol, 69.3% yield) as a slightly yellow oil.

$^1$H-NMR (200 MHz, CDCl$_3$): δ 7.52-7.18 (m, 20H, Ph), 4.85-4.49 (m, 8H, CH$_2$-Ph), 4.09 (dd, 1H, $^3$J=5.3 Hz, H-4), 4.01 (dd, $^3$J=7.3 Hz, $^3$J=0.3 Hz, H-7), 3.94 (dd, $^3$J=6.9 Hz, $^3$J=5.3 Hz, H-5), 3.67 (dd, $^3$J=7.0 Hz, H-6), 3.63 (dd, $^3$J=5.3 Hz, H-7a), 1.73-1.61 (m, 2H, CH(Pr)), 1.38-1.17 (m, 2H, CH(Pr)), –1.51 (s, 3H, CH$_3$), 1.42 (s, 3H, CH$_3$), 0.79 (t, 3H, $^3$J=7.3 Hz, CH$_3$Pr))

MS (pos. mode, DCI, NH$_3$) m/z (%): 640 [M+NH$_4^+$] (17)

MS (neg. mode, DCI, NH$_3$) m/z (%): 621 [M–H$^+$] (2), 531 [M–Bn$^+$] (28)

Synthesis of rac-(3aS, 4R, 5S, 6R, 7S, 7aS)-4,5,6,7-tetrakis [[bis(benzyloxy)-phosphoryl]oxy]-2,2-dimethyl-3a-propyl-cis-hexahydrobenzo-(1,3)-dioxol (23)

22 (160.8 mg, 0.258 mmol) was dissolved in 10 mL ice-cold ethanol (–20° C.) and palladium on charcoal (10%, 990 mg, 0.93 mmol) was added as a suspension in 10 mL ice-cold ethanol under argon. The mixture was subjected to a hydrogen atmosphere in a self-built hydrogenation apparatus. After a week of vigorous stirring the catalyst was filtered off and the filtrate dried under reduced pressure. The residue and 0.214 g tetrazole (3.06 mmol) were dissolved in 7 mL dry acetonitrile. Under argon 0.814 mL (2.42 mmol) dibenzyl N,N-diisopropyl phosphoramidite was added and the mixture was stirred for 48 hours before it was cooled –40° C. and 0.5 mL peracetic acid was carefully added. The solution was allowed to warm to room temperature and the volatile components were removed in high vacuum. Further purification by preparative HPLC (93% MeOH, 40 mL/min, t$_{Ret}$=21.5 min) gave 23 (36.7 mg, 22 μmol, 8.6% yield) as a colorless oil.

$^1$H-NMR (200 MHz, CDCl$_3$): δ 7.39-7.12 (m, 40H, Ph), 0.72 (t, 3H, CH$_3$), 5.27-4.76 (m, 20H, CH$_2$-Ph, H-4, H-5, H-6, H-7), 4.24 (d, 1H, $^3$J=5.2 Hz, H-7a), 1.89-1.66 (m, 2H, CH(Pr)), 1.48 (s, 3H, CH$_3$), 1.48-1.22 (m, 2H, CH(Pr)), 1.32 (s, 3H, CH$_3$), 0.73 (t, 3H, $^3$J=7.2 Hz, CH$_3$(Pr))

$^{31}$P-NMR (81 MHz, CDCl$_3$): δ –0.28 (2P), –0.78 (P), –0.98 (P)

MS (pos. mode, DCI, NH$_3$) m/z (%): 1303 [M+H$^+$] (100)

MS (neg. mode, DCI, NH$_3$) m/z (%):1301 [M–H$^+$] (9), 1210 [M–H$^+$–Bn] (100), 1121 [M–2*Bn$^+$+H$^+$] (49)

Synthesis of rac-(3aS, 4R, 5S, 6R, 7S, 7aS)4,5,6,7-tetrakis [[bis(acetoxymethoxy)-phosphoryl]oxy]-2,2-dimethyl-3a-propyl-hexahydrobenzo-(1,3)-dioxol (24)

Under an argon atmosphere 500 mg palladium on charcoal (10%, 0.47 mmol) were carefully suspended in 5 mL ice-cold ethanol (–20° C.) and 0.1 mL diisopropylethyl amine was added. 26 mg (20 μmol) of phosphorus triester 23 was added dissolved in 10 mL ice-cold ethanol. The mixture was subjected to a hydrogen atmosphere in a self-built hydrogenation apparatus. After a week of vigorous stirring the catalyst was filtered off and the filtrate dried under reduced pressure. The residue was dissolved in 1 mL dry acetonitrile under an argon atmosphere and 132 μl diisopropylethyl amine (98 μmole) and 178 μl acetoxymethyl bromide (178 μmol) were added. After 48 hours all volatile components were removed in high vacuum and the residual oil was subjected to preparative HPLC to give 9.2 mg of 24 (8 μmol, 39.7% yield) as a colorless oil.

$^1$H-NMR (200 MHz, d$_8$-toluene): δ 5.93-5.51 (m, 16H, OCH$_2$O), 5.47-5.28 (m, 2H, H-5, H-7), 5.17-5.97 (m, 2H, H-4, H-6), 4.24 (d, 1H, $^3$J=4.8 Hz, H-7a), 1.90 (s, 3H, OAc), 1.81 (s, 3H, OAc), 1.81 (2s, 6H, OAc), 1.78 (s, 3H, OAc), 1.76 (s, 3H, OAc), 1.76 (s, 3H, OAc), 1.75 (s, 3H, OAc), 1.70-1.51 (m, 2H, CH(Pr)), 1.54 (s, 3H, CH$_3$), 1.41-1.28 (m, 2H, CH(Pr)), 1.18 (s, 3H, CH$_3$), 1.03 (t, 3H, $^3$J=6.9 Hz, CH$_3$ (Pr))

$^{31}$P-NMR (81 MHz, d$_8$-toluene): δ –2.55 (2P), –3.34 (2P)

MS (pos. mode, FAB, NBA) m/z (%):1181 [M+Na$^+$] (5)

MS (neg. mode, FAB, NBA) m/z (%): 1085 [M–CH$_2$OAc$^+$] (6)

HR-MS: calcd. for C$_{33}$H$_{53}$O$_{32}$P$_4$ [M–CH$_2$OAc$^+$] 1085.1471, found 1085.1468

EXAMPLE 3

Synthesis of rac-(1S, 2R, 3S, 4R, 5S, 6S)-4,5,6,7-tetrakis[[bis(acetoxymethoxy)phosphoryl]oxy]-1-butyroxy-6-propoxy-1-propyl-cyclohexane (29)

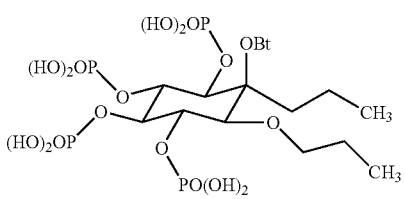

Referring to the reaction scheme shown in FIG. 5, the compound rac-(1S, 2R, 3S, 4R, 5S, 6S)-4,5,6,7-tetrakis[[bis(acetoxymethoxy)phosphoryl]oxy]-1-butyroxy-6-propoxy-1-propyl-cyclohexane (29) was synthesized as follows:

Synthesis of rac-(1S, 2R, 3S, 4R, 5S, 6S)-6-allyloxy-2,3,4,5-tetrabenzyloxy-1-butyroxy-1-propyl-cyclohexane (25)

348 mg (0.56 mmol) 20 were dissolved in 25 mL dry toluene. Under an argon atmosphere 2.5 mL (24 mmol) butyric acid anhydride and 250 μL phosphazene base-$P_1$-t-Bu (0.98 mmol) were added and the solution was refluxed for 18 hours. After cooling the solution was diluted with t-butylmethyl ether. The organic layer was extracted twice with phosphate buffer (0.5 M, pH 7), followed by brine, then dried over $Na_2SO_4$ and filtered. The solvent was removed under reduced pressure and the solid residue was recrystallized from methanol to give 25 (316 mg, 0.46 mmol, 81.4% yield) as a colorless solid.

m.p.: 115° C.

$^1$H-NMR (200 MHz, CDCl$_3$): δ 7.41-7.19 (m, 20H, Ph), 6.07-5.83 (m, 1H, CH$_2$CHCH$_2$), 5.31 (ddt, 1H, $^3$J=17.2 Hz, $^2$J=$^4$J=1.6 Hz, CH$_2$CHCHH), 5.16 (ddt, 1H, $^3$J=10.5 Hz), 5.03-4.69 (m, 8H, CH$_2$Ph), 4.52-4.10 (m, 2H, CH$_2$ CHCH$_2$), 3.95 (dd, 1H, $^3$J=9.4 Hz, H-3), 3.91 (dd, 1H, $^3$J=9.4 Hz, H-5), 3.52 (dd, 1H, $^3$J=9.5 Hz, H-4), 3.44 (d, 1H, $^3$J=9.4 Hz, H-6), 3.38 (d, $^3$J=9.4 Hz, H-1), 2.80-2.51 (m, 2H, α-CH$_2$(Bt)), 2.34 (t, 2H, $^3$J=7.3 Hz, C(OBt)CH$_2$), 1.82-1-54 (m, 2H, CH$_2$(Bt)), 1.39-1.10 (m, 2H, C(OBt)CH$_2$CH$_2$), 1.01 (t, 3H, $^3$J=7.2 Hz, CH$_3$), 0.90 (t, 3H, $^3$J=7.0 Hz, CH$_3$)

MS (negative mode, DCI, NH$_3$) m/z (%): 691 [M–H$^+$] (7), 651 [M–C$_3$H$_5$+] (2), 621 [M–Bt$^+$] (6), 601 [M–Bn$^+$] (17), 511 [M–2*Bn$^+$+H$^+$] (3)

C$_{44}$H$_{52}$O$_7$ (692.89): calcd. C 76.27H 7.56; found C 76.49H 7.41

Synthesis of rac-(1S, 2R, 3S, 4R, 5S, 6S)-2,3,4,5-tetrabenzyloxy-1-butyroxy-6-propoxy-1-propyl-cyclohexane (26)

The allyl ether 21 (182 mg, 0.26 mmol) was dissolved in a mixture of 7 mL ethanol and 1 mL acetone and 18 mg Wilkinson catalyst (19 μmol) was added. The mixture was stirred in a hydrogen atmosphere for 3 days, before the solvents were removed under reduced pressure. The residue was chromatographed by preparative HPLC (95% MeOH, 40 mL/min, $t_{Ret}$=35.00 min) to give 26 as a colorless solid(108 mg, 0.16 mmol; 59.2% yield).

m.p.: 114.5° C.

$^1$H-NMR (200 MHz, CDCl$_3$): δ 7.42-7.18 (m, 20H, Ph), 5.03-4.78 (m, 8H, CH$_2$Ph), 3.97-3.85 (m, 1H, OCHHCH$_2$), 3.94 (dd, 1H. $^3$J=9.4 Hz, H-5), 3.88 (dd, 1H, $^3$J=9.4 Hz, H-3), 3.54-3.44 (m, 1H, OCHHCH$_2$), 3.50 (dd, 1H, $^3$J=9.6 Hz, H-4), 3.46 (d, 1H, $^3$J=9.5 Hz, H-2), 3.33 (d, 1H, $^3$J=9.4 Hz, H-6), 2.82-2.51 (m, 2H, α-CH$_2$(Bt)), 2.33 (t, 2H, $^3$J=7.3 Hz, C(OBt)CH$_2$), 1.80-1.52 (m, 5H, CH$_2$), 1.38-1.13 (m, 3H, CH$_2$), 1.01 (t, 3H, $^3$J=7.3 Hz, CH$_3$), 0.95 (t, 3H, $^3$J=7.2 Hz, CH$_3$), 0.91 (t, 3H, J=7.2 Hz, CH$_3$)

MS (pos. mode, DCI, NH$_3$) m/z (%): 712 [M+NH$_4^+$] (23), 695 [M+H$^+$] (7), 91 [Bn$^+$] (100), MS (neg. mode, DCI, NH$_3$) m/z (%): 603 M–Bn$^+$ (100)

C$_{44}$H$_{54}$O$_7$ (694.91) calcd. C 76.05, H 7.83; found C 76.18, H 7.98

Synthesis of rac-(1S, 2R, 3S, 4R, 5S, 6S)-2,3,4,5-tetrakis[[bis(benzyloxy)-phosphoryl]oxy]-1-butyroxy-6-propoxy-1-propyl-cyclohexane (27a)

107 mg Palladium on charcoal (10%, 0.10 mmol) was added to a solution of 26 (95 mg, 0.16 mmol) in 7.5 mL glacial acetic acid. The mixture was kept under a hydrogen atmosphere for 12 hours and was stirred vigorously. Subsequently, the catalyst was removed by ultrafiltration and the filtrate was freeze-dried. The residue was dissolved in 3 mL acetonitrile under an argon atmosphere and 0.5 mL dibenzyl N,N-diisopropyl phosphoramidite (1.49 mmol) und tetrazole (117 mg, 1.67 mmol) were added. The mixture was stirred at room temperature for 12 hours, then cooled to –40° C. and treated with peracetic acid (32% w/w in acetic acid, 0.350 mL, 1.67 mmol). After the mixture reached room temperature all volatile components were removed in high vacuum and the residue was purified by preparative HPLC (90% MeOH, 40 mL/min). The chromatogram showed two major products. Accordingly, axially phosphorylated compound 27b (84 mg, 42% yield, $t_{Ret}$=48.3 min) and equatorially phosphorylated compound 27a (68 mg, 34% yield, $t_{Ret}$52.0 min) were isolated as colorless oils.

$^1$H-NMR (200 MHz, CDCl$_3$): δ 7.32-7.12 (m, 40H, Ph), 5.20-4.54 (m, 20H, CH$_2$-Ph, H-2, H-3, H-4, H-5), 3.84-3.68 (m, 1H, OCHHCH$_2$CH$_3$) 3.73 (d, $^3$J=7.0 Hz, H-6), 3.36-3.23 (m, 1H, OCHHCH$_2$CH$_3$), 2.69-2.25 (m, 2H, α-CH$_2$(Bt)), 2.20. (t, 2H, C(OBt)CH$_2$), 1.67-1.31 (m, 6H, CH$_2$), 0.88 (t, 3H, $^3$J=7.2 Hz, CH$_3$), 0.80 (t, 3H, $^3$J=7.5 Hz, CH$_3$) 0.76 (t, 3H, $^3$J=7.2 Hz, CH$_3$)

$^{31}$P-NMR (81 MHz, CDCl$_3$): δ 0.32 (1P), –0.16 (1P), –0.16 (1P), –0.47 (1P)

MS (neg. mode, DCI, NH$_3$) m/z (%): 1373 [M–H$^+$] (1), 1284 [M–Bn$^+$] (16)

Migration Product 27b:

$^1$H-NMR (200 MHz, CDCl$_3$): δ 7.58-7.10 (m, 40H, Ph), 5.34-4.80 (m, 19H, CH$_2$-Ph, H-2, H-3, H-5), 4.49 (ddd, 1H, J=10.1 Hz, H-4), 4.04-3.89 (m, 1H, OCMHCH$_2$CH$_3$), 3.44 (dd, 1H, J=9.8 Hz, 3.7 Hz, H-6), 3.32 (m, 1H, OCHHCH$_2$CH$_3$), 2.54-2.04 (m, 4H, α-CH$_2$(Bt), C$_1$CH$_2$), 1.90-1.08 (m, 6H), 0.94 (t, 3H, $^3$J=6.9 Hz, CH$_3$), 0.79 (t, 3H, $^3$J=7.7 Hz, CH$_3$), 0.75 (t, 3H, $^3$J=7.0 Hz, CH$_3$)

$^{31}$P-NMR (81 MHz, CDCl$_3$): δ 0.90 (1P), 0.33 (1P), –0.01 (1P), –5.62 (1P)

Synthesis of rac-(1S, 2R, 3S, 4R, 5S, 6S)-1-butyroxy-4,5,6,7-tetrakis(phosphonooxy)-6-propoxy-1-propyl-cyclohexane (28)

27a (73 mg, 53 μmols) was dissolved in 4 mL glacial acetic acid and 130 mg palladium on charcoal (10% Pd, 0.12 mmol) was added. The mixture was kept under a hydrogen atmosphere for 12 hours and was stirred vigorously. Subsequently, the catalyst was removed by ultrafiltration and the filtrate was freeze-dried to give 28 (35 mg, 99% yield) as a colorless oil.

$^1$H-NMR (200 MHz, DMSO-d$_6$): δ 4.53-4.20 (m, 4H, H-2, H-3, H-4, H-5), 3.97-3.81 (m, 1H, OCHH), 3.60 (d, 1H, $^3$J=9.3 Hz, H-6), 3.41-3.22 (m, 1H, OCHH), 2.66-2.23 (m, 2H, α-CH$_2$(Bt)), 2.17 (t, 2H, $^3$J=7.3 Hz, C(OBt)CH$_2$), 1.65-

1.35 (m, 4H, CH$_2$), 1.27-1.05 (m, 2H, CH$_2$), 0.87 (t, 3H, $^3$J=6.9 Hz, CH$_3$), 0.85 (t, 3H, $^3$J=6.5 Hz, CH$_3$), 0.84 (t, 3H, $^3$J=7.1 Hz, CH$_3$)

$^{31}$P-NMR (81 MHz, DMSO-d$_6$): δ 0.78 (1P), 0.43 (1P), −0.05 (1P), −0.12 (1P)

MS (pos. mode, FAB, NBA) m/z (%): 655 [M−H$^+$] (<1), 585 [M−Bt$^+$+2H$^+$] (<1)

MS (neg. mode, FAB, NBA) m/z (%): 653 [M−H$^+$] (24), 97 [H$_2$PO$_3^-$] (27)

Synthesis of rac-(1S, 2R, 3S, 4R, 5S, 6S)4,5,6,7-tetrakis[[bis(acetoxymethoxy)-phosphoryl]oxy]-1-butyroxy-6-propoxy-1-propyl-cyclohexane (29)

23 mg Tetrakisphosphate 28 (35 μmol) was dissolved in 1 mL acetonitrile under an argon atmosphere and 17 μl diisopropylethyl amine (0.69 nmol) and 69 μl acetoxymethyl bromide (0.69 mmol) were added. The solution was stirred for 48 hours at room temperature when all volatile components were removed in high vacuum. The residue was purified by preparative HPLC (40 mL/min, 70% MeOH, t$_{Ret}$=32.0 min) to give 29 (20 mg, 46.7% yield) as a colorless oil.

$^1$H-NMR (200 MHz, toluene-d$_8$): δ 6.02-5.53 (m, 8H, OCH$_2$O), 5.13-4.89 (m, 2H, H-3, H-5), 4.74-4.54 (m, 2H, H-2, H-4), 4.08-3.92 (m, 1H, OCHHCH$_2$CH$_3$), 3.36-3.19 (m, 1H, OCHHCH$_2$CH$_3$), 3.19 (d, 1H, $^3$J=8.9 Hz, H-6), 3.03-2.54 (m, 2H, α-CH$_2$(Bt)), 2.35-2.21 (m, 2H, C(OBt)CH$_2$), 1.92-1.53 (m, 6H, CH$_2$), 1.92 (s, 6H, 2Ac), 1.84 (s, 3H, Ac), 1.81 (s, 6H, 2Ac), 1.78 (s, 3H, Ac), 1.75 (s, 3H, Ac), 1.74 (s, 3H, Ac), 1.00 (t, 3H, $^3$J=7.4, CH$_3$), 0.92 (t, 3H, $^3$J=7.4, CH$_3$)

$^{31}$P-NMR (81 MHz, toluene-d$_8$): δ 2.79 (1P), −3.02 (1P), −3.27 (1P), −3.68 (1P)

MS (neg. mode, FAB, NBA) m/z (%): 1157 [M−CH$_2$OAc$^+$] (7), 1085 [M−2 CH$_2$OAc$^+$+H$^+$] (11), 241 [(AcOCH$_2$O)$_2$PO$_2$] (97)

HR-MS: calcd. for C$_{37}$H$_{61}$O$_{33}$P$_4$ 1157.2046, found 157.2046

EXAMPLE 4

Synthesis of rac-(1S, 2R, 3S, 4R, 5S, 6S)-2,3,4,5,6-pentakis-[[bis(acetoxymethoxy)phosphoryl]oxy]-6-butyroxy-2-propyl-cyclohexane (34)

Referring to the reaction scheme shown in FIG. 6, the compound rac-(1S, 2R, 3S, 4R, 5S, 6S)-2,3,4,5,6-pentakis-[[bis(acetoxymethoxy)phosphoryl]oxy]-6-butyroxy-2-propyl-cyclohexane (34) was synthesized as follows:

Synthesis of rac-(1R, 2R, 3S, 4S, 5R, 6S)-2,3,4,5-tetra(benzyloxy)-6-butyroxy-1-hydroxy-1-propyl-cyclohexane (31)

Magnesium powder (0.968 g, 40 mmol) was overlayed with 50 mL dry diethyl ether and 3.8 mL iodopropane (39 mmol) was added. The reaction was started by adding some iodine crystals and after the boiling slowed, the mixture was held under reflux for 15 min.

The inosose 30 (0.938 g, 1.54 mmol) was suspended in 20 mL diethyl ether and 2 mL of the freshly prepared Grignard reagent was added under an argon atmosphere. After 3 hours the reaction was quenched by adding ice and ethyl acetate. The organic layer was washed with aqueous Na$_2$SO$_3$ (0.1 M), phosphate buffer (pH 7), and brine. After drying over Na$_2$SO$_4$ and filtration the solvent was removed under reduced pressure. The residue was prepurified by flash chromatography (n-hexane/ethyl acetate 3:1 v/v, silica 60, TLC: R$_f$ 0.2). The combined product-containing fractions were dried and N was purified by preparative HPLC (89% MeOH, 40 mL/min, t$_{Ret}$=35.5 min) to give the colorless solid 31 (127 mg, 0.20 mmol, 12.6% yield).

m.p.: 143.3° C.

$^1$H-NMR (200 MHz, CDCl$_3$): 7.57-7.21 (m, 20H, Bn), 5.17 (d, 1H, $^3$J=10.0 Hz, H-6), 5.13-4.69 (m, 8H, CH$_2$Bn), 4.12 (dd, 1H, $^3$J=9.4 Hz, H-3), 4.10 (dd, 1H, 3j=9.7 Hz, H-5), 3.70 (dd, 1H, $^3$J=9.5 Hz, H-4), 3.59 (d, 1H, $^3$J=9.3 Hz, H-2), 2.54-2.19 (m, 2H, α-CH$_2$(Bt)), 1.92-1.08 (m, 6H, CH$_2$), 0.99 (t, 3H, $^3$J=7.3 Hz, CH$_3$), 0.89 (t, 3H, J=6.9 Hz, CH$_3$)

MS (pos. mode, FAB, NBA) in/z (%): 653 [M+H$^+$] (1), 635 [M+H$^+$−H$_2$O] (3), 91 [Bn$^+$]3 (100)

MS (neg. mode, FAB, NBA) m/z (%): 651 [M−H$^+$] (<1), 582 [M−Bt$^+$] (4)

C$_{41}$H$_{48}$O$_7$ (652.83): calcd. C 75.43, H 7.41; found C 74.87H 7.30

Synthesis of rac-(1S, 2R, 3S, 4R, 5S, 6S)-1,2,3,4,5-6-butyroxy-pentakis-[[bis(benzyloxy)phosphoryl]oxy]-2-propyl-cyclohexane (32)

The tetrabenzyl ether 31 (109 mg, 0;17 mmol) was dissolved in 5 mL glacial acetic acid and 130 mg palladium on charcoal (10%, 0.12 mmol) was added. The mixture was stirred vigorously under a hydrogen atmosphere for 18 hours. The catalyst was removed by ultrafiltration and the filtrate was freeze-dried to give a white foam. The latter was dissolved in 3 mL dry acetonitrile and 92 mg tetrazole (1.31 mmol) and 345 μL dibenzyl N,N-diisopropylphosphoramidite (1.03 mmol) were added and the solution was stirred over night. Then all volatile components were removed in high vacuum and the residue was purified by preparative HPLC (92% MeOH, 40 mL/min, t$_{Ret}$=36.5 min) to give 32 (107 mg, 67 μmol, 39.4% yield) as a colorless oil.

$^1$H-NMR (200 MHz, CDCl$_3$): δ 7.45-7.09 (m, 45H, Ph), 5.26-4.79 (m, 23H, CH$_2$-Ph, H-3, H-5, H-6), 4.65 (td, 1H, J=10.4 Hz, 3.5 Hz, H-2), 4.43 (ddd, 1H, J=10.1 Hz, H-4), 2.60-2.40 (m, 1H, α-CHH(Bt)), 2.39-1.98 (m, 3H, C(OPO(Bn)$_2$)CH$_2$, α-CHH(Bt)), 1.61-1.16 (m, 3H, CH), 1.02-0.82 (m, 1H, CH), 0.74 (t, 3H, $^3$J=7.4 Hz, CH$_3$), 0.72 (t, 3H, $^3$J=6.6 Hz, CH$_3$)

$^{31}$P-NMR (81 MHz, CDCl$_3$): δ 0.75 (1P), 0.72 (1P), −0.01 (1P), −0.14 (1P), −5.52 (1P)

MS (pos. mode, DCI, NH$_3$) m/z (%): 1593 [M+H$^+$] (<1), 91 [Bn$^+$] (18)

MS (neg. mode, DCI, NH$_3$) m/z (%): 1501 [M−Bn$^+$] (2), 1411 [M−2 Bn$^+$+H$^+$] (<1), 1301 [M−3 Bn$^+$+2H$^+$] (<1), 1131 [M−3 Bn$^+$−Bt$^+$+3H$^+$] (2)

Synthesis of rac-(1S, 2R, 3S, 4R, 5S, 6S)-6-butyroxy-1,2,3,4,5-pentakis(phosphonooxy)-2-propyl-cyclohexane (33)

50 mg (31 μmol) fully protected pentakisphosphate 32 was dissolved in 5 mL glacial acetic acid, 14 mg palladium on charcoal (10% Pd, 13 μmol) was added, and the mixture was held under an hydrogen atmosphere for 12 hours. The catalyst was removed by ultrafiltration and the filtrate was freeze-dried to give 33 (21 mg, 30 μmol, 99% yield) as a white foam.

$^1$H-NMR (200 MHz, DMSO-d$_6$): δ 5.09 (dd, 1H, $^3$J=9.7 Hz, J=2.0 Hz, H-6), 4.68-4.21 (m, 4H, H-2, H-3, H-4, H-5), 2.42-2.27 (m, 2H, α-CH$_2$(Bt)), 2.27-2.12 (m, 1H, CH(Pr)), 1.941.74 (m, 1H, CH(Pr)), 1.69-1.47 (m, 2H, β-CH$_2$(Bt)), 1.35-1.11 (m, 2H, CH(Pr)), 0.87 (t, 3H, $^3$J=7.5 Hz, CH$_3$(Bt)), 0.76 (t, 3H, $^3$J=7.5 Hz, CH$_3$(Pr))

31P-NMR (81 MHz, DMSO-d$_6$): δ 0.74 (1P), 0.41 (1P), 0.01 (1P), −0.23 (1P), 4.9.7 (1P)

MS (pos. mode, FAB, NBA) m/z (%): 737 [M+2 Na$^+$−H$^+$] (1), 715 [M+Na$^+$] (1), 693 [M+H$^+$] (<1), MS (neg. mode, FAB, NBA) m/z (%): 713 [M+Na$^+$−2H$^+$] (17), 691 [M−H$^+$] (16), 97 [H$_2$PO$_3^-$] (34)

Synthesis of rac-(1S, 2R, 3S, 4R, 5S, 6S)-2,3,4,5,6-pentakis-[[bis(acetoxymethoxy)-phosphoryl]oxy]-6-butyroxy-1-propyl-cyclohexane (34)

8 mg Pentakisphosphate 33 (12 μmol) was dissolved in 0.75 mL dry acetonitrile under an argon atmosphere and 0.1 mL diisopropylethyl amine (589 μmol) and 60 μl (600 μmol) acetoxymethyl bromide were added. After stirring the solution for three days in the dark all volatile components were removed in high vacuum and the residue was subjected to preparative HPLC (68% MeOH, 40 mL/min, $t_{Ref}$=25.0 min) for purification 34 (11 mg, 8 μmoles, 71% yield) was isolated as a colorless oil.

$^1$H-NMR (200 MHz, toluene-d$_8$): δ 6.02-5.53 (m, 20H, OCH$_2$O), 5.26-4.98 (m, 3H, H-3, H-5, H-6), 4.73-4.44 (m, 2H, H-2, H-4), 2.83-2.24 (m, 4H, α-CH$_2$(Bt), CH(Pr)), 1.68-1.23 (m, 4H, CH(Pr)), 1.97 (s, 3H, OAc), 1.93 (s, 3H, OAc), 1.86 (s, 3H, OAc), 1.86 (2s, 6H, OAc), 1.85 (s, 3H, OAc), 1.84 (s, 3H, OAc), 1.83 (s, 3H, OAc), 1.80 (s, 3H, OAc), 1.78 (s, 3H, OAc), 1.10 (t, 3H, $^3$J=7.0 Hz, CH$_3$(Pr)), 0.99 (s, 3H, $^3$J=7.3 Hz, CH$_3$(Bt))

$^{31}$P-NMR (81 MHz, toluene-d$_8$): δ−2.89 (1P), −2.93 (1P), −3.14 (1P), −3.52 (1P), −8.70 1P)

MS (neg. mode, FAB, NBA) m/z (%): 1339 [M−CH$_2$Ac$^+$] (11), 241 [(AcOCH$_2$O)$_2$PO$_2^-$] (100)

HR-MS: calcd. for C$_{40}$H$_{64}$O$_{40}$P$_5$ 1339.1662; found 1339.1680

EXAMPLE 5

(5aα,6α,7β,8α,9β,9aα)-6,7,8,9-tetrakis[[bis(acetoxymethoxy)phosphoryl]oxy]-5a-[(2'-methoxy)ethoxy]methoxy-decahydro-benzo[b]oxepin (12)

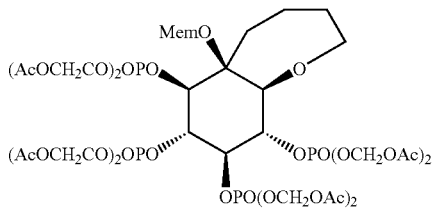

Figure 2:
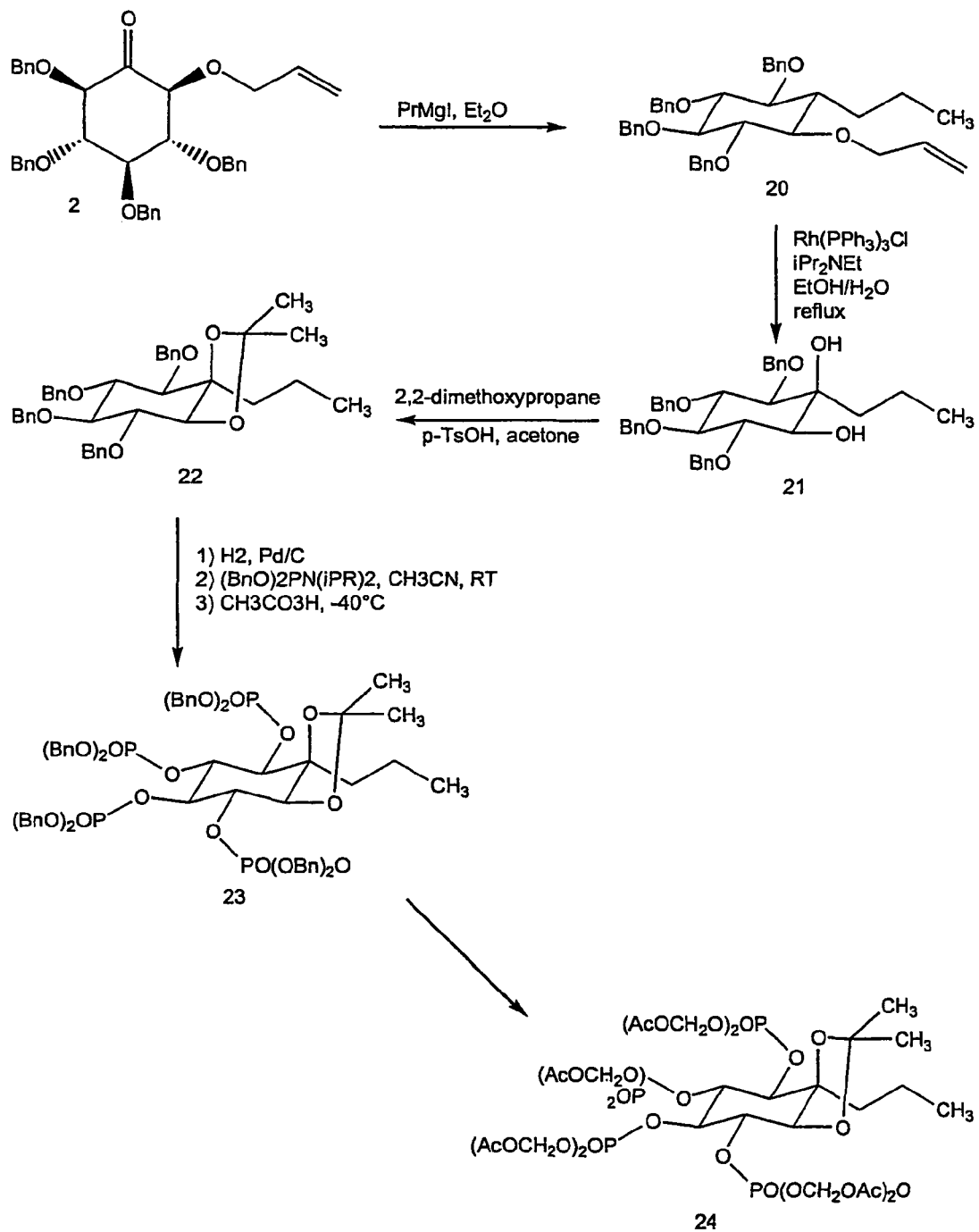
FIG. 2 is a reaction scheme showing a representative route for the synthesis of rac-(3aS, 4R, 5S, 6R, 7S, 7aS)-4,5,6,7-tetrakis[[bis(acetoxymethoxy)-phosphoryl]oxy]-2,2-dimethyl-3a-propyl-hexahydrobenzo-(1,3)-dioxol (also referred to herein as "Compound B"), as described in Example 2.

Referring to the reaction scheme shown in FIG. 2, the compound (5aα,6α,7β,8α,9β,9aα)-6,7,8,9-tetrakis[[bis(acetoxymethoxy)phosphoryl]oxy]-5a-[(2'-methoxy)ethoxy]methoxy-decahydro-benzo[b]oxepin (12) was synthesized as follows:

(5aα,6α,7β,8α,9β,9aα)-6,7,8,9-tetra(benzyloxy)-5a-hydroxy-decahydro-benzo[b]oxepin (9)

4 (0.684 g, 1.156 mmol) and dichloro tris(triphenylphosphine) ruthenium(II) (81 mg, 0.085 mmol) were suspended in 18 mL degased methanol under argon. The mixture was heated to reflux in the dare After the solution turned homogenous 18 mg sodium borohydride (0.48 mmol) were added and the solution was held under reflux for another four hours. After cooling to room temperature the solution was stirred for another 12 hours and finally dried under reduced pressure. The residue was resuspended in 7.5 mL acetonitrile and 10 mL CH$_2$Cl$_2$. Then 0.14 mL trifluoro acetic acid were added and the mixture was stirred for 5 days at room temperature. The reaction was quenched by adding 0.3 mL diisopropylethyl amine. All volatile components were removed under reduced pressure and the dry residue was dissolved in t-butylmethyl ether, extracted with phosphate buffer (pH 7) and brine. The organic phase was dried over Na$_2$SO$_4$, filtered and the solvent was evaporated. Preparative HPLC (84% MeOH, 40 mL/min, $t_{Ref}$=41.1 min) gave 0.433 g (63% yield) of 9 as a white solid and 0.170 g (25% yield) of the tricyclic compound 5.

m.p.: 130° C.

$^1$H-NMR (200 MHz, CDCl$_3$): δ 7.59-7.22 (m, 20H, Ph), 5.09-4.66 (m, 8H, CH$_2$Ph), 4.10 (dd, 1H, $^3$J=9.6 Hz, H-9), 4.03-3.84 (m, 2H, H-2), 3.01 (dd, 1H, $^3$J=9.1 Hz, H-7), 3.59 (d, 1H, $^3$J=9.6 Hz, H-8), 3.39 (d, 1H, $^3$J=9.2, H-6), 3.29 (d, 1H, $^3$J=9.2 Hz, H-9a) 2.57 (s, 1H, OH), 2.41-2.24 (m, 1H, oxepane), 2.13-1.59 (m, 4H, oxepane), 1.46-1.26 (m, 1H, oxepane)

$^{13}$C-NMR (50.3 MHz, CDCl$_3$): δ 139.47 (C), 139.26 (C), 139.19 (C), 138.62 (C), 84.25 (CH), 83.41 (CH), 83.01 (CH), 82.84 (CH), 82.27 (CH), 76.78 (CH$_2$), 76.74 (CH$_2$), 76.43 (C), 76.42 (CH$_2$), 76.37 (CH$_2$), 69.79 (CH$_2$), 41.11 (CH$_2$), 30.03 (CH$_2$), 19.74 (CH$_2$)

MS (pos. mode, DCI, NH$_3$) m/z (%): 612 [M+NH$_4^+$] (100), 595 [M+H$^+$] (6), 577 [M+H$^+$−H$_2$O] (13), 91 [Bn$^+$] (77)

MS (neg. mode, DCI, NH$_3$) m/Z (%): 593 [M−H$^+$] (2), 503 [M−Bn$^+$] (5)

C$_{38}$H$_{42}$O$_6$ (594.75): calcd. C 76.74, H 7.12; found C 76.75, H 7.08

Synthesis of (5aα,6α,7β,8α,9β,9aα)-6,7,8,9-tetra(benzyloxy)-5a-[(2'-methoxy)ethoxy]methoxy-decahydro-benzo[b]oxepin (10)

9 (0.397 g, 0.669 mmol) was dissolved in 6 mL dry dimethyl formamide. Sodium hydride (57 mg, 2.375 mmol) was added under vigorous stirring. After 45 min (0.130 ml, 1.148 mmol) 2-methoxy ethoxymethyl chloride was added and after 12 hours additional sodium hydride (82 mg, 3.417 mmol) and 2-methoxy ethoxymethyl chloride was supplied. After 90 min the reaction mixture was quenched and dried in high vacuum. The residue was suspended in t-butylmethyl ether and washed with phosphate buffer (pH 7) followed by brine. The organic layer was dried with Na$_2$SO$_4$ and filtered. The filtrate was dried under reduced pressure und the residue was chromatographed by preparative HPLC (88% MeOH, 40 mL/min, $t_{Ref}$=47.48 min) to give 0.393 g of 10 (86% yield) as a colorless oil.

$^1$H-NMR (200 MHz, CDCl$_3$): δ 7.42-7.21 (m, 20H, Ph), 5.27-5.04 (AB, 2H, $^2$J=6.8 Hz, OCH$_2$O), 5.02-4.55 (m, 8H, CH$_2$Ph), 4.16-3.62 (m, 2H, H-2), 4.02 (dd, 1H, $^3$J=9.5 Hz, H-7), 3.95 (dd, 1H, $^3$J=9.4 Hz, H-9), 3.93-3.76 (m, 2H, OCH$_2$CH$_2$O), 3.62-3.54 (m, 2H, OCH$_2$CH$_2$O), 3.51 (dd, 1H, $^3$J=9.2 Hz, H-8), 3.40 (s, 1H, OCH$_3$), 3.23 (d, 1H, $^3$J=9.4, H-9a), 3.19 (d, 1H, $^3$J=9.8 Hz, H-6), 2.52-2.36 (m, 1H, oxepane), 1.96-1.57 (m, 4H, oxepane), 1.52-1.42 (m, 1H, oxepane).

$^{13}$C-NMR (CDCl$_3$): δ 139.5 (C), 139.3 (C), 139.0 (C), 138.8(C), 91.5 (CH$_2$), 85.1 (CH), 84.4 (CH), 84.4 (CH), 83.4 (CH), 82.3 (CH), 82.1 (C), 76.6 (CH$_2$), 76.3 (CH$_2$), 76.3 (CH$_2$), 76.3 (CH$_2$), 72.3 (CH$_2$), 71.8 (CH$_2$), 67.6 (CH$_2$), 59.4 (CH$_3$), 34.0 (CH$_2$), 31.5 (CH$_2$), 21.1 (CH$_2$)

MS (pos. mode, DCI, NH$_3$) m/z (%): 700 (100) [M+NH$_4^+$], 610 (19) [M+NH$_4^+$−Bn$^+$+H$^+$]593 (14) [M+2H$^+$−Bn$^+$], 91 (96) [Bn$^+$]

MS (neg. mode, DCI, NH$_3$) m/z (%): 591 (14) [M−Bn$^+$], 501 (15) [M−2Bn$^+$+H$^+$]

HR-MS: calcd. for C$_{35}$H$_{43}$O$_8$ [M−C$_7$H$_7^+$] 591.2958, found 591.2934

Synthesis of (5aα,6α,7β,8α,9β,9aα)-6,7,8,9-tetrakis[[bis(benzyloxy)phosphoryl]-oxy]-5a-[(2'-methoxy)ethoxy]methoxy-decahydro-benzo[b]oxepin (11)

10 (0.381 g, 0.559 mmol) was dissolved in 5 mL ethanol and 0.05 mL diisopropyl ethylamine and palladium on charcoal (10% Pd, 0.379 g, 0.356 mmol) was added under an argon atmosphere at −20° C. The argon atmosphere was exchanged to hydrogen in a self-built hydrogenation apparatus and the mixture was stirred for seven days at room temperature. Finally, the hydrogen was exchanged to argon and the catalyst was removed by ultrafiltration. The filtrate was dried under reduced pressure. To the foamy residue 390 mg tetrazole (5.57 mmol) dissolved in 14 mL dry acetonitrile was added. Under argon, 1.85 mL (5.5 mmol) dibenzyl N,N-diisopropylphosphoramidite was added and the mixture was stirred for 18 hours. The mixture was cooled to −40° C. and 1.2 mL peracetic acid (32% wt. 5.755 mmol) were added. The solution was allowed to warm to room temperature and the volatile components were removed in high vacuum. The oily residue was purified by preparative HPLC (90% MeOH, 40 mL/min, $t_R$=3 1.4 min) to give 11 (265 mg, 46% yield) as a colorless oil.

$^1$H-NMR (200 MHz, CDCl$_3$): δ 7.42-7.09 (m, 40H, Ph), 5.20-4.79 (m, 20H, CH$_2$Ph; OCH$_2$O, H-7, H-9), 4.47 (q, 1H, $^3J$=9.8 Hz=$^4J_{PH}$=9.8 Hz, H-0.8), 4.23 (dd, 1H, $^3J$=10.2 Hz, H-H-6), 3.82-3.53 (m, 4H, OCH$_2$CH$_2$O, OCH$_2$-oxepane), 3.48-3.41 (m, 2H, OCH$_2$CH$_2$O), 3.32 (s, 3H, OCH$_3$), 3.23 ((d, 1H, $^3J$=9.5 Hz, H-9a) 2.55-2.40 (m, 1H, oxepane), 1.91-1.87 (m, 5H, oxepane).

$^{13}$C-NMR (50.3 MHz, CDCl$_3$): δ 91.2 (CH$_2$), 81.0 (CH), 80.5 (CH), 78.5 (CH), 77.1 (CH), 75.7 (CH) 59.3 (CH$_3$) 33.9 (CH$_2$), 30.5 (CH$_2$), 21.2 (CH$_2$), $^{31}$P-NMR (81 MHz, CDCl$_3$): δ 1.00 (1P), 0.61 (1P), 0.33 (1P), −0.43 (1P)

MS (pos. mode, DCI, NH$_3$) m/z (%): 1363 (3) [M+H$^+$], 91 (40) [Bn$^+$]

MS (neg. mode, DCI, NH$_3$) m/z (%): 1271 (6) [M−Bn$^+$], 277 (36) [OP(OBn)$_2$O]

HR-MS: calcd. for C$_{63}$H$_{71}$O$_{20}$P$_4$ [M−C$_7$H$_7$$^+$) 1271.3489, found 1271.3455

Synthesis of (5aα,6α,7β,8α,9β,9aα)-6,7,8,9-tetrakis[[bis (acetoxymethoxy)-phosphoryl]oxy]-5a-[(2'-methoxy) ethoxy]methoxy-decahydro-benzo[b]oxepin (12)

11 (170 mg, 0.125 mmol) was dissolved in 5 mL ethanol, containing 0.2 mL (1.18 mmol) diisopropylethyl amine and 319 mg Pd on charcoal (10% Pd, 3.0 mmol) suspended in ice-cold ethanol (5 mL) under argon was added. The argon atmosphere was exchanged to hydrogen in a self-built hydrogenation apparatus and the mixture was stirred for seven days at room temperature. Finally, the hydrogen was exchanged to argon and the catalyst was removed by ultrafiltration. The filtrate was dried under reduced pressure. The diisopropylethyl ammonium salt of the tetrakisphosphate was dried thoroughly and dissolved in 3 mL dry acetonitrile. Diisopropylethyl amine (0.42 mL, 2.474 mmol) and acetoxymethyl bromide (0.25 mL, 2.5 mmol) were added under argon and the mixture was allowed to stir for 48 hours in the dark at room temperature. All volatile ingredients were removed in high vacuum and the crude product was purified by preparative HPLC (58% MeOH, 40 mL/min, $t_{Ret}$=33.0) to give 12 (0.106 mg, 0.087 mmole, 70% yield) as a colorless oil.

$^1$H-NMR (200 MHz, d$_8$-toluene): δ 6.43-5.99 (m, 16H, OCH$_2$O), 5.55-5.24 (m, 4H, H-7, H-9, OCH$_2$O-MEM), 5.06 (ddd, 1H, J=9.5 Hz, H-8), 4.73 (dd, 1H, $^3J$=10.2 Hz, H-6), 4.31-3.80 (m, 6H, H-2, OCH$_2$CH$_2$O) 3.62 (s, 3H, OCH$_3$), 3.31 (d, 1H, $^3J$=9.5 Hz, H-9a), 2.97-2.78 (m, 1H, oxepane), 2.39-2.24 (m, 2H, oxepane), 2.30 (s, 3H, Ac), 2.30 (s, 3H, Ac), 2.26 (s, 3H, Ac), 2.26 (s, 3H, Ac), 2.23 (s, 3H, Ac), 2.20 (s, 3H, Ac), 2.19 (s, 3H, Ac), 2.18 (s, 3H, Ac), 2.03-1.73 (m, 3H, oxepane).

$^{13}$C-NMR (50.3 MHz, d$_8$-toluene): δ 169.85 (C), 169;64 (C), 169.64 (C), 169.58 (C), 169.58 (C), 169.54 (C), 169.43 (C), 169.34 (C), 91.91 (CH$_2$), 84.21-83.14 (CH$_2$), 81.24 (C), 80.82 (CH), 80.27 (CH), 79.34 (CH), 77.87 (CH), 76.79 (CH), 72.63 (CH$_2$), 71.70 (CH$_2$), 68.71 (CH$_2$), 58.99 (CH$_3$), 34.16 (CH$_2$), 30.87 (CH$_2$), 21.22 (CH$_2$).

$^{31}$P-NMR (81 MHz, d$_6$-DMSO): δ−3.01 (1P), −3.05 (2P), −3.07 (1P)

MS (neg. mode, FAB, NBA) m/z (%): 1145 [M−CH$_2$OAc$^+$] (7), 1073 [M−2CH$_2$OAc$^+$+H$^+$] (2), 241 [(AcOCH$_2$O)$_2$PO$_2$] (100)

MS (pos. mode, FAB, NBA) m/z (%): 1240 [M+Na$^+$] (4), 1147 [M+2H$^+$−CH$_2$OAc$^+$] (12)

HR-MS: calcd. for C$_{35}$H$_{57}$O$_{34}$P$_4$ [M−CH$_2$OAc$^+$] 1145.1672, found 1145.1696

EXAMPLE 6

Synthesis of (4aα, 5α,6β,7α,8β, 8aα)-5,6,7,8-tetrakis[[bis(acetoxymethoxy)phosphoryl]oxy]-4a-butyryloxy-octahydro-chromen (19)

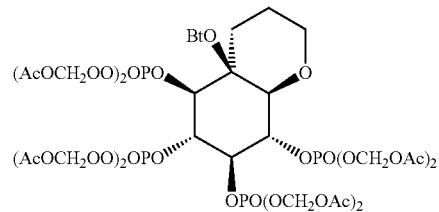

Figure 3:
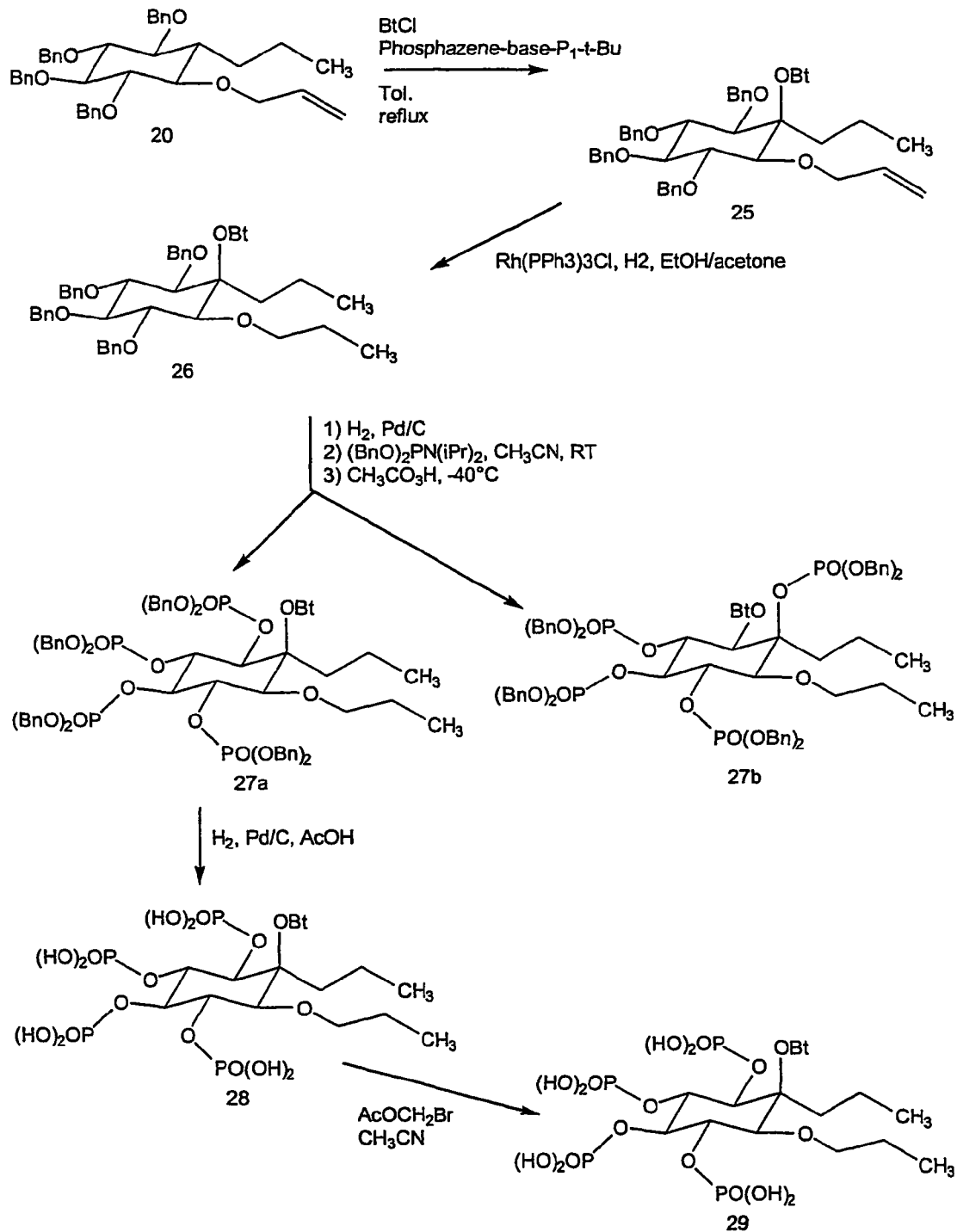
FIG. 3 is a reaction scheme showing a representative route for the synthesis, of rac-(1S, 2R, 3S, 4R, 5S, 6S)4,5,6,7-tetrakis[[bis(acetoxy ethoxy)-phosphoryl]oxy]-1-butyroxy-6-propoxy-1-propyl-cyclohexane (also referred to herein as "Compound A"), as described in Example 3.

Referring to the reaction scheme shown in FIG. 3, the compound (4aα, 5α,6β,7α,8β,8aα)-5,6,7,8-tetrakis[[bis(acetoxymethoxy)phosphoryl]oxy]-4a-butyryloxy-octahydrochromen (19) was synthesized as follows:

Synthesis of rac-(1S, 2R, 3S, 4R, 5S, 6S)-6-allyloxy-2,3,4,5-tetra-benzyloxy-1-hydroxy-1-vinyl cyclohexane(13)

341 mg 2 (0.59 mmol) were suspended in 20 mL absolute diethyl ether and the mixture was cooled to 40° C. Under an argon atmosphere 0.65 mL (1.12 mmol) of a 1.7 M solution of vinylmagnesium chloride in THF was added in two equal portions. The solution was stirred for 18 hours at room temperature, when the reaction was quenched by adding 10 mL phosphate buffer (0.5 M, pH 7).

The organic layer was diluted with t-butylmethyl ether, washed twice with phosphate buffer and brine, dried over anhydrous sodium sulfate, and filtered. The volatile components were removed under reduced pressure. From the oily residue the two 2-hydoxy epimers were purified by preparative HPLC (RP-18, 40 mL/min, 88% MeOH, $t_{Ret}$=32.05 min and 36.40 min, respectively) to give epimer 13 with the axial hydroxy group in 29% (0.104 g, 0.17 mmol) as a colorless solid, and epimer epi-13 with the equatorial hydroxy group in 38% yield (0.136 g, 0.23 mmol) as colorless oil, respectively.

m.p. 13: 110.5° C.

$^1$H-NMR (200 MHz, CDCl$_3$): δ 7.41-7.21 (m, 20H, Ph), 6.02-5.72 (m, 2H, allyl), 5.56 (dd, 1H, $^2J$=1.5 Hz $^3J$=17.0 Hz, allyl), 5.39 (dd, 1H, $^2J$=1.4 Hz $^3J$=10.1 Hz, allyl), 5.28-5.10 (m, 2H, allyl), 4.974.84 (m, 6H, OCH$_2$Ph), 4.844.60 (AB, 2H, OCH$_2$Ph), 4.34-4.07 (m, 2H, allyl), 3.98 (dd, 1H, $^3J$=3.3 Hz, 9.5 Hz, H-5), 3.95 (dd, 1H, $^3J$=9.3 Hz, H-3), 3.54(dd, 1H, $^3J$=9.5 Hz, H-4), 3.39 (d, 1H, $^3J$=9.3 Hz, H-6), 3.27 (d, 1H, $^3J$=9.3 Hz, H-2), 2.58 (s, 1H, OH)

¹³C-NMR (50.3 MHz, CDCl₃): δ 75.4 (1C), 76.4 (2C), 76.4 (1C), 76.5 (2C), 82.1 (1C), 82.5 (1C), 82.9 (1C), 83.0 (1C), 83.3 (1C), 117.1 (1C), 117.7 (1C), 128.1, 128.1, 128.3, 128.3, 128.5, 128.7, 128.8, 135.4 (1C), 140.4 (1C)

MS (pos. mode, FAB, NBA) m/z (%): 624 [M+NH₄⁺] (100), 607 [M+H⁺] (<1), 534 [M+NH₄⁺+H⁺−Bn⁺] (5), 515 [M−Bn⁺] (11), 425 M−2 Bn⁺+H⁺] (2), 335 [M−3 Bn⁺+2H⁺] (1)

MS (neg. mode, FAB, NBA) m/z (%): 605 [M−H⁺]] (63), 565 [M−C₃H₅⁺] (13), 515 [M−Bn⁺] (100), 425 [M−2 Bn⁺+H⁺] (10)

C₃₉H₄₂O₆ (606.76): calcd. C 77.20, H 6.98; found C 77.21, H 7.04

Synthesis of (4aα, 5α,6β,7α,8β, 8aα)-5,6,7,8-tetra(benzyloxy)-4a-hydroxy-4a,5,6,7,8,8a-hexahydro-[2H]-chromen (14)

270 mg 13 (0.446 mmol) were dissolved in 50 mL dry methylene chloride. Bis(triccylohexylphosphin)benzylidene ruthenium (IV) dichloride (Grubb's catalyst, 5.8 mg, 7 μmol) was added under argon and the solution was stirred for 24 hours in the dark. Then another 7.9 mg (10 mmol) Grubb's catalyst was added and the mixture was heated to reflux for 90' min. After reaching room temperature methylene chloride was added and the organic layer was extracted with phosphate buffer (0.5 M, pH 7) and brine. Then it was dried, over anhydrous sodium sulfate, filtered, and the solvent was removed under reduced pressure. The dry residue was chromatographed by preparative HPLC (RP18, 90% MeOH, 40 mL/min, $t_{Ret}$=20.5 min) to give 14 in 93% yield (237.8 mg, 0.41 mmol) as a colorless solid.

m.p.: 128.5° C.

¹H-NMR (200 MHz, CDCl₃): δ 7.50-7.27 (m, 20H, Ph), 6.11 (dt, 1H, ³J=10.1 Hz, ⁴J=2.0 Hz, H-4), 5.94 (ddd, 1H, ³J=10.1 Hz, ⁴J=3.1 Hz, ⁴J=1.6, H-3), 5.134.66 (m, 8H, OCH₂Ph), 4.49-4.21 (m, 2H, H-2), 4.21 (dd, 1H, ³J=9.3 Hz, H-8), 4.07 (dd, 1H, ³J=9.3 Hz, H-6), 3.64 (dd, 1H, ³J=9.1 Hz, H-7), 3.38 (d, 1H, ³J=7.8 Hz, H-5), 3.33 (d, 1H, ³J=7.4 Hz, H-8a), 2.23 (s, 1H, OH)

¹³C-NMR (50.3 MHz, d₆-DMSO): δ 140.00 (C), 139.76 (C), 139.65 (C), 139.41 (C), 129.81, 127.40, 83.89 (CH), 83.83 (CH), 82.23 (CH), 81.19 (CH), 80.18 (CH), 75.97 (CH₂), 75.67 (CH₂), 75.55 (CH₂), 74.75 (CH₂), 68.30 (C), 66.62 (CH₂)

MS (neg. mode, FAB, NBA) m/z (%): 731 [M+NBA] (<1), 577 [M−H⁺] (<1)

MS (pos. Mode, FAB, NBA) m/z (%): 579 [M+H⁺] (3), 91 [Bn⁺] (100)

C₃₇H₃₈O₆ (578.71): calcd C 76.79, H 6.62; found C 76.61, H 6.54

Synthesis of (4aα, 5α,6β,7α,8β,8aα)-5,6,7,8-tetra(benzyloxy)-4a-hydroxy-octahydro-chromen (15)

14 (0.238 g, 0.412 mmol) was dissolved in 10 mL toluene/acetone (1:1, v/v) and 78 mg (84 μmol) chlorotris(triphenylphosphine)rhodium(I) (Wilkinson's catalyst) were added. The mixture was subjected to a hydrogen atmosphere in a self-built hydrogenation apparatus and stirred in the dark for seven days, during which time the solution turned from yellow to deep red. The reaction was stopped by flooding the apparatus' with argon. The solvents were removed under reduced pressure and the residue was dissolved in 100 mL t-butylmethyl ether and washed twice with brine. The organic phase was dried over anhydrous sodium sulfate and filtered. After evaporation the residue was purified by preparative HPLC (RP18, 40 mL/min, 88% MeOH, $t_{Ret}$=33.00 min) to give 15 as a slightly yellow oil (0.124 g, 52% yield).

¹H-NMR (200 MHz, CDCl₃): δ 7.44-7.21 (m, 20H, Ph), 5.05-4.59 (m, 8H, OCH₂Ph), 4.22-4.08 (m, 1H, H-2), 4.05 (dd, 1H, ³J=9.4 Hz, H-6), 3.91 (dd, 1H, ³J=9.34 Hz, H-0.8), 3.56 (dd, 1H, ³J=9.34 Hz, H-7), 3.53-3.39 (m, 1H, H-2) 3.24 (d, 1H, ³J=9.7 Hz, H-5), 3.22 (d, 1H, ³J=9.7 Hz, H-8a), 2.16-1.95 (m, 2H, tetrahydropyrane(thp)-ring), 1.57-1.26 (m, 2H, thp-ring)

MS (neg. mode, DCI, NH₃) m/z (%): 579 [M−H⁺] (70), 489 [M−Bn⁺] (43),

MS (EI): 489 [M−Bn⁺] (42), 91 (Bn⁺) (100)

HR-MS: calcd. for C₃₀H₃₃O₆ [M−Bn⁺] 489.2284, found 489.2260

Synthesis of (4aα, 5α,6β,7α,8β,8aα)-5,6,7,8-tetra(benzyloxy)-4a-butyryloxy-octahydro-chromen (16)

15 (0.120 g, 0.207 mmol) was dissolved in 7.5 mL dry toluene. After adding 0.1 mL (5.733 mmol) butyric acid chloride and 0.35 mL (1.376 mmol) phosphazen base-P₁-t-Bu the mixture was heated to reflux for 12 hours. The mixture was dried in high vacuum, the residue was dissolved in t-butylmethyl ether and the organic phase was extracted with phosphate buffer (0.5 mM, pH 7) and brine. The solution was dried over anhydrous sodium sulfate, filtered, and the solvent was evaporated under reduced pressure. The residue was purified by preparative HPLC (RP18, 40 mL/min, 90% MeOH, $t_{Ret}$=44.13 min). 16 was a colorless oil (0.078 g, 58% yield).

¹H-NMR (200 MHz, CDCl₃): δ 7.45-7.18 (m, 20H, Ph), 5.00-4.70 (m, 8H, OCH₂Ph), 4.12 (dd, 1H, ²J=11.3 Hz, ³J=5.0 Hz, H-2 eq), 3.91 (dd, 1H, ³J=9.3 Hz, H-8), 3.89-3.75 (m, 1H, H-eq), 3.82 (dd, 1H, ³J=9.5 Hz, H-6), 3.62-3.43 (m, 1H, H-2ax), 3.55 (dd, 1H, ³J=9.2 Hz, H-7), 3.31 (d, 1H, ³J=9.4 Hz, H-5), 3.15 (d, 1H, ³J=9.6 Hz, H-8a), 2.53-2.27 (m, 2H, α-CH₂(Bt)), 1.95-1.79 (m, 1H, thp-ring), 1.88-1.66 (m, 2H, β-CH₂ (Bt)), 1.66-1.53 (m, 1H, thp-ring), 1.38-1.19 (m, 1H, thp-ring), 1.01(t, 3H, ³J=7.4 Hz, CH₃)

¹³C-NMR (50.3 Mhz, CDCl₃): δ=172.7 (C), 139.3 (C), 138.9 (C), 138.8 (C), 138,7 (C), 128.9, 128.8, 128.8, 128.7, 128.6, 128.5, 128.5, 128.2, 128.1, 128.0, 128.0, 84.2 (CH), 83.5 (CH), 83.0 (CH), 83.0 (CH), 82.66 (C), 81.1 (CH), 76.7(CH₂), 76.6 (CH₂), 76.5 (CH₂), 76.1 (CH₂), 68.6 (CH₂), 38.4 (CH₂), 30.2 (CH₂), 22.4 (CH₂), 19.1 (CH₂), 14.2 (CH₃)

MS (neg. mode, DCI, NH₃): m/z (%): 649 (5) [M−H⁺], 579 (61) [M−H⁺−Bt], 559 (100) [M−C₇H₇⁺], 489 (18) [M−C₇H₇⁺−Bt], 469 (20) [M−C₇H₇⁺−C₇H₇]

HR-MS: calcd. for C₃₄H₃₉O₇ [M−Bn⁺] 1559.2696; found 559.2720

Synthesis of (4aα,5α,6β,7α,8β,8aα)-5,6,7,8-tetrakis[[bis(benzyloxy)phosphoryl]oxy]-4a-butyryloxy-octahydro-chromen (17)

75.4 mg (0.116 mmol) 16 and palladium on charcoal (10% Pd, 149 mg, 0.140 mmol) were suspended in 10 mL ethanol under argon and at −20° C. The atmosphere was exchanged to hydrogen in a self-built hydrogenation apparatus and stirred for 10 days. The mixture was ultrafiltered and the filtrate was dried under reduced pressure.

The residue and tetrazole (85.1 mg, 1.22 mmol) were dissolved in 3 mL dry acetonitrile under argon. Dibenzyl-N,N-diisopropylphosphoramidite (390 μl, 1.16 mmole) was added and the mixture was stirred for 18 hours at room temperature.

The flask was cooled to −40° C. and 0.285 mL (1.356 mmole) peracetic acid (32% by weight) was added. The solution was allowed to warm to room temperature and the volatile components were removed in high vacuum. Crude 17 was purified by preparative HPLC (RP18, 88% MeOH, 40 mL/min, $t_{ret}$=50.25 min) to give a clear oil, that contained substantial amounts of a by-product 17a that where the 4a-O-butyrate migrated to the 5-hydroxy group. Both compounds were separated by a second preparative HPLC run (ChiraDex, 40 mL/min, 100% MeCN). 4a-phosphorylated by-product 17a eluted with $t_{ret}$=31.0 min. (15 mg, 11.3 µmol, 10% yield), while the desired compound 17 had a $t_{Ret}$=120 min (16.8 mg, 12.6 µmol, 11% yield).

$^1$H-NMR (200 MHz, CDCl$_3$): δ 7.46-7.06 (m, 20H, Ph), 5.17-4.58 (m, 19H, CH$_2$-Bn, H-6, H-7, H-8), 4.43 (dd, 1H, $^3J_{HH}$=$^3J_{PH}$=9.1 Hz, H-5), 4.00-3.27 (m, 1H, thp-ring), 3.81-3.68 (m, 1H, thp-ring), 3.42-3.21 (m, 1H, thp-ring), 3.30 (d, 1H, $^3J$=9.7 Hz, H-8a), 2.47-2.20 (m, 2H, α-CH$_2$(Bt)), 1.81-1.49 (m, 5H, thp, β-CH$_2$ (Bt)), 0.93 (t, 3H, $^3J$=7.4, CH$_3$)

$^{13}$C-NMR (50.3 MHz, CDCl$_3$): δ 172.04 (C), 136.88-136.15 (C-Ph), 129.02-127.89 (CH-Ph), 80.47 (C), 79.62 (CH), 78.66 (CH), 77.21 (CH), 76.84 (CH), 75.35 (CH), 70.45-69.41 (CH$_2$-Bn), (CH$_2$), 68.49 (CH$_2$), 37.72 (CH$_2$), 30.16 (CH$_2$), 21.66 (CH$_2$), 18.97 (CH$_2$), 14.10 (CH$_3$)

$^{31}$P-NMR (81 MHz, CDCl$_3$): δ 0.40 (1P), 0.30 (1P), 0.15 (1P), −0.97 (1P)

MS (neg. mode, FAB, NBA) m/z (%): 1329 [M−H$^+$] (<1), 1239 [M−Bn$^+$] (5)

HR-MS: calcd. for C$_{62}$H$_{67}$O$_{19}$P$_4$ [M−Bn$^+$] 1239.3228, found 1239.3210

(4aα, 5α,6β,7α,8β, 8aα)-4a,6,7,8-Tetrakis[[bis(benzyloxy) phosphoryl]oxy]-5-butyryloxy-octahydro-chromen (17a)

$^1$H-NMR (200 MHz, CDCl$_3$): δ 7.53-7.07 (m, 40H, Ph), 5.39-4.68 (m, 20, CH$_2$Ph, H-5, H-6, H-7, H-8), 3.83 (dd, 1H, $^2J$=10.9 Hz, $^3J$ 4.2 Hz, H-2 eq), 3.45 (dd, 1H, $^3J$=9.7 Hz, $^4J_{PH}$=5.9 Hz, H-8a), 3.35 (m, 1H, thp-ring), 2.96 (m, 1H, thp-ring), 2.17-1.89 (m, 1H, thp-ring), 1.76-1.47 (m, 4H, thp-ring, β-CH$_2$ (Bt)), 0.86 (t, 3H, $^3J$=7.4 Hz, CH$_3$)

$^{31}$C-NMR (50.3 MHz, CDCl$_3$>: δ 173.75 (C), 136.88-136.15 (C), 129.20-127.51 (CH), 81.84 (C), 79.07 (CH), 77.95 (CH), 76.97 (CH), 76.97 (CH), 72.97 (CH), 70.03-69.33 (CH$_2$-Bn), 68.49 (CH$_2$), 35.97 (CH$_2$), 29.63 (CH$_2$), 20.96 (CH$_2$), 18.12 (CH$_2$), 14.04 (CH$_3$)

31P-NMR (81 MHz, CDCl$_3$): 8-0.02 (1P), −0.45 (1P), −0.86 (1P), −5.28 (1P)

MS (pos. mode, DCI, NH$_3$) m/z (%): 1331 [M+H$^+$] (2), 1241 [M+2*H$^+$−Bn$^+$] (3)

MS (neg. mode, DCI, NH$_3$) m/z (%): 1329 [M−H$^+$] (<1), 1239 [M−Bn$^+$] (9), 1149. [M+H$^+$−2*Bn$^+$] (4)

HR-MS calcd. for C$_{62}$H$_{67}$O$_{19}$P$_4$ [M−Bn$^+$] 1239.3228, found 1239.323

Synthesis of (4aα, 5α,6β,7α,8β,8aα)-4a-butyryloxy-5,6,7,8-tetrakis(phosphonooxy)-octahydro-chromen (18)

17 (6.7 mg, 12.6 µmol) was dissolved in 5.5 mL glacial acetic acid and 185 mg palladium on charcoal (10% Pd, 174 µmol) was added. The mixture was stirred under a hydrogen atmosphere for 12 hours. Then the catalyst was removed by ultrafiltration (0.45 µm RC55 membrane filter) and the filtrate was freeze-dried to yield 7.5 mg (99% yield) of 18 as a colorless oil.

$^1$H-NMR (200 MHz, d$_6$-DMSO): δ 4.44 (ddd, 1H, J=9.6 Hz, H-8), 4.31 4.02 (m, 3H, H-6, H-7, H-2), 3.88 (d, 1H, J=9.5 Hz, H-5), 3.52-3.21 (m, 3H, H-8a, H-2, thp-ring), 2.23 (t, 2H, J=7.2 Hz, α-CH$_2$ (Bt)), 1.62-1.29 (m, 7H, β-CH$_2$ t), thp-ring), 0.89 (t, 3H, J=7.2 Hz)

$^{13}$C-NMR (50.3 MHz, d$_6$-DMSO): δ 171.43 (C), 82.08, 67.92 (CH$_2$), δ8.16 (CH$_2$), 29.08 (CH$_2$), 21.96 (CH$_2$), 18.95 (CH$_2$), 14.41 (CH$_3$)

$^{31}$P-NMR (81 MHz, d$_6$-DMSO): δ 0.89 (2P), 0.16 (1P), −0.18 (P)

MS (neg. mode, FAB, glycerol) m/z (%): 631 [M−2H$^+$+Na$^+$] (5), 609 [M−H$^+$] (26)

Synthesis of (4aα, 5α,6β,7α,8β, 8aα)-5,6,7,8-tetrakis[[bis (acetoxymethoxy)-phosphoryl]oxy]-4a-butyryloxy-octahydro-chromen (19)

18 (7.2 mg, 11.8 µmol) was dissolved in 0.7 mL dry acetonitrile and diisopropylethyl amine (62 µl, 365 µmol) and acetoxymethyl bromide (36 µL, 365 µmol) were added under an argon atmosphere. After stirring 36 hours at room temperature all volatile components were removed in high vacuum and the residue was extracted several times with 1 mL dry toluene. The combined extracts were centrifuged and subsequently the solvent was removed under reduced pressure to give 19 (8 mg, 6 µmol, 50% yield) as a colorless oil.

$^1$H-NMR(200 MHz, d$_8$-toluene): δ 6.01-5.62 (m, 16H, OCH$_2$O), 5.07-4.52 (m, 4H, H-5, H-6, H-7, H-8), 3.92-3.78 (m, 1H, thp-ring), 3.78-3.65 (m, 1H, H-2eq), 3.27-3.12 (m, 1H, H-2ax), 2.91 (d, 1H, $^3J$=9.2 Hz, H-8a), 2.31-2.13 (m, 2H, α-CH$_2$(Bt)), 1.89 (s, 3H, OCH$_3$), 1.88 (s, 3H, OCH$_3$), 1.85 (s, 3H, OCH$_3$), 1.84 (s, 3H, OCH$_3$), 1.81 (s, 3H, OCH$_3$), 1.76 (s, 3H, OCH$_3$), 1.75 (s, 3H, OCH$_3$), 1.74 (s, 3H, OCH$_3$), 1.69-1.30 (m, 5H, P—CH$_2$, thp-ring), 0.88 (t, 3H, $^3J$=7.4 Hz, CH$_3$(Bt))

$^{13}$C-NMR (50.3 MHz, d$_8$-toluene): δ 83.65-82.94 (OCH$_2$O), 78.70 (CH), 78.28 (CH), 77.59 (CH), 77.25 (CH), 76.08 (CH), 67.74 (CH$_2$), 37.16 (CH$_2$), 28.94 (CH$_2$), 21.72 (CH$_2$). 21.62-19.83 (CH$_3$), 18.83 (CH$_2$), 13.72 (CH$_3$)

$^{31}$P-NMR (81 MHz, d$_8$-toluene): δ −2.98 (1P), −3.14 (1P), −3.29 (1P), −3.36 (1P)

MS (neg. mode, FAB, NBA) m/z (%): 1113 [M−CH$_2$OAc$^+$] (9), 1041' [M−2 CH$_2$OAc$^+$+H$^+$] (5), 969 [M−3 CH$_2$OAc$^+$+2H$^+$] (2), 241 [(AcOCH$_2$O)$_2$PO$_2^-$] (94)

EXAMPLE 7

Synthesis of(1S 2R, 3S, 4R, 5S, 6S, 8R)-2,3,4,5-tetrakis[[bis(acetoxymethoxy) -phosphoryl]oxy]-7, 12-dioxa-tricyclo-[6.3.1.0$^{1,6}$]-dodecane (8)

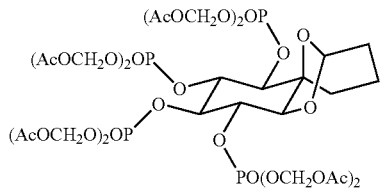

Referring to the reaction scheme shown in FIG. 1, the compound (1S, 2R, 3S, 4R, 5S, 6S, 8R)-2,3,4,5-tetrakis[[bis (acetoxymethoxy)phosphoryl]oxy]-7,12-dioxa-tricyclo-[6.3.1.0$^{1,6}$]-dodecane (8) was synthesized as follows:

Synthesis of 1-O-allyl-3,4,5,6-tetra-O-benzyl-myo-inosose (2)

1.44 g (2.5 mmol) 1-O-Allyl-3,4,5,6-tetra-O-benzyl-myo-inositol 1 was dissolved in 10 mL DMSO and 1 mL acetic acid anhydride (10.6 mmol) was added under an argon atmosphere. After 48 hours at room temperature all volatile ingredients were removed in high vacuum and the crude yellow residue was recrystallized twice from methanol to give 1.13 g (2.0 mmol, 79% yield) of 2.

m.p.: 124.3° C.

$^1$H-NMR (200 MHz, CDCl$_3$): δ 7.53-7.23 (m, 20H, Ph), 6.14-5.90 (m,H, OCH$_2$CHCH$_2$), 5.47-5.20 (m, 2H, OCH$_2$CHCH$_2$), 5.06-4.57 (m, 8H, OCH$_2$Ph), 4.49-4.34 (m, 1H, OCHHCHCH$_2$), 4.24 (dd, 1H, $^3J$=9.9 Hz, 1.6 Hz, H-1), 4.21-4.07 (m, 1H, OCHHCHCH$_2$), 4.16 (dd, 1H, $^3J$=9.9 Hz, 1.6 Hz, H-3)33.95 (dd, 1H, H-5, $^3J$=9.1 Hz, H-5), 3.69 (dd, 1H, H-4, $^3J$=9.7 Hz, H-4), 3.66 (dd, 1H, $^3J$=9.6 Hz, H-6)

$^{13}$C-NMR (50.3 MHz, d$_6$DMSO): δ 203.44 (C), 139.37 (C), 139.37 (C), 39.31 (C), 139.14 (C), 135.83 (CH), 129.18-128.21 (CH, Bn) 117,25 (CH$_2$), 84.46 (CH), 84.30 (CH), 82.15 (CH), 81.57 (CH), 81.51 (CH), 75.79 (CH$_2$), 75.50 (CH$_2$), 75.50 (CH$_2$), 73.03 (CH$_2$), 72.16 (CH$_2$)

MS (pos. mode, NH$_3$, DCI) m/z (%): 579 [M+H$^+$] (10), 489 [M+2*H$^+$–Bn$^+$] (68), 399 [M+3*H$^+$–2*Bn$^+$] (6), 108 [Bn$^+$+NH$_3$] (100)

C$_{37}$H$_{38}$O$_6$ (578.69): calcd. C 76.79, H 6.61; found C 76.54, H 6.53

Synthesis of rac-(1S, 2R, 3S, 4R, 5S, 6S)-1-allyl-6-allyloxy-2,3,4,5-tetra-benzyloxy- 1-hydroxy-cyclohexane (3)

2 (561 mg, 0.97 mmol) was suspended in 10 mL absolute diethyl and the mixture was cooled to −25° C. 0.55 mL (1.10 mmol) of a 2-molar solution of allyl magnesium chloride in THF was added under argon and vigorous stirring. After 20 min another 0.1 mL (0.2 mmol) allyl magnesium chloride solution was added. The mixture was allowed to warm up and was quenched with 10 mL 0.5 M phosphate buffer, pH 7, after 14 hours. The organic layer was diluted with t-butylmethyl ether, extracted with brine and dried over anhydrous sodium sulfate. After filtration and evaporation of the solvent in vacuum the solid residue was chromatographed by preparative HPLC (RP-18, 40 mL/min, 90% MeOH, $t_{Ret}$=34.50 min) to give 377 mg 3 as a colorless solid (0.61 mmol, 63% yield).

m.p.: 97.5° C.

$^1$H-NMR (200 MHz, CDCl$_3$): δ 7.53-7.32 (m, 20H, Ph), 6.19-5.95 (m, 1H, OCH$_2$CHCH$_2$), 5.92-5.68 (m, 1H, HOCCH$_2$CH=CH$_2$), 5.42-4.72 (m, 8H, CH$_2$Ph), 4.48 (dd, 1H, $^2J$=12.0 Hz, $^3J$=5.7 Hz, OCHHCH=CH$_2$), 4.15 (dd, 1H, $^2J$=12.1 Hz, $^3J$=5.7 Hz OCHHCH=CH$_2$), 4.03 (dd, 1H, $^3J$=9.4 Hz, H-3), 3.98 (dd, 1H, $^3J$=9.4 Hz, H-5), 3.48 (dd, 1H, $^3J$=9.8 Hz, H$_4$), 3.38 (d, 1H, $^3J$=9.5 Hz, H-6), 3.25 (d, 1H, $^3J$=9.4 Hz, H-2), 2.61 (d, 1H, HOCCH$_2$CHCH$_2$, $^3J$=7.2 Hz), 2.31 (br s, 1H, OH)

$^{13}$C-NMR (50.3 MHz, CDCl$_3$): δ 139.08 (C), 139.08 (C), 138.96 (C), 138.65 (C), 135.34 (CH), 133.33 (CH), 129.18-127.51 (CH, Bn), 119.92 (CH$_2$), 117.39 (CH$_2$), 83.69 (CH), 83.55 (CH), 83.55 (CH), 80.43 (CH), 80.17 (CH), 78.02 (C), 76.31 (CH$_2$), 76.31 (CH$_2$), 76.31 (CH$_2$), 75.87 (CH$_2$), 75.17 (CH$_2$), 39.94 (CH$_2$)

MS (pos. mode, FAB, NBA) m/z (%): 621 [M+H$^+$] (3), 91 [Bn$^+$] (100)

MS (neg. mode, FAB, NBA) m/z (%): 772 [M+NBA-H$^+$] (1), 619 [M−H$^+$] (1), 503 [M−BnO$^+$] (14)

C$_{40}$H$_{44}$O$_6$ (620.79): calcd. C 77.39, H 7.14; found C 77.21, H 7.04

Synthesis of (5aα,6α,7β,8α,9β,9aα)-6,7,8,9-tetrabenzyloxy-5a-hydroxy-2,5,5a,6,7,8,9,9a-octahydro-benzo[b]oxepin (4)

3 (353 mg, 0.57 mmol) was dissolved in 50 mL dry methylene chloride. 5.2 mg (6.3 μmol) bis(tricyclohexylphosphin) benzylidene-ruthenium (IV)-dichloride was added under an argon atmosphere, and the solution was stirred for 72 hours in the dark. The organic layer was diluted with methylene chloride and washed several times with phosphate buffer pH 7 and brine. After drying over sodium sulfate and filtration, the organic layer was dried and the crude residue was purified by preparative HPLC (RP-18, 40 mL/min, 90% MeOH, $t_{Ret}$=25.25 min) to give 318 mg (0.54 mmol, 94% yield) 4 as a colorless solid.

m.p.: 123.0° C.

$^1$H-NMR (200 MHz, CDCl$_3$): δ 7.48-7.23 (20H, Ph), 6.09-5.95 (m, 1H, H-3), 5.80-5.65 (m, 1H, H-4), 5.17-4.67 (m, 8H, OCH$_2$Ph), 4.50 (dd, 1H$^{12}J$=15.4 Hz, $^3J$=5.6 Hz, H-2), (4.25-4.07, m, 1H, H-2), 4.12 (dd, 1H, $^3J$=9.6 Hz, H-7), 3.87 (dd, 1H, $^3J$=9.2 Hz, H-9), 3.60 (dd, 1H, $^3J$=9.5 Hz, H-8), 3.51 (d, 1H, $^3J$=9.2 Hz, H-9a), 3.27 (d, 1H, $^3J$=9.7 Hz, H-6), 2.97 (dd, 1H, $^2J$=15.8 Hz, $^3J$=7.8 Hz, H-5), 2.64 (s, 1H, OH), 2.22-2.07 (m, 1H, H-5)

$^3$C-NMR (50.3 MHz, CDCl$_3$): δ 139.46 (C), 139.16 (C), 139.02 (C), 138.35 (C), 132.33 (CH), 129.00-127.95 (CH, Bn),128.33 (CH), 88.53 (CH), 83.36 (CH), 82.79 (CH), 82.74 (CH), 82.36 (CH), 76.64 (CH$_2$), 76.64 (CH$_2$), 76.34 (CH$_2$), 76.30 (CH$_2$), 74.29 (C), 69.72 (CH$_2$), 37.42 (CH$_2$)

MS pos. mode, FAB, NBA) m/z (%): 591 [M−H$^+$] (1), 91 [Bn$^+$] (100)

MS (neg. mode, FAB, NBA) m/z (%): 745 [M+NBA$^-$] (2), 591 [M−H$^+$] (<1)

C$_{38}$H$_{40}$O$_6$ (592.73): calcd. C 77.00, H 6.80; found C77.03, H 6.73

Synthesis of (1S,2R,3S,4R,5S,6S,8R)-2,3,4,5-tetrabenzyloxy-7,12-dioxa-tricyclo-[6.3.1.0$^{1,8}$]-dodecane (5)

4 (0.138 g, 0.233 mmol) was dissolved in 10 mL aqueous ethanol (90%). Tris(triphenylphosphin)rhodium-(I)-chloride (46 mg, 0.43 mmol) and 0.04 mL diisopropylethyl amine (0.234 mmole) were added under argon. The mixture was heated to reflux in the dark for 18 hours. Under reduced pressure the mixture was dried, the residue dissolved in t-butylmethyl ether and washed with phosphate buffer pH 7 and brine. The organic layer was dried over sodium sulfate and filtered. The filtrate was dried and the crude residue was prepurified by preparative HPLC (RP18, 90% MeOH, 40 mL/min). The resulting mixture was dissolved in 5 mL chloroform, 0.1 mL trifluoro acetic acid was added, and the mixture was stirred for 3 days at room temperature. The solution was diluted with methylene chloride and extracted with phosphate buffer pH 7 and brine. The organic layer was dried over sodium sulfate and filtered. The filtrate was dried and the crude residue was purified by preparative HPLC (RP18, 90% MeOH, 40 mL/min, $t_{Ret}$=32.10 min). 5 was isolated as a colorless solid (0.050g, 0.084 mmol, 36% yield). As a by-product 0.014 g (0.026 mmol, 10% yield) 6,7,8,9-tetrabenzyloxy-5a-hydroxydecahydrobenzo-oxepin was isolated.

m.p.: 106.3° C.

$^1$H-NMR (200 MHz, CDCl$_3$): δ 7.60-7.25 (20H, Ph), 5.73 (br s, 1H, OCHO), 5.16-4.75 (m, 8H, OCH$_2$Ph), 4.18 (d, 1H, $^3J$=6.1 Hz, H-6), 4.00 (dd, 1H, $^3J$=9.5 Hz, H-3), 3.71 (dd, 1H, $^3J$=9.8 Hz, 6.2 Hz, H-5), 3.53 (dd, 1H, $^3J$=9.5 Hz, H-4), 3.52 (d, 1H, $^3J$=9.7 Hz, H-2), 2.36-1.64 (m, 5H, thp-ring), 1.40-1.22 (m, 1H, thp-ring)

$^{13}$C-NMR (50.3 MHz, CDCl$_3$): δ 139.14 (C), 139.14 (C), 139.01 (C), 138.41 (C), 103.87 (CH), 86.08 (CH), 83.20 (CH), 83.10 (C), 82.53 (CH), 81.72 (CH), 81.67 (CH), 76.90 (CH$_2$), 76.18 (CH$_2$), 76.00 (CH$_2$), 74.62 (CH$_2$), 31.27 (CH$_2$), 30.60 (CH$_2$), 16.59 (CH$_2$)

MS (neg. mode, DCI, NH$_3$) m/z (%): 591 [M−H$^+$], 501 [M−Bn$^+$], 411, [M−2Bn$^+$+H$^+$], 321 [M−3Bn$^+$+2H$^+$]

MS (pos. mode, DCI, NH$_3$) m/z (%): 610 [M+NH$_4^+$], 593 [M+H$^+$], 520 [M+NH$_4^+$−Bn]

C$_{38}$H$_{40}$O$_6$ (592.73): calcd. C77.00, H 6.80; found C 77.19, H 6.69

Synthesis of (1S, 2R, 3S, 4R, 5S, 6S, 8R)-2,3,4,5-tetrakis[[bis(benzyloxy)-phosphoryl]oxy]-7,12-dioxa-tricyclo-[6.3.1.01,6]-dodecane (6)

5 (0.159 g, 0.267 mmol) was dissolved in 5.5 mL ethanol at −20° C. A suspension of 0.222 g palladium on charcoal (10% Pd, 0.209 mmol) in 5.5. mL ethanol under an argon atmosphere at −20° C. was added. The argon atmosphere was exchanged to hydrogen in a self-built hydrogenation apparatus and the mixture was stirred for eight days at room temperature. Finally, the hydrogen was exchanged to argon and the catalyst was removed by ultrafiltration The filtrate was dried in high vacuum and the residue was dissolved in dry acetonitrile. Then tetrazole (160 mg, 2.286 mmol) and dibenzyl diisopropylphosphoramidite (0.705 ml, 2.098 mmol) were added under argon and the mixture was stirred for 18 hours. After cooling to −0° C., peracetic acid (32% in acetic acid, 0.44 mL, 2.1 mmol) was added. The solution was allowed to warm to room temperature and all volatile components were removed in high vacuum. The oily residue was chromatographed by preparative HPLC (88% MeOH,. 40 mL/min, $t_{Ret}$=38.45 min) to give 6 (0.173 mg, 0.136 mmol, 51% yield from 5) as a colorless oil.

$^1$H-NMR (200 MHz, CDCl$_3$): δ 7.45-7.17 (m, 8H, Ph), 5.50 (br s, 1H, OCHO), 5.19-4.77 (m, 20H, CH$_2$Ph, H-2, H-3, H-4, H-5), 4.18 (d, 1H, $^3$J=4.7 Hz, H-6), 2.12-1.90 (m, 1H, thp-ring), 1.82-1.45 (m, 5H, thp-ring)

$^{31}$P-NMR (81 MHz, CDCl$_3$): 8-0.16 (1P), −0.35 (1P), −0.95 (2P)

$^{13}$C-NMR (50.3 MHz, CDCl$_3$): δ 136.18 (C), 136.17 (C), 136.17 (C), 136.16 (C), 104.23 (CH), 81.22 (C), 78.77 (CH), 78.20 (CH), 77.76 (CH), 77.31 (CH), 31.33 (CH$_2$), 30.22 (CH$_2$), 16.17 (CH$_2$)

MS (neg. mode, DCI, NH$_3$) m/z (%): 1271 [M−H+], 1181 [M−Bn$^+$], 1091, [M−2Bn$^+$+H$^+$]

MS (pos. mode, DCI, NH$_3$) m/z 12906[M+NH$_4^+$], 1272 [M+H$^+$]

HR-MS: calcd. for C$_{59}$H$_{61}$O$_{18}$P$_4$ [M−Bn$^+$] 1181.2809, found 1181.2819

Synthesis of(1S, 2R, 3S, 4R, 5S, 6S, 8R)-2,3,4,5-tetrakis(phosphonooxy)-7,12-dioxa-tricyclo-[6.3.1.0$^{1,6}$]-dodecane (7)

Under an argon atmosphere 6 (168 mg, 0.132 mmol) was dissolved in 3 mL ethanol cooled to −20° C. A suspension of 190 mg palladium on charcoal (10% Pd, 0.179 mmol) in 5 mL ethanol under an argon atmosphere at −20° C. was added. The argon atmosphere was exchanged to hydrogen in a self-built hydrogenation apparatus and the mixture was stirred for seven days at room temperature. Finally, the hydrogen was exchanged to argon and the catalyst was removed by ultrafiltration. The filtrate was dried in high vacuum to give 7 as the free acid (60 mg, 0.108 mmol). 33 mg were treated with Dowex 50 WX8, sodium form to give 7 as the sodium salt (17 mg, 0.023 mmole, 17% yield).

$^1$H-NMR (200 MHz, D$_2$O): δ 5.63 (br s, 1H, OCH$_2$O), 4.32-3.91 (m, 5H, H-2, H-3, H-4, H-5, H-6), 2.12-1.90 (m, 1H, thp-ring), 1.85-1.32 (m; 5H, thp-ring)

$^{31}$P-NMR (81 Hz, D$_2$O): δ 2.13 (1P), 1.85 (1P), 0.95 (2P)

$^{13}$C-NMR (50.3 MHz, D$_2$O): δ 103.8 (1C, OCH$_2$O), 80.7 (1C), 80.0 (1C), 77.7 (1 C), 76.5 (2 C), 30.3 (1C), 29.6 (1C), 15.5 (1C)

MS (neg. mode, FAB, glycerol): 573 [M−2H$^+$+Na$^+$] (13), 551 [M−H$^+$] (30)

Synthesis of (1S, 2R, 3S, 4R, 5S, 6S, 8R)-2,3,4,5-tetrakis[[bis(acetoxymethoxy)-phosphoryl]oxy]-7,12-dioxa-tricyclo-[6.3.1.0$^6$1-dodecane (8)

7 (0.127 g, 0.23 mmol) was thoroughly dried and dissolved in 2.5 mL dry acetonitrile. Diisopropylethyl amine (0.28 mL, 1.65 mmol) and acetoxymethyl bromide (0.164 mL, 1.64 mmol) were added and the solution was stirred for 48 hours at room temperature in the dark. All volatile components were removed in high vacuum and the oily residue was purified by preparative HPLC (RP18, 40 mL/min, 60% MeOH, $t_{Ret}$=20.25 min). 8 was isolated in 33% yield (0.045 g, 0.043 mmol) as a clear oil.

$^1$H-NMR (200 MHz, d$_8$-toluene): δ 5.91-5.55 (m, 16H, OCH$_2$OAc), 5.42 (br s, 1H, OCH$_2$O), 5.17-5.00 (m, 2H) and 4.96-4.76 (m, 4H H-2, H-3, H-4, H-5), 4.25 (d, 1H, $^3$J=4.3 Hz, H-6), 2.31-2.13 (m, 2H, thp-ring), 1.88 (s, 3H, CH$_3$), 1.88 (s, 3H, CH$_3$), 1.87 (s, 3H, CH$_3$), 1.86 (s, 9H, 3*CH$_3$), 1.84 (s, 3H, CH$_3$), 1.76 (s, 3H, CH$_3$), 1.59-1.22 (m, 4H, thp-ring)

$^{13}$C-NMR (50.3 MHz, d$_8$-toluene): δ 69.34-168.82 (C), 169.22 (C), 169.13 (C), 168.85 (C), 104.24 (CH$_2$), 83.69-82.96 (CH$_2$), 81.66 (C), 79.34 (CH), 78.50 (CH), 78.21 (CH), 77.20 (CH), 77.03 (CH), 30.28 (CH$_2$), 30.03 (CH$_2$), 21.87-19.90 (CH$_3$—Ac), 16.00 (C—H$_2$)

$^{31}$P-NMR (81 MHz, d$_8$-toluene): δ 2.72 (1P), −2.75 (1P), −3.36(1P), −3.42 (1P)

MS (neg. mode, FAB, NBA) in/z (%): 1055 [M−CH$_2$OAc$^+$] (45), 983 [M−2CH$_2$OAc$^+$+H$^+$] (7)

MS (pos. mode, FAB, NBA) m/z (%): 1151 [M+Na$^+$] (9), 1129 [M+H$^+$] (18), 1057 [M+2H$^+$−CH$_2$OAc$^+$] (24), 985 [M+3H$^+$−2CH$_2$OAc$^+$] (26), 913 [M+4H$^+$−3CH$_2$OAc$^+$] (24), 841 [M+5H$^+$−4CH$_2$OAc$^+$] (24), 769 [M+6H$^+$−5CH$_2$OAc$^{+]}$ (22), 697 [M+7H$^+$6CH$_2$OAc$^+$] (18), 621 [M+8H$^+$−7CH$_2$OAc$^+$] (5)

HR-MS calcd. for C$_{31}$H$_{47}$O$_{32}$P$_4$ [M−CH$_2$OAc$^+$] 1055.1001, found 1055.1029

EXAMPLE 8

Cystic Fibrosis Human Nasal Epithelial Cell Assay

CF Human Nasal Epithelial (CFHNE) Cell Isolation and Proliferation

Nasal Polyps were surgically obtained from a CF patient at Children's Hospital (Seattle, Wash.), transported on ice in a sterile container containing a 1:1 mixture of Dulbecco's modification of minimum essential medium Eagle and Ham's F-12 nutrient medium (DMEM/F-12) (Irvine Scientific, Santa Ana, Calif.) supplemented with 100 U/mL penicillin, 0.1 mg/mL streptomycin, 10 mM HEPES, and 2 mM L-glutamine. The tissue samples were aseptically removed from the transport medium and washed (repeated 5 times) by suspending in 40 mL of Joklik's modification of minimum essential medium Eagle (JMEM) at 4° C., and centrifuging at 500 rpm. The supernatant was aspirated and discarded. The tissue was then transferred to JMEM containing 200 U/mL penicillin, 0.2 mg/mL streptomycin, 0.1 mg/mL gentamycin sulfate (Clonetics, San Diego, Calif.), and 0.1 μg/mL amphotericin-B (Clonetics), and 0.1% Protease, washed an additional two times, suspended in 15 nm in a 10 cm tissue culture dish, and incubated at 4° C. for 24 hours. The tissue samples were then gently triturated, the connective tissue aseptically removed, and the remaining cell suspension centrifuged at 1000 rpm. The supernatant was aspirated and the pellet was resuspended in 10 mL proliferation media, consisting of Keratinocyte-Serum Free Medium (KSFM) (Gibco-BRL, Grand Island, N.Y.) containing 5 ng/ml EGF (Gibco), 50 μg/mL BPE (Gibco), 5 μg/mL insulin, 5 μg/mL transferrin, 5 μg/ml sodium selenite, 10 nM 3,3',5-triiodo-L-thyronine, 200 nM hydrocortisone, 100 U/mL penicillin, 0.1 mg/mL streptomycin, and 2 mM L-glutamine. The cell suspension was transferred to 2.10 cm tissue culture dishes coated with 3 μg/cm$^2$ rat-tail collagen (Type I) (Becton-Dickinson, Bedford, Mass.), incubated at 37° C. in an humidified atmosphere of 5% CO$_2$ and 95% air. The cells were allowed to grow for 6 days (~70% confluence) with the media being replaced with fresh media every other day. The cells were then trypsinized using 0.025% trypsin-EDTA for 5 min. The cell suspension was collected, the trypsin deactivated with 10% Fetal Bovine Serum, and centrifuged at 1000 rpm for 5 min. The cells were then counted using an hemocytometer with a yield of $3\times10^6$ cells per dish. The supernatant was aspirated and the cells were resuspended in KSFM and plated at a density of $10^4$ cells/cm$^2$.

CFHNE Cell Ussing Chamber Preparation

The CFHNE cells were prepared for Ussing Chamber studies using Snapwell permeable supports (0.4 μm pore size) (Corning Costar, Cambridge, Mass.) coated with 3 μg/cm$^2$ rat-tail collagen (type 1). Cells were plated at $9\times10^3$ cells/cm$^2$ in KSFM. After 2 days, an air-liquid interface (ALI) was initiated in DMEM/F-12 containing: 2% Fetal Clone III (Hyclone, Logan, Utah), 2.5 μg/mL insulin, 2.5 μg/mL transferrin, 2.5 μg/mL sodium selenite, 20 nM hydrocortisone, 1.5 μM epinephrine, 50 μg/mL BPE, 1 nM 3,3',5-triiodo-L-thyronine, 3.3 nM All-trans retinoic acid, 250 nM ethanolamine, 250 nM O-phosporylethanolamine, 100 U/mL penicillin, 0.1 mg/ml streptomycin, and 2 mM L-glutamine. The CFHNE monolayers reached maximal resistance (~200 Ω/cm$^2$) 5-7 days after initiation of ALI. All media/reagents, unless otherwise specified, were supplied by Sigma Chemical Co., St. Louis, Mo.

Figure 10A:
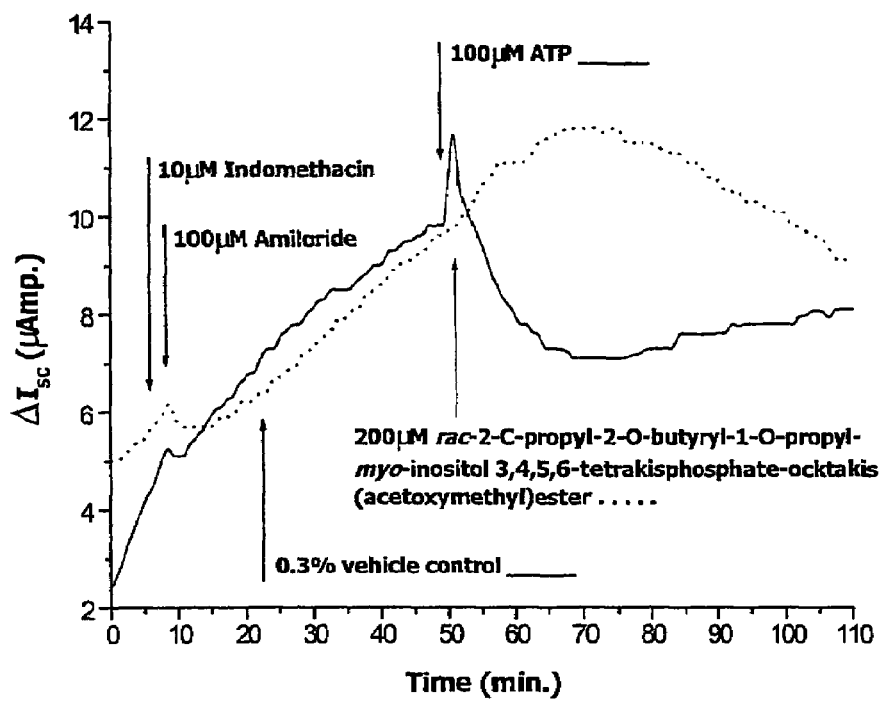
FIG. 10A is a graph showing the effect of rac-2-O-butyryl-2-C-propyl-1-O-propyl-myo-inositol 3,4,5,6-tetrakisphosphate-octakis(acetoxymethyl)ester ("Compound A") on the stimulation of an increase $I_{sc}$ in CFHNE (passage 3) in comparison to response to ATP, as described in Example 8. Example 10B is a graph showing prolonged increase in $I_{sc}$ following ATP addition in CFHNE.
Figure 10B:
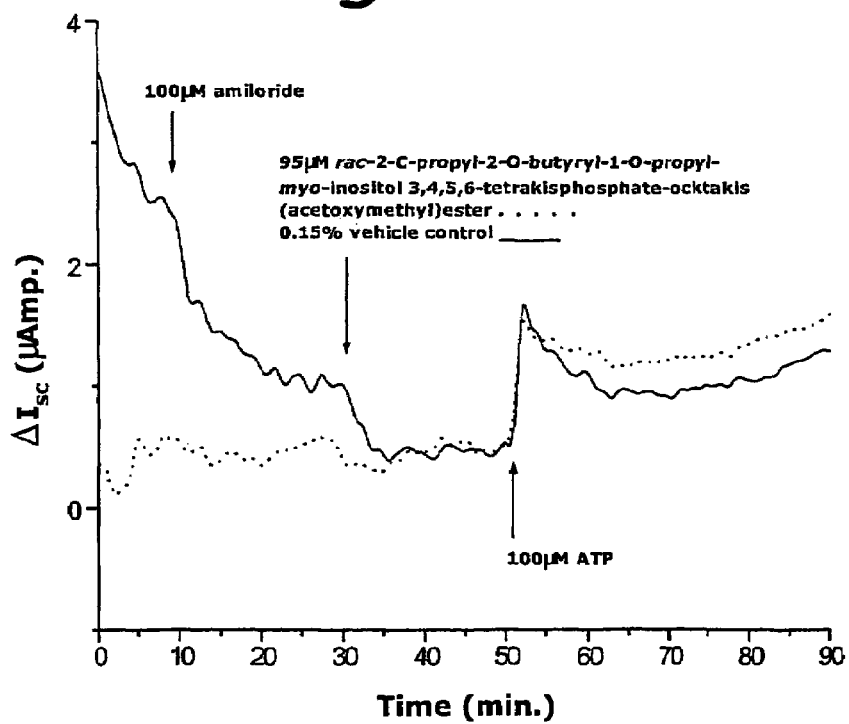

Effect of rac-2-O-Butyryl-2-C-propyl-1-O-propyl-myo-inositol 3,4,5,6-Tetrakis-phosphate Octakis(acetoxymethyl) Ester The compound rac-2-O-butyryl-2-C-propyl-1-O-propyl-myo-inositol 3,4,5,6-tetrakisphosphate octakis(acetoxymethyl)ester ("Compound A") was tested as described above. The results are shown in FIGS. 12A and 12B. As can be seen in FIG. 10A, Compound A (200 μM), added basolaterally, elicited a prolonged increase in $I_{sc}$ comparable in amplitude to that stimulated with ATP. Although 95 μM had little direct effect, it appeared to prolong the response to subsequent stimulation with ATP (FIG. 10B.)

CONCLUSION

Ins(3,4,5,6)P$_4$ is an endogenous inhibitor of Ca$^{2+}$ activated Cl$^-$ (CLCA) channels. Ins(3,4,5,6)P$_4$ antagonists described herein overcome inhibition and promote Cl$^-$ secretion in human colonic epithelia. Rationale modification of the molecular structure of the antagonists has yielded a 10-fold improvement in potency. In addition, some compounds were generated that triggered transepithelial currents in primary nasal epithelia from CF patients and colonic epithelia. In at least one case, a chloride current was identified in CFHNE using patch clamp techniques.

EXAMPLE 9

Colonic Epithelial Cell Assay

Transepithelial chloride secretion is key to the regulation of water flow across gut epithelia. Diseases of chloride and fluid transport include cystic fibrosis and secretory diarrhea. As the endogenous factors which regulate chloride secretion are uncovered, the chances that we will be able to better modulate fluid secretion in diseased epithelial is improved.

The Regulation of Cl$^-$ Secretion in Colonic Epithelia.

Transepithelial chloride secretion in colonic epithelia is controlled through at least three separate apically located chloride Cl$^-$ channels and a least two separately regulated basolateral potassium channels. Apical chloride efflux is counterbalanced by basolateral K efflux, preserving electroneutrality. Two of the apical chloride channels, the cystic fibrosis transmembrane regulator and the outwardly rectifying chloride channel are functionally linked and triggered by elevations in cAMP levels. The calcium dependent chloride channel is regulated independently of the cAMP triggered pathways. There are two main signaling pathways regulating this function T$_{84}$ monolayers retain many receptor-mediated Cl$^-$ secretory mechanisms including those involving changes in free cytosolic Ca$^{2+}$ ([Ca$^{2+}$]$_i$) and the CFTR. Agents which elevate [Ca$^{2+}$]$_i$ such as histamine, carbachol, Ca$^{2+}$ ionophores and thapsigargin, stimulate varying degrees of Cl$^-$ secretion across T$_{84}$ monolayers (Dharmsathaphorn et al., "Multiple calcium-mediated effector mechanisms regulate chloride secretory responses in T84 cells," *Am. J. Physiol.* 256:C1224-C$_{1230}$ (1989); Kachintorn et al., "Activation by calcium alone of chloride secretion in T84 epithelial cells" *British J: Pharmacology* 109:510-517 (1993)). A rise in [Ca$^{2+}$]$_i$ can trigger Cl$^-$ secretion through effects on both Cl$^-$ and K$^+$ channels, since basolateral K efflux can be rate limiting because it is necessary for the restoration of electroneutrality. Although cyclic AMP also stimulates Cl$^-$ secretion in T$_{84}$ cells, Ca$^{2+}$ mediated Cl$^-$ secretion (CaMCS) is through a Cl$^-$ channel which is distinct from the cyclic AMP mediated Cl$^-$ secretion and is modulated by the Ca/calmodulin dependent protein kinase II (CaMKII) (Worrel et al., "CaMKII mediates stimulation of chloride conductance by calcium in T84 cells," *Am. J: Physiol.* 260(*Cell Physiol* 29):C877-C882 1991; Preston, et al., "Calmodulin defects cause the loss of Ca$^{++}$-dependent K$^+$ currents in two pantophobiac mutants of Paramecium tetraurelia," *J. Memb. Biol.* 115:51-60, (1990); Okada, et al., "Evidence for the involvement of calmodulin in the operation of Ca$^{++}$-activated K$^+$ channels in mouse fibroblasts," *J. Memb. Biol.* 96:121-128 (1987).

Role of Inositol Polyphosphates in the Regulation of Chloride Secretion.

We have found that the endogenous regulator of Ca$^{2+}$-mediated Cl$^-$ secretion, D-myo-inositol(3,4,5,6)tetrakisphosphate (Ins(3,4,5,6)P$_4$), becomes elevated in T$_{84}$ cells following stimulation with cholinergic agonists but not histaminergic agonists or cyclic AMP-elevating agents. (Kachintorn, et al. 1992). Elevation of D-myo-Ins(3,4,5,6)P$_4$ levels, either through cholinergic stimulation or addition of a cell permeant form of Ins(3,4,5,6)P$_4$ results in the uncoupling of subsequent Cl$^-$ secretion from the elevation of intracellular Ca$^{2+}$ levels (Vajanaphnich, et al., "Long-term uncoupling of chloride secretion from intracellular calcium levels by Ins(3, 4,5,6)P$_4$," *Nature* 371:711-714 (1994)). Studies using whole cell patch clamp with intracellular perfusion of inositol tetrakisphosphates indicate that Ins(3,4,5,6)P$_4$ directly modulates an apically located Ca$^{2+}$/calmodulin kinase regulated Cl$^-$ channel in T$_{84}$ (Xie, et al., J. Biol. Chem. 271:14092-14097 (1996)). This effect may be mediated by an okadaic acid sensitive protein phosphatase. On the other hand, Ca$^{2+}$ dependent Cl$^-$ channels reconstituted in planar lipid bilayers could also be regulated by low levels of Ins(3,4,5,6)P$_4$ in the absence of phosphatase activities (Ismailov, et al., "A biologic function for an "orphan" messenger: D-myo-inositol 3,4,5,6-tetrakisphosphate selectively blocks epithelial calcium-activated chloride channels," *Proc Natl Acad Sci USA* 93:10505-9 (1996).

Method Detail:

Cl$^-$ secretion in colonic epithelial cells was measured as short circuit current (I$_{sc}$) across T$_{84}$ monolayers grown to confluence on Snap-wells (Costar) and mounted in Ussing chambers equipped with voltage clamps (Physiologic Instruments, San Diego). Data was acquired and analyzed using AAcquire and Analyze@ software (Physiologic Instruments). $T_{84}$ cells (passages 18-48) were maintained as described previously in McRoberts, J. A. et al., "Cyclic AMP and $Ca^{2+}$-activated $K^+$ transport pathway in the apical membrane of a human colonic epithelial cell line," *J. Biol. Chem.* 260:14163-14172 (1985). After 0.7-10 days of incubation on Snap-wells, monolayers had formed tight junctions and were preincubated with 100, 200 or 400 mM $Bt_2$D-myo-Ins(3,4,5,6)$P_4$/AM for 30-min. prior to mounting. An extracellular concentration of 200 uM corresponds to an intracellular concentration of 4 uM (Vajanaphnich, et al., "Long-term uncoupling of chloride secretion from intracellular calcium levels by Ins(3,4,5,6)$P_4$," *Nature* 371:711-714 (1994)). After an additional 30 min, 0.1 mM histamine was added and the $I_{sc}$ monitored. $Ca^{2+}$-dependent $Cl^-$ secretion was stimulated with histamine, a physiologically relevant agonist which does not have a measurable long term effect on inositol polyphosphate metabolism as does carbachol in this cell line (Kachintorn, et al., "Elevation of inositol tetrakisphosphate parallels inhibition of calcium-dependent chloride secretion in T84 colonic epithelia cells," *Am. J. Physiol., Cell* 264:C671-C676 (1993); Kachintorn et al., "Activation by calcium alone of chloride secretion in T84 epithelial cells" *British J. Pharmacology* 109:510-517 (1993)).

Figure 9A:
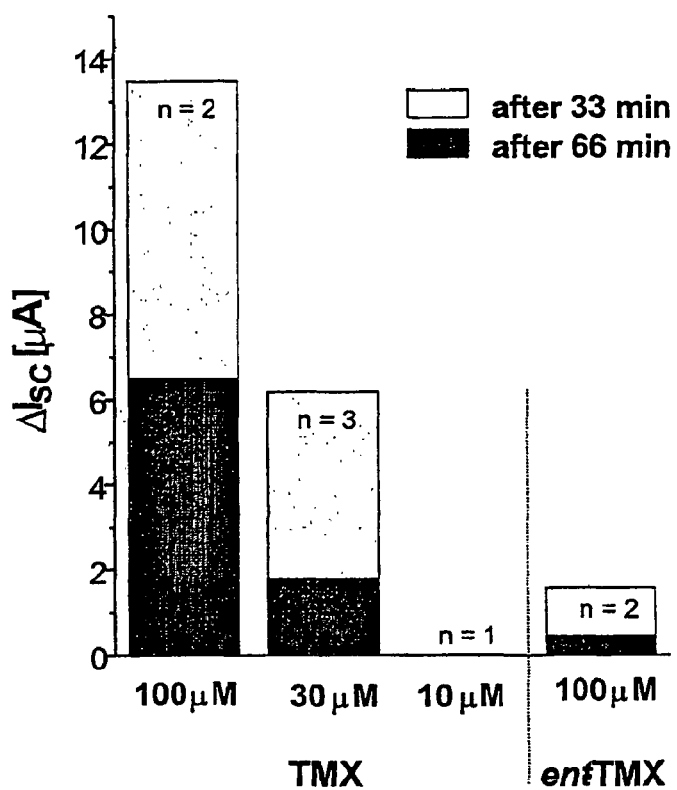
FIG. 9A is a bar graph showing the increase in short circuit current ($I_{sc}$) in monolayers of $T_{84}$ cells in Ussing chambers exposed to differing concentrations of D-2,3,5-tri-O-butyryl-myo-inositol 1,4,6-trisphosphate hexakis(proprionoxymethyl) ester ("TMX"; ent-TMX is the enantiomer of TMX), as described in Example 9.
Figure 9B:
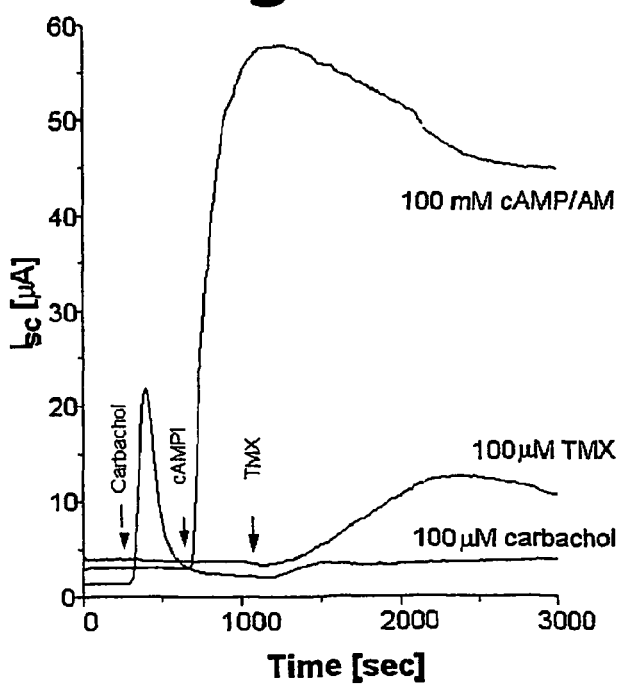
FIG. 9B is a graph showing that TMX induces a prolonged increase in $I_{sc}$ similar to cyclic AMP in colonic epithelial cell line $T_{84}$.
Figure 9C:
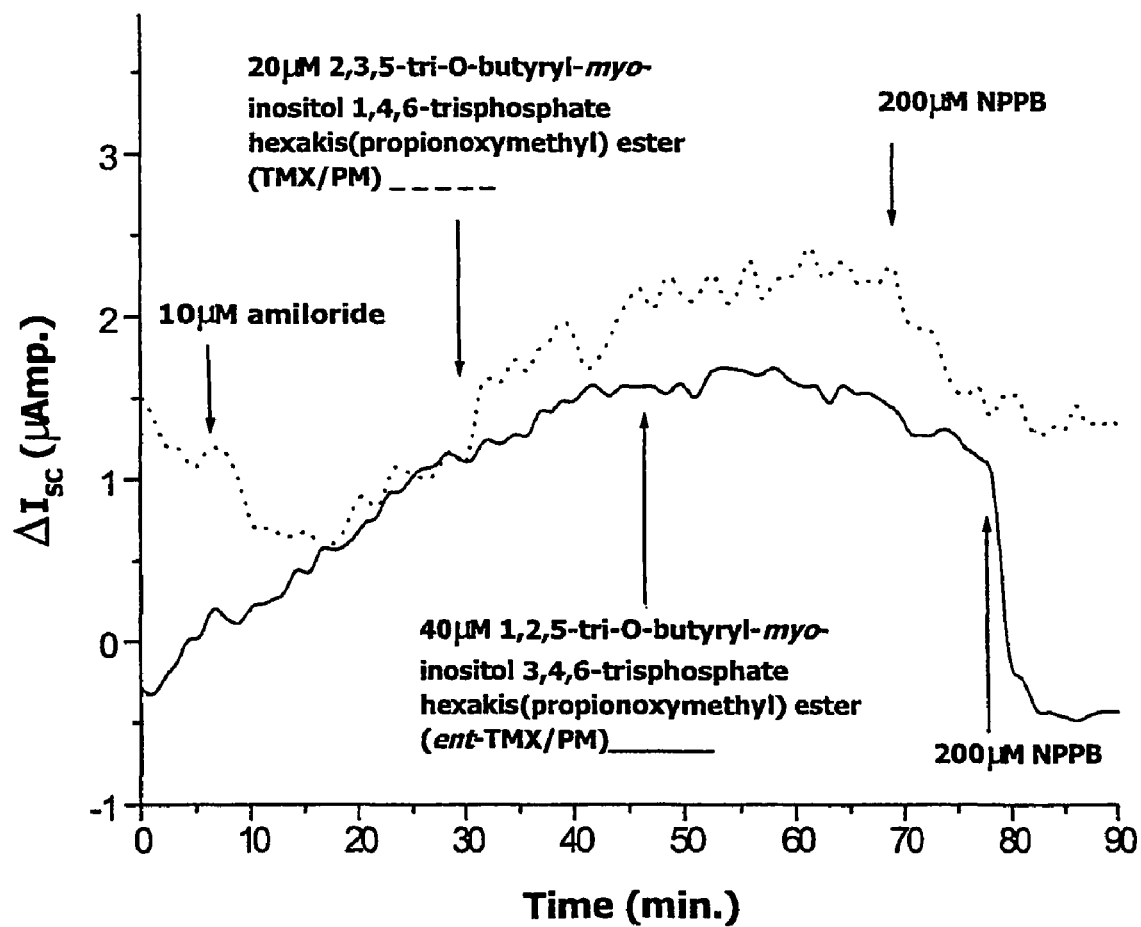
FIG. 9C is a graph showing the effect of acute addition of TMX in human CF nasal epithelia.

Effects of 2,3,5-Tri-O-butyryl-myo-inositol 1,4,6-Trisphosphate Hexakis-(proprionoxymethyl) Ester The increase in short circuit current ($I_{sc}$) in monolayers of $T_{84}$ cells in Ussing chambers exposed to differing concentrations of 2,3,5-tri-O-butyryl-myo-inositol 1,4,6-trisphosphate hexakis(proprionoxymethyl)ester ("$Bt_3Ins(1,4,6)P_3$/PM" or "TMX") is shown in FIG. 9A (where ent-TMX is the enantiomer of 2,3,5-tri-O-butyryl-myo-inositol 1,4,6-trisphosphate hexakis(proprionoxymethyl)ester (TMX). FIG. 9A depicts the effects of various doses of TMX on short circuit current ($I_{sc}$) in colonic and airway epithelial cells. This effect is specific because the enantiomer of TMX (ent-TMX-1,2,5-tri-O-butyryl-myo-inositol 3,4,6-trisphosphate hexakis-(proprionoxymethyl) ester is inactive (FIGS. 11A and 11C). The pro-secretory activity of TMX may be attributed, at least in part, to a stimulatory effect on intracellular calcium levels due to its structural similarity to inositol 1,4,5-trisphosphate. In addition, its inhibitory effect on the accumulation of Ins(3,4,5,6)$P_4$ would enable $Ca^{2+}$-stimulated $Cl^-$ secretion. In addition, it may directly trigger $Cl^-$ secretion through binding to $Cl^-$ channels directly.

Effect of rac-1,2-O-Isopropylidene-2-C-propyl-myo-inositol 3,4,5,6-Tetrakisphosphate octakis(acetoxymethyl) Ester ("Compound B")

Figure 11:
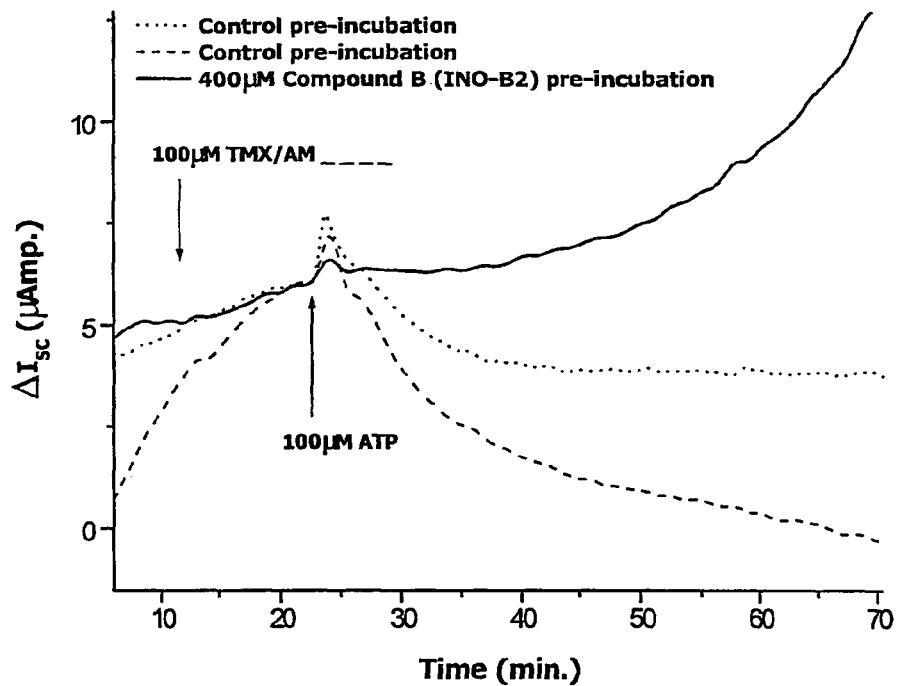
FIG. 11 is a graph showing that TMX and Compound B reverse the negative component of the ATP effect on $I_{sc}$ in CFHNE. Data are the average of duplicates. The solid line indicates preincubation with Compound B at 400 µM.
Figure 12:
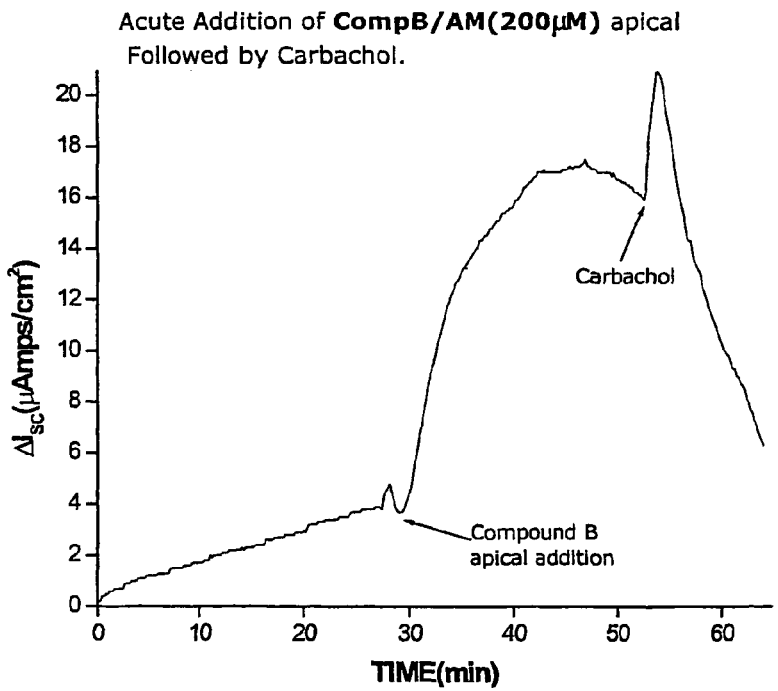
FIG. 12 is a graph showing that Compound B triggers an increase in $I_{sc}$ in $T_{84}$ cells, as described in Example 9. Compound B was applied acutely to the apical surface of $T_{84}$ monolayers mounted in Ussing chambers at the indicated time, as described in Example 9. After 25 min. 10$^{-4}$ M carbachol was added. Data plotted as $\Delta I_{sc}$ (µA/m$^2$) represents one monolayer.

Using the foregoing procedures, the compound rac-1,2-O-isopropylidene-2-C-propyl-myo-inositol 3,4,5,6-tetrakisphosphate octakis(acetoxymethyl)ester ("Compound B") was tested and compared with TMX. FIG. 11 shows the effect of TMX and rac-1,2-O-isopropylidene-2-C-propyl-myo-inositol 3,4,5,6-tetrakis-phosphate octakis(acetoxymethyl) ester ("Compound B") on the negative component of the ATP effect on $I_{sc}$ in CFHNE. As shown in FIG. 12, Compound B triggers an increase in $I_{sc}$ in $T_{84}$ cells. Compound B was applied acutely to the apical surface of $T_{84}$ monolayers mounted in Ussing chambers at the indicated time. After 25 min. $10^{-4}$ M carbachol was added. Data plotted as $\Delta I_{sc}$ ($\mu$A/$cm^2$) in FIG. 12 represents one monolayer. As shown in FIG. 12, ATP ($10^{-4}$ M) stimulated a transient increase in $I_{sc}$ followed by a prolonged decrease when added to monolayers pretreated with vehicle. This decrease was attenuated in monolayers exposed to TMX for 10 min. In contrast, although preincubation with, 200 $\mu$M Compound B (rac-1,2-O-isopropylidene-2-C-propyl-myo-inositol 3,4,5,6-tetrakisphosphate octakis(acetoxy-methyl) ester) inhibited the transient increase following ATP, it totally reversed the negative phase, instead causing a long term increase in $I_{sc}$ in CFHNE monolayers. Compound B also had an acute effect in $T_{84}$ monolayers, triggering a large and prolonged increase in $I_{sc}$.

Figure 13:
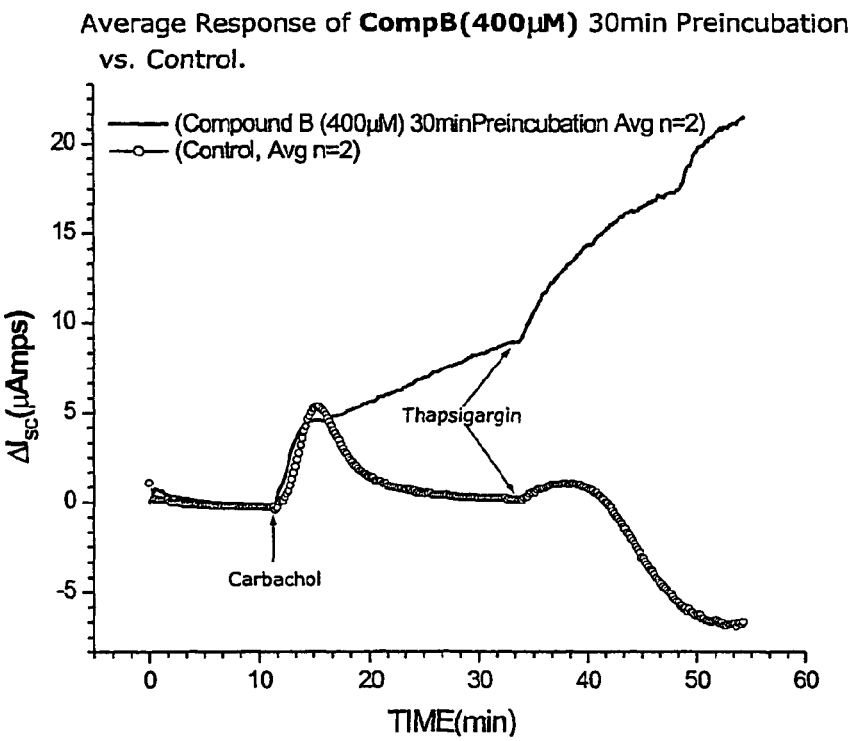
FIG. 13 is a graph showing monolayers of colonic epithelia ($T_{84}$) preincubated for 30 minutes with Compound B have a prolonged increase in $I_{sc}$ response to the calcium elevating agents, carbachol and thapsigargin, as described in Example 9.

Effect of rac-1,2-O-Isopropylidene-2-C-propyl-myo-inositol 3,4,5,6-Tetrakis-phosphate octakis(acetoxymethyl) Ester ("Compound B") At 400 $\mu$M with 30 Minute Preincubation We have previously demonstrated that carbachol applied basolaterally to the monolayers of $T_{84}$ colonic epithelia for a period of 5 minutes or more results in elevated intracellular levels of Ins(3,4,5,6)$P_4$ that mediates inhibition of subsequent increase in $I_{sc}$ stimulated by the calcium-elevating agent, thapsigargin (Vajanaphanich, et al. 1994 Nature). Ins(3,4,5,6)$P_4$ elevation may also mediate the "turn off" of the increased $I_{sc}$ following carbachol. Inositol polyphosphate analogs of Ins(3,4,5,6)$P_4$ with substitutions at the 1 and 2 position that restrict the flexibility of the molecule could compete with endogenous Ins(3,4,5,6)$P_4$-mediated inhibition and prolong and augment chloride secretion stimulated through elevation of intracellular calcium. For instance, preincubation with Compound B for 30 minutes both prolongs the carbachol induced increase in $I_{sc}$ in colonic epithelia, $T_{84}$, and overcomes the inhibitory effect of carbachol pretreatment on the thapsigargin induced increase in $I_{sc}$ as shown in FIG. 13.

Figure 14:
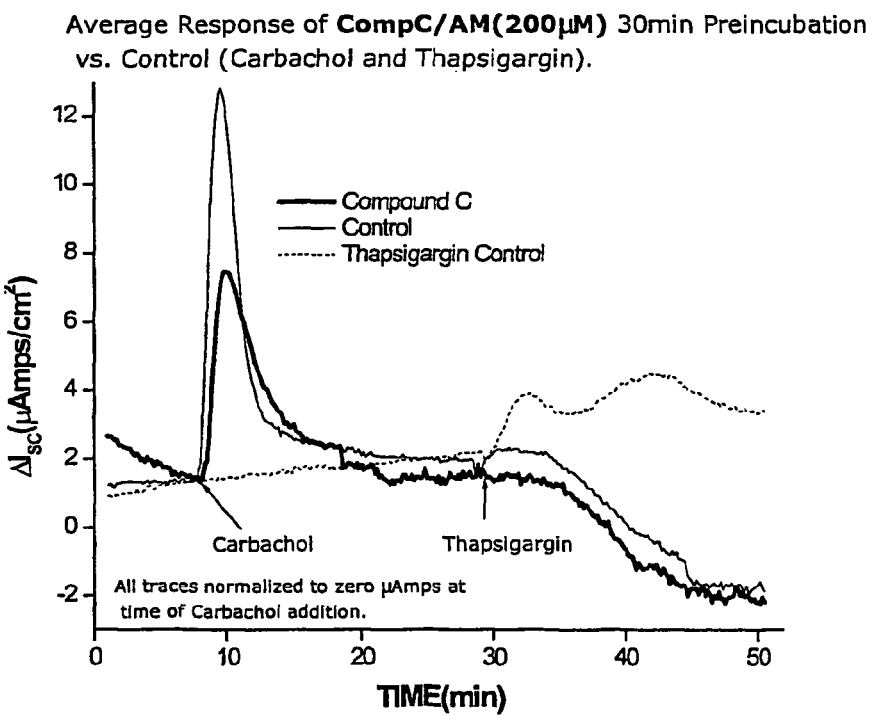
FIG. 14 is a graph showing that preincubation of colonic epithelia, $T_{84}$, with 200 µM Compound C for 30 minutes reduces the magnitude of the subsequent increase in Isc in response to carbachol, as described in Example 9.
Figure 15:
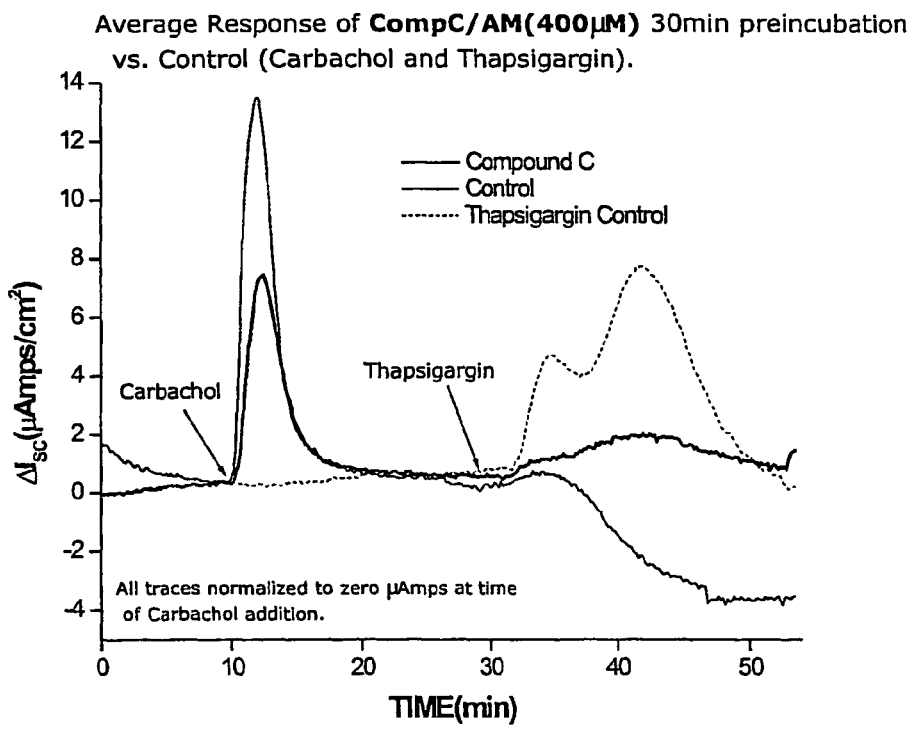
FIG. 15 is a graph showing that preincubation of colonic epithelia, $T_{84}$, with 400 µM Compound C for 30 minutes reduces the magnitude of the subsequent increase in $I_{sc}$ in response to carbachol but partially restores the response of the monolayers to thapsigargin, as described in Example 9. Carbachol has been shown to reduce the subsequent $I_{sc}$ response of $T_{84}$ monolayers to thapsigargin.

Effect of (5aa,6a,7b,8a,9b,9aa)-6,7,8,9-Tetrakis[[bis(acetoxymethoxy)phosphoryl]-oxy]-5a-[(2'-methoxy)ethoxy] methoxy-decahydro-benzo[b]oxepin ("Compound C") At 200 $\mu$M with 30 Minute Preincubation Monolayers of $T_{84}$ colonic epithelia were preincubated with 200 $\mu$M or 400 $\mu$M Compound C for 30 minutes prior to mounting in Ussing chambers. The $I_{sc}$ response to stimulation with the calcium elevating agents carbachol and thapsigargin were subsequently compared and depicted in FIGS. 14 and 15. Both concentrations of Compound C inhibited the response to carbachol by approximately 50% as seen in FIGS. 14 and 15.

Effect of rac-2-O-Butyryl-2-C-propyl-1-O-propyl-myo-inositol 3,4,5,6-Tetrakisphosphate-octakis(acetoxymethyl) ester ("Compound A") At 200 $\mu$M with 30 Minute Preincubation (Carbachol and Thapsigargin)

Figure 16:
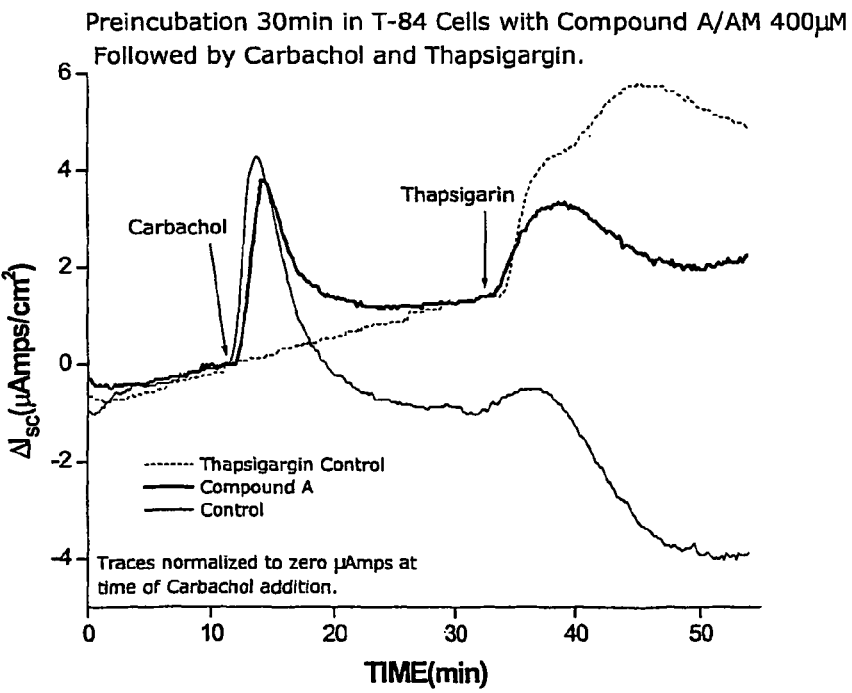
FIG. 16 is a graph showing that preincubation of $T_{84}$ monolayers with Compound A (400 µM) partially restores the $I_{sc}$ response to thapsigargin following carbachol, as described in Example 9.

Monolayers of $T_{84}$ colonic epithelia were preincubated with 400 $\mu$M Compound A for 30 minutes prior to mounting in Ussing chambers. The $I_{sc}$ response to stimulation with the calcium elevating agents carbachol and thapsigargin were subsequently compared and depicted in FIG. 16. Pretreatment with Compound A did not affect the response to carbachol but partially reversed the inhibition of thapsigargin induced chloride secretion as seen in FIG. 16.

Effect of rac-1-O-butyryl-2-C-propyl-myo-inositol 1,2,4,5,6 pentakisphosphate-dekakis(acetoxymethyl) ester (Compound D) on $I_{sc}$ in a human colonic epithelial cell line, $T_{84}$.

Figure 17:
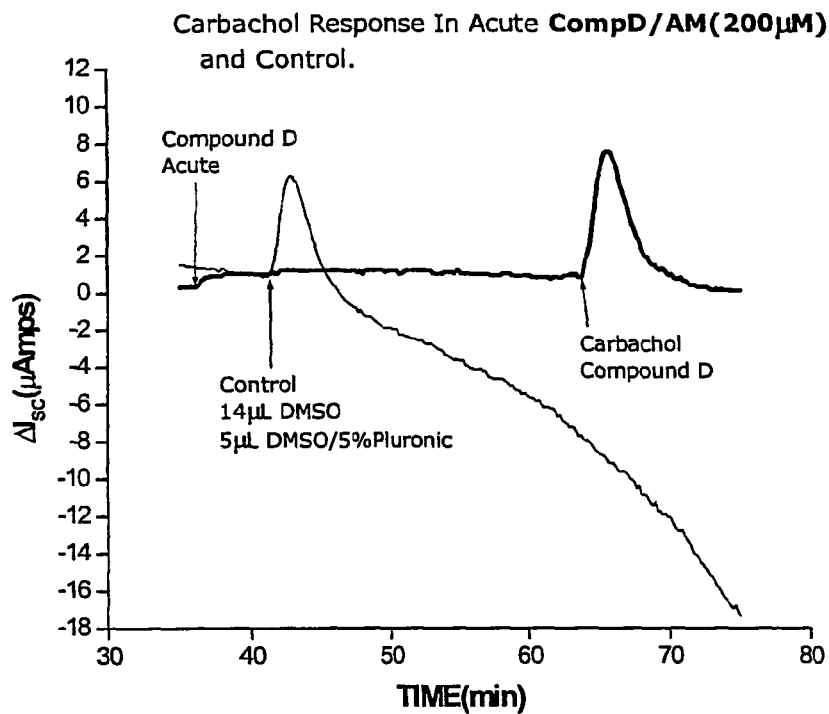
FIG. 17 is a graph showing that Compound D has a small acute effect increasing basal $I_{sc}$ in colonic epithelia, $T_{84}$, as described in Example 9. However, there is little effect on subsequent carbachol-stimulated $I_{sc}$.

Monolayers of the human colonic epithelial cell line, $T_{84}$ were mounted in Ussing chambers and treated acutely with Compound D. As can be seen in FIG. 17 200 $\mu$M Compound D stimulated a small increase in basal $I_{sc}$ but had little effect on subsequent carbachol-stimulated $I_{sc}$.

Effect of (4aa, 5a,6b,7a,8b, 8aa)-5,6,7,8-tetrakis [bis9acetoxymethoxy)phosphoryl]-oxy]-4a-butyryloxy-octahydro-chromen (Compound G) At 200 $\mu$M with 30 Minute Preincubation (Carbachol and Thapsigargin)

Figure 18:
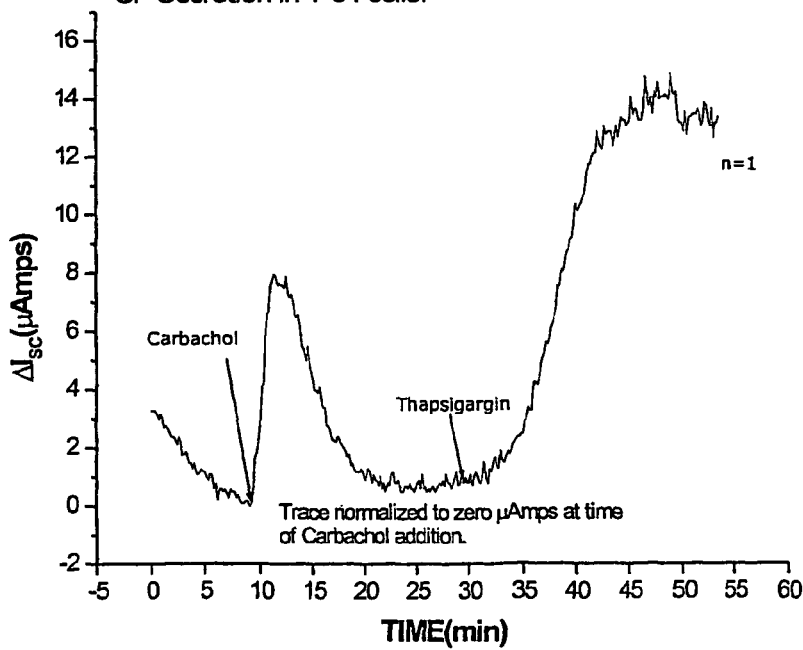
FIG. 18 is a graph showing that preincubation with Compound G reverses the carbachol-mediated inhibition of thapsigargin-stimulated increase in $I_{sc}$ in $T_{84}$ colonic epithelia, as described in Example 9.

Monolayers of $T_{84}$ colonic epithelia were preincubated with 200 $\mu$M Compound G for 30 minutes prior to mounting in Ussing chambers. The $I_{sc}$ response to stimulation with the calcium elevating agents carbachol and thapsigargin were subsequently compared and depicted in FIG. 18. Pretreatment with Compound G did not affect the response to carbachol but reversed the inhibition of thapsigargin induced chloride secretion as seen in FIG. 18.

EXAMPLE 10

Inflammation Studies

Materials:

Arachidonic Acid (Nu-Chek, Elysian, Minn. 56028); Indomethacin (stock=12.5 mg/mL acetone). Prednisolone (Sigma Chem, P6004) 20 mM dissolved in acetone; Animals: Female Balb/c mice (B&K laboratories) and Swiss-Webster hybrid (B& K Laboratory, Kent, Wash.)

Method

The right ear of each mouse was used for the test compound. Unless otherwise indicated each compound was adjusted to 20 mM by dilution into DMSO or DMSO/5% Pluronic F127 as indicated and 1 or 2 microliters were applied to the test ear. Thirty minutes after each compound was applied, 4 mg arachidonic acid was applied (4 μL/ear; 2 μL/side) to both ears of each mouse. Measurements of edema were taken 60 min after the application of arachidonic acid with microcalipers (Oditest, Scientific Supply and Equipment) unless otherwise indicated. The results are shown in FIG. 15 as millimeters×$10^{-2}$ measured at the thickest point of each ear. Control measurements were performed on ears that were only treated with arachidonic acid.

Response to prednisolone (20 μL of 20 mM/ear; 10 μl/side) added 3 hrs prior 20' to arachidonic acid or indomethacin (5 μg/ear) added 30 min prior to test compounds was determined. The results are shown in Table A, where the anti-inflammatory/inflammatory effects of 20 nanomoles/ear of the indicated compounds were tested as described in Methods. Each plus represents a change from control (arachidonic acid alone) of 2.5 mm×$10^{-2}$. Effects were compared with those of Indomethacin (400 nmols/ear).

TABLE A

Effects of Inositol Polyphosphate Analogs on arachidonic acid-induced inflammation in mouse ears

| Compound[1] | Ear Thickness (mm × $10^{-2}$) | n |
|---|---|---|
| Control (arachidonic acid + vehicle) | 56.5 ± 1.57 | 10 |
| A | 52.5 ± 5.5 | 3 |
| B | 56.1 ± 2.1 | 3 |
| C | 50.0 ± 5.5 | 3 |
| D | 44.0 ± 1.4 | 4 |
| D | 44.2 ± 6.5 | 3 |

TABLE A-continued

Effects of Inositol Polyphosphate Analogs on arachidonic acid-induced inflammation in mouse ears

| Compound[1] | Ear Thickness (mm × $10^{-2}$) | n |
|---|---|---|
| Tri-cyclo | 49.8 ± 2.5 | 4 |
| TMX/AM | 44.1 ± 2.3 | 3 |

[1]Test Compounds:
Compound A: rac-2-O-butyryl-2-C-propyl-1-O-propyl-myo-inositol 3,4,5,6-tetrakisphosphate-octakis(acetoxymethyl) ester
Compound B: rac-1,2-O-isopropylidene-2-C-propyl-myo-inositol 3,4,5,6-tetrakisphosphate-octakis(acetoxymethyl) ester
Compound C: (5aa,6a,7b,8a,9b,9aa)-6,7,8,9-tetrakis[[bis(acetoxymethoxy)-phosphoryl]oxy]-5a-[(2'-methoxy)ethoxy]methoxy-decahydro-benzo[b]oxepin
Compound D: rac-1-O-butyryl-2-C-propyl-myo-inositol 2,3,4,5,6-pentakisphosphate-dekakis(acetoxymethyl) ester
Compound E (INO-E1): rac-2-O-butyryl-1-O-octyl-myo-inositol 3,4,5,6-tetrakisphosphate octakis(acetoxymethyl) ester
Compound F: rac-2-O-butyryl-3-O-isopropyl-myo-inositol 1,4,5,6-tetrakisphosphate-octakis(acetoxymethyl) ester
Compound G: (4aa, 5a,6b,7a,8b,8aa)-5,6,7,8-tetrakis[[bis(acetoxymethoxy)-phosphoryl]oxy]-4a-butyryloxy-octahydro-chromen
Tricyclo Compound: (1S, 2R, 3S, 4R, 5S, 6S, 8R)-2,3,4,5-tetrakis[[bis-(acetoxymethoxy)phosphoryl]oxy]-7,12-dioxa-tricyclo-[6.3.1.0(1,6)]-dodecane
TMX Compound: 2,3,5-tri-O-butyryl-myo-inositol 1,4,6-trisphosphate hexakis-(acetoxymethyl) ester Acute inflammation: Membrane permeant inositol polyphosphate analogs were administered topically and tested for inhibition of inflammatory symptoms induced by arachidonic acid on the ear of Swiss Webster mice. D-2,3-Di-O-butyryl-myo-inositol 1,4,5,6 tetrakisphosphate octakis(acetoxymethyl)ester had an inhibitory effect comparable in intensity to that of indomethacin (250 μg/animal) at a dose of 20-30 μg/animal. More potent was D-2,3-Di-O-butyryl-myo-inositol 1,4,5,6 tetrakisphosphate octakis(propionoxymethyl)ester which had topical anti-inflammatory effects with values ranging from 0.25-1.5 μg/animal. D-1-O-octyl-2-O-butyryl-myo-inositol 1,4,5,6-tetrakisphosphate-octakis-(propionoxymethyl)ester (INO-E3) was yet more potent with an $ED_{50}$ of 7-14 :g/kg, and has been shown to be effective when applied topically, intraperitoneally and orally. No macroscopic negative effects were observed with ip injections up to 50 μg/animal and iv injections of 20 μg/animal several weeks after treatment.

Several modes of delivery were assayed, including a simple cream. Systemic effects were observed with more lipophilic formulations. Compounds injected into the tail vein of the mouse or delivered ip resulted in an anti-inflammatory effect comparable to the topical applications, with no apparent side effects. Therefore, inositol polyphosphate derivatives show promise as both topical and systemic anti-inflammatory agents for the treatment of diseases such as inflammatory bowel disease, arthritis, asthma, and adult respiratory distress syndrome in addition to contact dermatitis.

REFERENCES

1. Carlson, R P. O'Neill-Davis, L. Chang, J. Lewis, A J. 1985. Modulation of mouse ear edema by cyclooxygenase and lipoxygenase inhibitors and other pharmacologic agents. Agents and Actions, 17:2, 197-204.
2. Chang, J. Blazek, E. Skowronek, M. Marinari, L. Carlson, R P. 1987. The antiinflammatory action of guanabenz is mediated through 5-lipoxygenase and cyclooxygenase inhibition. Europ. J. Pharmac. 142, 197-205

3. Simon, L S, MD 1999. Role and regulation of Cyclooxygenase-2 during inflammation. Am. J. Med, 106(5B): 37S-42S

EXAMPLE 11

Composition for Systemic Administration for Lung Pancreas, Gastrointestinal and Vaginal and Ductile Manifestations of Cystic Fibrosis A composition comprising physiological saline and a therapeutically effective amount of an inositol derivative of Examples 1-7 is administered intravenously to a patient on a daily prophylactic basis. As a result of the administration, the patient has reduced viscosity of mucosal secretions, improved airway clearance and oxygenation of the blood.

EXAMPLE 12

Composition for Patient with Intestinal Symptoms

A composition comprising a physiologically acceptable carrier or vehicle and a therapeutically effective amount of an inositol derivative of Examples 1-7 the present invention is administered once daily for one week, in the form of an enema, to a patient having ulcerative colitis. As a result of the administration, the patient has improved digestion, reduced risk of intestinal obstruction and improved regularity of bowel function.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound selected from the group consisting of 2-O-butyryl-2-C-propyl-3-O-propyl-myo-inositol 1,4,5,6-tetrakisphosphate; 2-O-butyryl-2-C-propyl-1-O-propyl-myo-inositol 3,4,5,6-tetrakisphosphate; 2,3-O-isopropylidene-2-C-propyl-myo-inositol 1,4,5,6-tetrakisphosphate; 1,2-O-isopropylidene-2-C-propyl myo-inositol 3,4,5,6-tetrakisphosphate, 2-O-butyryl-1-O-octyl-myo-inositol 3,4,5,6-tetrakisphosphate or a racemate, stereoisomer, ester or pharmaceutically acceptable salt thereof.

2. A method for regulating chloride secretion and/or inhibiting inflammation in a cell or tissue, comprising contacting the cell or tissue with an effective amount of a compound selected from the group consisting of 2-O-butyryl-2-C-propyl- 3-O-propylmyo-inositol 1,4,5,6-tetrakisphosphate; 2-O-butyryl -2-C-propyl 1-O-propyl rnyo-inositol 3,4,5,6-tetrakisphosphate; 2,3-O-isopropylidene2-C-propyl-myo-inositol 1,4,5,6-tetrakisphosphate; 1,2-O-isopropylidene-2-C-propyl-myo-inositol 3,4,5,6-tetrakis- phosphate, 2-O-butyryl-1-O-octyl-myo-inositol 3,4,5,6-tetrakisphosphate or a racemate, stereoisomer, ester or pharmaceutically acceptable salt thereof.

3. A method of regulating chloride secretion and/or inhibiting inflammation in a human or animal patient in need thereof comprising administering to the patient a therapeutically effective amount of a compound selected from the group consisting of 2-O-butyryl-2-C-propyl3-O-propylmyo-inositol 1,4,5,6-tetrakisphosphate;2-O-butyryl-2-C-propyl 1 O-propyl-myo-inositol 3,4,5 ,6-tetra- kisphosphate; 2,3 -O-isopropylidene2-C-propyl-myo-inositol 1,4,5 ,6-tetrakisphosphate; 1,2-O-isopropylidene-2-C-propyl-myo-inositol 3,4,5,6-tetrakisphosphate, 2-O-butyryl-1-0-octyl- myo-inositol 3,4,5,6-tetrakisphosphate or a racemate, stereoisomer, ester or pharmaceutically acceptable salt thereof.

* * * * *

UNITED STATES PATENT AND TRADEMARK OFFICE
CERTIFICATE OF CORRECTION

PATENT NO. : 7,453,006 B2
APPLICATION NO. : 10/432340
DATED : November 18, 2008
INVENTOR(S) : A. Traynor-Kaplan et al.

It is certified that error appears in the above-identified patent and that said Letters Patent is hereby corrected as shown below:

| COLUMN | LINE | |
|---|---|---|
| 62 (Claim 1) | 6 | "-2-C-propyl myo-" should read -- -2-C-propyl-myo- -- |
| 62 (Claim 2) | 13-15 | "propyl- 3-O-propylmyo-inositol 1,4,5,6-tetrakisphosphate; 2-O-butyryl -2-C-propyl 1-O-propyl rnyo-inositol" should read --propyl-3-O-propyl-myo-inositol 1,4,5,6-tetrakisphosphate; 2-O-butyryl-2-C-propyl-1-O-propyl-myo-inositol-- |
| 62 (Claim 2) | 18 | "tetrakis- phosphate," should read --tetrakisphosphate;-- |
| 62 (Claim 3) | 27 | "-tetrakisphosphate;2-O-" should read -- -tetrakisphosphate; 2-O- -- |
| 62 (Claim 3) | 28 | "3,4,5 ,6-tetra- kisphosphate;" should read --3,4,5,6-tetra-kisphosphate;-- |
| 62 (Claim 3) | 29 | "1,4,5 ,6-" should read --1,4,5,6- -- |

UNITED STATES PATENT AND TRADEMARK OFFICE
CERTIFICATE OF CORRECTION

PATENT NO. : 7,453,006 B2
APPLICATION NO. : 10/432340
DATED : November 18, 2008
INVENTOR(S) : A. Traynor-Kaplan et al.

It is certified that error appears in the above-identified patent and that said Letters Patent is hereby corrected as shown below:

| COLUMN | LINE | |
|---|---|---|
| 62 (Claim 3) | 31 | "-1-0-octyl- myo-" should read -- -l-O-octyl-myo- -- |

Signed and Sealed this

Thirtieth Day of June, 2009

JOHN DOLL
*Acting Director of the United States Patent and Trademark Office*